(12) United States Patent
Tseng et al.

(10) Patent No.: US 9,931,423 B2
(45) Date of Patent: Apr. 3, 2018

(54) METHODS OF STERILIZING FETAL SUPPORT TISSUES

(75) Inventors: Scheffer Tseng, Pinecrest, FL (US); Ek Kia Tan, Miami, FL (US)

(73) Assignee: TISSUETECH, INC., Doral, FL (US)

( * ) Notice: Subject to any disclaimer, the term of this patent is extended or adjusted under 35 U.S.C. 154(b) by 0 days.

(21) Appl. No.: 14/240,712

(22) PCT Filed: Aug. 24, 2012

(86) PCT No.: PCT/US2012/052358
§ 371 (c)(1),
(2), (4) Date: May 14, 2014

(87) PCT Pub. No.: WO2013/032938
PCT Pub. Date: Mar. 7, 2013

(65) Prior Publication Data
US 2014/0342014 A1 Nov. 20, 2014

Related U.S. Application Data

(60) Provisional application No. 61/528,059, filed on Aug. 26, 2011.

(51) Int. Cl.
  A61K 35/50 (2015.01)
  A61L 2/00 (2006.01)
  A01N 1/02 (2006.01)
(52) U.S. Cl.
  CPC ............ A61L 2/0035 (2013.01); A01N 1/021 (2013.01); A61K 35/50 (2013.01)
(58) Field of Classification Search
  None
  See application file for complete search history.

(56) References Cited

U.S. PATENT DOCUMENTS

| | | | |
|---|---|---|---|
| 3,909,816 | A | 9/1975 | Teeters |
| 4,405,616 | A | 9/1983 | Rajadhyaksha |
| 4,798,611 | A | 1/1989 | Freement, Jr. |
| 4,801,586 | A | 1/1989 | Minaskanian et al. |
| 4,861,764 | A | 8/1989 | Samour et al. |
| 4,886,783 | A | 12/1989 | Minaskanian et al. |
| 4,983,396 | A | 1/1991 | Bodor et al. |
| 5,033,252 | A | 7/1991 | Carter |
| 5,052,558 | A | 10/1991 | Carter |
| 5,118,845 | A | 6/1992 | Peck et al. |
| 5,196,410 | A | 3/1993 | Francoeur et al. |
| 5,323,907 | A | 6/1994 | Kalvelage |
| 6,203,755 | B1 | 3/2001 | Odland |
| 6,521,179 | B1 | 2/2003 | Girardot et al. |
| 6,632,648 | B1 | 10/2003 | Kampinga et al. |
| 7,476,221 | B2 | 1/2009 | Sun et al. |
| 8,071,135 | B2 | 12/2011 | Liu et al. |
| 8,372,438 | B2 | 2/2013 | Daniel et al. |
| 8,486,374 | B2 | 7/2013 | Tamarkin et al. |
| 8,741,265 | B2 | 6/2014 | Tamarkin et al. |
| 9,132,156 | B1 | 9/2015 | Werber et al. |
| 9,295,753 | B1 | 3/2016 | Tello |
| 9,655,948 | B1 | 5/2017 | Koob et al. |
| 2002/0192272 | A1 | 12/2002 | Popp |
| 2003/0012687 | A1 | 1/2003 | MacPhee et al. |
| 2003/0180181 | A1 | 9/2003 | Greib et al. |
| 2004/0126878 | A1 | 7/2004 | Ramos et al. |
| 2004/0209235 | A1* | 10/2004 | Goldstein ............ A01N 1/0215 435/1.1 |
| 2008/0286378 | A1 | 11/2008 | Behrens et al. |
| 2008/0299087 | A1 | 12/2008 | Tsneg et al. |
| 2012/0141595 | A1 | 6/2012 | Tseng et al. |
| 2012/0189583 | A1 | 7/2012 | Liu et al. |
| 2013/0156863 | A1 | 6/2013 | Tseng et al. |
| 2014/0067058 | A1 | 3/2014 | Koob et al. |
| 2014/0112998 | A1 | 4/2014 | Tseng et al. |
| 2014/0147511 | A1 | 5/2014 | Tseng et al. |
| 2015/0342998 | A1 | 12/2015 | Tseng et al. |
| 2016/0120912 | A1 | 5/2016 | Tseng |

FOREIGN PATENT DOCUMENTS

| | | |
|---|---|---|
| CN | 1871019 A | 11/2006 |
| WO | WO-0180844 A2 | 11/2001 |
| WO | WO2003/097809 | 11/2003 |
| WO | WO-2008060377 A2 | 5/2008 |
| WO | WO2011/031489 | 3/2011 |
| WO | WO2012/003377 | 1/2012 |
| WO | WO2012/149486 | 11/2012 |
| WO | WO2012/170905 | 12/2012 |
| WO | WO2013/032938 | 3/2013 |
| WO | WO-2013103413 A1 | 7/2013 |
| WO | WO-2015187812 A1 | 12/2015 |
| WO | WO-2016010984 A2 | 1/2016 |
| WO | WO-2016073667 A1 | 5/2016 |
| WO | WO-2016187555 A1 | 11/2016 |

OTHER PUBLICATIONS

Yusof et al. Radiation Physics and Chemistry 76 (2007) 1756-1759.*
Gajiwala et al. Evaluation of lyophilised, gamma-irradiated amnion as a biological dressing. Cell Tissue Bank 5(2):73-80 (2004).
Co-pending U.S. Appl. No. 14/819,319, filed Aug. 5, 2015.
Nguyen et al. Sterilization of allograft bone: effects of gamma irradiations on allograft biology and biomechanics. Cell Tissue Banking 8:93-105 (2007).
Riau et al. Preservation, sterilization and de-epithelialization of human amniotic membrane for use in ocular surface reconstruction. Biomaterials 31:216-225 (2010).
Shortt et al. The effect of amniotic membrane preparation method on its ability to serve as a substrate for the ex-vivo expansion of limbal epithelial cells. Biomaterials 30:1056-1065 (2009).
Singh et al. Dried gamma-irradiation amniotic membrane as dressing in burn wound care. Journal of Tissue Viability 20:49-54 (2011).
Singh et al. Microbiological safety and clinical efficacy of radiation sterilized amniotic membranes for treatment of second-degree burns. Burns 33:505-510 (2007).
U.S. Appl. No. 14/819,319 Office Action dated Oct. 2, 2015.
PCT/US2012/052358 International Search Report and Written Opinion dated Jan. 31, 2013.

(Continued)

*Primary Examiner* — Amy L Clark
(74) *Attorney, Agent, or Firm* — Wilson Sonsini Goodrich & Rosati

(57) ABSTRACT

Disclosed herein, are methods of preparing sterilized amniotic tissues. Further disclosed herein, are methods of using the sterilized amniotic tissues.

6 Claims, 9 Drawing Sheets

(56) References Cited

OTHER PUBLICATIONS

PCT/US2012/052358 International Preliminary Report on Patentability dated Mar. 4, 2014.
Adatia et al. Correlation Between Corneal Sensitivity, Subjective Dry Eye Symptoms and Corneal Staining in Sjogren's Syndrome. Can I Ophthalmol 39:767-771 (2004).
Brophy. Gas Chromatographic Quality Control for Oil of *Melaleuca terpinen*-4-ol Type (Australian Tea Tree). J. Agric. Food Chem. 37:1330-1335 (1989).
Budavari et al. The Merck Index, Thirteenth Edition, Merck & Co., Inc., Rahway, NJ (4 pgs) (2001).
Co-pending U.S. Appl. No. 15/051,477, filed Feb. 23, 2016.
Co-pending U.S. Appl. No. 15/160,487, filed May 20, 2016.
CTFA (Cosmetic, Toiletry, and Fragrance Association) International Cosmetic Ingredient Dictionary and Handbook, 10th Ed. (2004) (abstract only).
He et al. Inhibition of Proliferation and Epithelial Mesenchymal Transition via Wnt and TGF-β Signaling Pathway in an in vitro Cell Culture Based-PVR Model by HC-HA/PTX3 Purified from Amniotic Membrane. The Association for Research in Vision and Ophthalmology (ARVO) 2016 on May 1-May 5 (Washington State Convention Center, Seattle, Washington) Abstract No. 5384-B005 (2 pgs).
Heiligenhaus et al. Improvement of HSV-1 Necrotizing Keratitis with Amniotic Membrane Transplantation Invest Ophthalmol Vis Sci 42(9):1969-1974 (2001).
Inactive Ingredient Guide, U.S. Food and Drug Administration (FDA) Center for Drug Evaluation and Research (CDER) Office of Management, http://www.accessdata.fda.gov/scripts/cder/iig/index.cfm (8 pgs.) (2012).
Kuriyan et al. A potential novel therapy for PVR: HC-HA/PTX3, an active matrix component of amniotic membrane, inhibits proliferation of rabbit RPE cells and is non-toxic intravitreally. The Association for Research in Vision and Ophthalmology (ARVO) 2015 meeting on May 3-May 7 (Colorado Convention Center Denver, CO) Abstract No. 1126-B029 (2 pgs).
Kuriyan et al. HC-HA/PTX3, an active matrix component of amniotic membrane, inhibits proliferation and epithelial mesenchymal transition of RPE cells: a potential novel therapy for PVR. The Association for Research in Vision and Ophthalmology (ARVO) 2015 meeting on May 3-May 7 (Colorado Convention Center Denver, CO) Abstract No. 2287-B0192 (2 pgs).
Lee et al. Amniotic Membrane Transplantation for Persistent Epithelial Defects with Ulceration. Am. J. Ophthalmol. 123:303-312 (1997).
Lee et al. An Agarose Gel Electrophoretic Method for Analysis of Hyaluronan Molecular Weight Distribution. Anal. Biochem. 219:278-287 (1994).
Merck Manuals Online Medical Library, Age-Related Macular Degeneration (ARMD), originally printed Aug. 13, 2008/reprinted 2016 from http://www.merck.com/mmpe/print/sec09/ch106/ch106b.html (9 pgs.).
Mondello et al. In vivo activity of terpenin-4-ol, the main bioactive component of *Melaleuca alternifolia* Cheel (tea tree) oil against azole-susceptible and -resistant human pathogenic *Candida* species. BMC Infectious Diseases 6:158 (2006).
PCT/US2015/033955 International Search Report and Written Opinion dated Aug. 19, 2015.
PCT/US2015/059142 International Search Report and Written Opinion dated Jan. 19, 2016.
Prabhasawat et al. Comparison of Conjunctival Autografts, Amniotic Membrane Grafts, and Primary Closure for Pterygium Excision. Ophthalmology 104:974-985 (1997).
Rennie et al. Applications of Amniotic Membrane and Fluid in Stem Cell Biology and Regenerative Medicine. Stem Cells International (ID 721538):1-13 (2012).
Tan et al. Structural and Biological Comparison of Cryopreserved and Fresh Amniotic membrane Tissues. Journal Biomaterial and Tissue Engineering 4:379-388 (2014).
Trommer et al. Overcoming the Stratum Corneum: Modulation of Skin Penetration. A review. Skin Pharmacol Physiol 19(2):106-121 (2006).
Tseng et al. Amniotic Membrane Transplantation with or without Limbal Transplantation for Corneal Surface Reconstruction in Patients with Limbal Stem Cell Deficiency. Arch Ophthalmol. 116:431-441(Apr. 1998).
Lee et al. Adhesion between Amniotic Membrane and Retinal Tissue and Inhibition of Amniotic Membrane on Cell Transformation. J Korean Ophthalmol Soc. 44(2):459-471 (2003) (Abstract Only).
PCT/US2015/033955 International Preliminary Report on Patentability dated Dec. 15, 2016.
PCT/US2016/033558 International Search Report and Written Opinion dated Oct. 25, 2016.
U.S. Appl. No. 14/729,489 Office Action dated Dec. 7, 2016.
Zhang et al. Constitutive Expression of Pentraxin 3 (PTX3) Protein by Human Amniotic Membrane Cells Leads to Formation of the Heavy Chain (HC)-Hyaluronan (HA)-PTX3 Complex. J Biol Chem 289(19):13531-13542 (2014).
Dua et al. The Amniotic Membrane in Ophthalmology. Surv Ophthalmol 49(1):51-77 (2004).
PCT/US2015/059142 International Preliminary Report on Patentability dated May 18, 2017.
PCT/US2017/015325 International Search Report and Written Opinion dated Jun. 9, 2017.
Schroeder et al. Effects of the human amniotic membrane on axonal outgrowth of dorsal root ganglia neurons in culture. Curr Eye Res 32:731-738 (2007).
U.S. Appl. No. 14/933,106 Office Action dated Jul. 10, 2017.
U.S. Appl. No. 14/819,319 Office Action dated Apr. 1, 2016.

* cited by examiner

METHODS OF STERILIZING FETAL SUPPORT TISSUES

CROSS REFERENCE

This application is the National Stage Entry of International Application No. PCT/US2012/052358, filed Aug. 24, 2012, which claims the benefit of and right of priority to U.S. Provisional Application No. 61/528,059, filed Aug. 26, 2011, both of which are incorporated herein by reference in their entireties.

BACKGROUND OF THE INVENTION

The placenta is a temporary organ that surrounds the fetus during gestation. The placenta allows for transport of gases and nutrients, and also provides other metabolic and endocrine functions. The amniotic membrane (AM) is an avascular membranous sac that is filled with amniotic fluid. The AM is the innermost membrane surrounding a fetus in the amniotic cavity. AM also forms the outer layer of the umbilical cord, which connects the placenta to the fetus and transports oxygen to the fetus. Wharton's jelly, a specialized gelatinous connective tissue material, surrounds the umbilical cord to protect it from damage during fetal movement and development. The AM tissue consists of an epithelial layer and a subjacent avascular stromal layer. The chorion surrounds the amniotic membrane. The chorion consists of two layers: an outer layer formed by the trophoblast, and an inner layer formed by the somatic mesoderm; the amnion is in contact with the latter. The trophoblast is made up of an internal layer of cubical or prismatic cells, the cytotrophoblast or layer of Langhans, and an external layer of richly nucleated protoplasm devoid of cell boundaries, the syncytiotrophoblast.

SUMMARY OF THE INVENTION

Described herein, in certain embodiments is a sterilized fetal support tissue product, wherein the biological activity of the fetal support tissue product is maintained. In some embodiments, the fetal support tissue product is exposed to γ-irradiation for a period of time sufficient to sterilize the fetal support tissue product. In some embodiments, the fetal support tissue product is exposed to γ-irradiation for about 1 minute, 5 minutes, 10 minutes, 20 minutes, 30 minutes, 40 minutes, 50 minutes, or 1 hour. In some embodiments, the fetal support tissue product is frozen prior to exposure to γ-irradiation. In some embodiments, the fetal support tissue product is frozen at about 0° C., −5° C., −10° C., −20° C., −40° C., −50° C., −60° C., −70° C., or −80° C. In some embodiments, the fetal support tissue product is exposed to γ-irradiation at a temperature of about 0° C., −5° C., −10° C., −20° C., −40° C., −50° C., −60° C., −70° C., or −80° C. In some embodiments, the sterilized fetal support tissue product has a Sterility Assurance Level (SAL) of $10^{-6}$ for the sterilized fetal support tissue product. In some embodiments, the structural integrity of the fetal support tissue product is maintained. In some embodiments, the sterilized fetal support tissue product is stable at room temperature for 1 month, 2 months, 3 months, 4 months, 5 months, 6 months, 7 months, 8 months, 9 months, 10 months, 11, months, 1 year, 2 years 3 years, 4 years or 5 years. In some embodiments, the sterilized fetal support tissue product further comprises a radioprotective composition. In some embodiments, the sterilized fetal support tissue product further comprises is radioprotective composition comprising glycerol or propylene glycol, or a combination thereof. In some embodiments, the sterilized fetal support tissue product sterilized fetal support tissue product is inhibits or reduces inflammation, inhibits or reduces scarring inhibits or reduces angiogenesis, inhibits or reduces adhesion, or promotes wound healing.

Described herein, in certain embodiments is a sterilized fetal support tissue product produced by a process comprising: exposing a radioprotected fetal support tissue product to γ-irradiation at a dosage effective to sterilize the fetal support tissue product, wherein the fetal support tissue product is radioprotected with a radioprotective composition comprising glycerol, propylene glycol, or a combination thereof. In some embodiments, the fetal support tissue product is exposed to γ-irradiation for a period of time sufficient to sterilize the fetal support tissue product. In some embodiments, the period of time is about 1 minute, 5 minutes, 10 minutes, 20 minutes, 30 minutes, 40 minutes, 50 minutes, or 1 hour. In some embodiments, the fetal support tissue product is frozen prior to exposure to γ-irradiation. In some embodiments, the fetal support tissue product is frozen at about 0° C., −5° C., −10° C., −20° C., −40° C., −50° C., −60° C., −70° C., or −80° C. In some embodiments, the fetal support tissue product is exposed to γ-irradiation at about 0° C., −5° C., −10° C., −20° C., −40° C., −50° C., −60° C., −70° C., or −80° C. In some embodiments, the fetal support tissue product is exposed to γ-irradiation on dry ice. In some embodiments, sterilization results in a Sterility Assurance Level (SAL) of $10^{-6}$ for the sterilized fetal support tissue product. In some embodiments, the biological activity of the fetal support tissue product is maintained. In some embodiments, the structural integrity of the fetal support tissue product is maintained. In some embodiments, the sterilized fetal support tissue product is stable at room temperature for 1 month, 2 months, 3 months, 4 months, 5 months, 6 months, 7 months, 8 months, 9 months, 10 months, 11, months, 1 year, 2 years 3 years, 4 years or 5 years. In some embodiments, the sterilized fetal support tissue product further comprises a radioprotective composition. In some embodiments, the sterilized fetal support tissue product further comprises is radioprotective composition comprising glycerol or propylene glycol, or a combination thereof. In some embodiments, the sterilized fetal support tissue product sterilized fetal support tissue product is inhibits or reduces inflammation, inhibits or reduces scarring inhibits or reduces angiogenesis, inhibits or reduces adhesion, or promotes wound healing.

Described herein, in certain embodiments, is a method of sterilizing a fetal support tissue product, comprising: exposing a radioprotected fetal support tissue product to γ-irradiation at a dosage effective to sterilize the fetal support tissue product, wherein the fetal support tissue product is radioprotected with a radioprotective composition comprising glycerol, propylene glycol, or a combination thereof. In some embodiments, the fetal support tissue product is exposed to γ-irradiation for a period of time sufficient to sterilize the fetal support tissue product. In some embodiments, the period of time is about 1 minute, 5 minutes, 10 minutes, 20 minutes, 30 minutes, 40 minutes, 50 minutes, or 1 hour. In some embodiments, the method further comprises a step of contacting the fetal support tissue product with the radioprotective composition for a predetermined period of time. In some embodiments, the fetal support tissue product is contacted with the radioprotective composition for 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, or 24 hours. In some embodiments, the method further comprises a step of freezing the radioprotected fetal support tissue product prior to exposure to γ-irradiation. In some embodiments, the fetal support tissue product is frozen at about 0° C., −5° C., −10° C., −20° C., −40° C., −50° C., −60° C., −70° C., or −80° C. In some embodiments, the fetal support tissue product is exposed to γ-irradiation at about 0° C., −5° C., −10° C., −20° C., −40° C., −50° C., −60° C., −70° C., or −80° C. In some embodiments, the fetal support tissue product is exposed to γ-irradiation on dry ice. In some embodiments, sterilization results in a Sterility Assurance Level (SAL) of $10^{-6}$ for the sterilized fetal support tissue product. In some embodiments, the biological activity of the fetal support tissue product is maintained. In some embodiments, the structural integrity of the fetal support tissue product is maintained. In some embodiments, the sterilized fetal support tissue product is stable at room temperature for 1 month, 2 months, 3 months, 4 months, 5 months, 6 months, 7 months, 8 months, 9 months, 10 months, 11, months, 1 year, 2 years, 3 years, 4 years or 5 years. In some embodiments, the radioprotective composition is a cryoprotective composition.

Disclosed herein, in certain embodiments, is a radioprotective composition. In some embodiments of the methods provided herein, the radioprotective composition is a solution. In some embodiments, the radioprotective composition comprises about 30% to about 70% glycerol. In some embodiments, the radioprotective composition comprises about 50% glycerol. In some embodiments, the radioprotective composition comprises about 1% to about 30% propylene glycol. In some embodiments, the radioprotective composition comprises about 10% propylene glycol. In some embodiments, a fetal support tissue product is contacted with the radioprotective composition for a period of time sufficient to maintain the biological activity of the fetal support tissue product from exposure to γ-irradiation. In some embodiments, a fetal support tissue product is contacted with the radioprotective composition for a period of time sufficient to maintain the structural integrity of the fetal support tissue product from exposure to γ-irradiation. In some embodiments, a fetal support tissue product is contacted with the radioprotective composition at 4° C. In some embodiments, the radioprotective composition further comprises trehalose, DMSO, or a combination thereof. In some embodiments, a fetal support tissue product is contacted with the radioprotective composition as a storage media.

In some embodiments of the methods provided herein, the fetal support tissue product is exposed to γ-irradiation after being dispensed into a container. In some embodiments, the fetal support tissue product is exposed to γ-irradiation after being dispensed into a container suitable of maintaining the sterility of the fetal support tissue product.

In some embodiments of the methods provided herein, the dose range of the γ-irradiation is between 10 kGy and 60 kGy. In some embodiments, the dose range of the γ-irradiation is between 17 kGy and 30 kGy. In some embodiments, the dose range of the γ-irradiation is between 17 kGy and 20 kGy. In some embodiments, the dose range of the γ-irradiation is between 20 kGy and 24 kGy. In some embodiments, the dose range of the γ-irradiation is between 25 kGy and 30 kGy. In some embodiments, the fetal support tissue product is radioprotected by exposure to the radioprotectant.

In some embodiments of the methods provided herein, the radioprotected fetal support tissue product is lyophilized prior to exposure to γ-irradiation. In some embodiments, about 10%, 20%, 30%, 40%, 50%, 60%, 70%, 80%, 90%, 95%, 96%, 97%, 98%, 99% of the water content of the radioprotected fetal support tissue product is removed by lyophilization. In some embodiments, the radioprotected fetal support tissue product is lyophilized at or below 0° C. In some embodiments of the methods provided herein, the fetal support tissue product is not lyophilized prior to exposure to γ-irradiation.

In some embodiments of the methods provided herein, the fetal support tissue product is derived from placental amniotic membrane, umbilical cord amniotic membrane, chorion, amnion-chorion, placenta, umbilical cord, or any combination thereof. In some embodiments, the fetal support tissue product is a tissue graft. In some embodiments, the fetal support tissue product is in the form of a powder.

In some embodiments of the methods provided herein, the sterilized fetal support tissue product is stored at room temperature. In some embodiments of the method provided herein, the sterilized fetal support tissue product is shipped at room temperature.

In some embodiments of the methods provided herein, the fetal support tissue product is made by a process comprising: first, obtaining a placental tissue comprising amniotic membrane, chorion, amnion-chorion, umbilical cord, placenta, or any combination thereof; and second, washing the placental tissue to remove the blood from the placental tissue. In some embodiments, the method further comprises isolating the amniotic membrane from the placental tissue. In some embodiments, the method further comprises isolating the umbilical cord from the placental tissue. In some embodiments, the method further comprises isolating the chorion from the placental tissue. In some embodiments, the method further comprises isolating the amnion-chorion from the placental tissue.

In some embodiments of the methods provided herein, the method further comprises contacting the fetal support tissue product with a substrate. In some embodiments, the substrate selected from a membrane, a bandage, or a wound dressing.

In some embodiments of the methods provided herein, the method further comprises contacting the fetal support tissue product with a polyethersulfone (PES) membrane, a nitrocellulose membrane, or a nylon membrane.

Described herein, in certain embodiments, is a sterilized fetal support tissue product made by any of the methods provided herein. In some embodiments the sterilized fetal support tissue product is inhibits or reduces inflammation, inhibits or reduces scarring inhibits or reduces angiogenesis, inhibits or reduces adhesion, or promotes wound healing.

Described herein, in certain embodiments, is a method of treating a wound in an individual in need thereof, comprising administering the sterilized fetal support tissue product provided herein to the wound for a period of time sufficient to treat the wound. In some embodiments, the wound is a burn, or an ulcer. In some embodiments, the ulcer is a foot ulcer, diabetic ulcer or a venous ulcer. In some embodiments, the sterilized fetal support tissue product is a wound covering.

Described herein, in certain embodiments, is a method of treating a spinal condition in an individual in need thereof, comprising administering the sterilized fetal support tissue product provided herein to the individual for a period of time sufficient to treat the spinal condition. In some embodiments the spinal condition is selected from a herniated disc, spinal adhesion, discitis, degenerative/painful disc, irritated/inflamed neural/sciatic pathway, facet/scaroiliac pain, vertebral fracture, exposed neural structure on bony defects, additive to cage or lateral gutter, and combination thereof.

Described herein, in certain embodiments, is a method of treating an arthritic condition in an individual in need thereof, comprising administering the sterilized fetal support tissue product provided herein to the individual for a period of time sufficient to treat the arthritic condition. In some embodiments, the arthritic condition is selected from osteoarthritis, rheumatoid arthritis, septic arthritis, ankylosing spondylitis, and spondylosis.

Described herein, in certain embodiments, is a method of regenerating or repairing nerve, bone, tendon, tissue or cartilage in an individual in need thereof, comprising administering the sterilized fetal support tissue product provided herein to the individual for a period of time sufficient to regenerate or repair the nerve, bone, tendon, tissue or cartilage. In some embodiments, the individual has a disorder selected from: osteochondral defects, Arthritis, Trigger Finger, Carpal Tunnel Syndrome, Wrist Tendonitis, Tennis Elbow, Golfer's Elbow, Impingement Syndrome, Shoulder Bursitis, Snapping Hip Syndrome, Hip Bursitis, Stress Fractures, Shin Splints, Chonromalacia, Achilles Tendonities, Tarsal Tunnel Syndrome, Posterior Tibial Tendonitis, or a combination thereof.

Described herein, in certain embodiments, is a method of supplementing tissue, comprising injecting the sterilized fetal support tissue product provided herein into a tissue in need of supplementation. In some embodiments, the sterilized fetal support tissue product is a dermal filler.

Described herein, in certain embodiments, is a method of treating an ophthalmic disorder in an individual in need thereof, comprising administering the sterilized fetal support tissue product provided herein to the individual for a period of time sufficient to treat the ophthalmic disorder. In some embodiments, the ophthalmic disorder is a wound or dry eye.

Described herein, in certain embodiments, is a use of the sterilized fetal support tissue product provided herein as a wound covering, adhesion barrier, or a dermal filler.

Described herein, in certain embodiments, is a use of the sterilized fetal support tissue product provided herein as a tendon wrapping or nerve wrapping.

Described herein, in certain embodiments, is a use of the sterilized fetal support tissue product provided herein to inhibit or reverse scar formation, inflammation, adhesion, or undesired angiogenesis.

Described herein, in certain embodiments, is a sterilized fetal support tissue product that is sterilized by γ-irradiation and has at least 49% epithelial, stroma and basement membrane layers of the fetal support tissue intact compared to the non-irradiated fetal support tissue product. In some embodiments, the sterilized fetal support tissue product comprises a radioprotective composition. In some embodiments, the radioprotective composition comprises glycerol or propylene glycol.

Described herein, in certain embodiments, is a sterilized fetal support tissue product that is sterilized by γ-irradiation and has at least 10%, 15%, 20%, 25%, 30%, 35%, 40%, 45%, 50%, 55%, 60%, 65%, 70%, 75%, 80%, 85%, 90%, 95% activity compared to the non-irradiated fetal support tissue product. In some embodiments, the sterilized fetal support tissue product comprises a radioprotective composition. In some embodiments, the radioprotective composition comprises glycerol or propylene glycol.

Described herein, in certain embodiments, is a sterilized fetal support tissue product that is sterilized by γ-irradiation and stable at room temperature for 1 month, 2 months, 3 months, 4 months, 5 months, 6 months, 7 months, 8 months, 9 months, 10 months, 11, months, 1 year, 2 years 3 years, 4 years, 5 years. In some embodiments, the sterilized fetal support tissue product comprises a radioprotective composition. In some embodiments, the radioprotective composition comprises glycerol or propylene glycol.

Described herein, in certain embodiments, is an improved method of sterilizing a fetal support tissue product comprising exposing a fetal support tissue product to γ-irradiation at a dosage sufficient to sterilize the fetal support tissue product, the improvement comprising: radioprotecting the fetal support tissue product with a radioprotective composition comprises glycerol, propylene glycol, or a combination thereof. In some embodiments, the improvement further comprises freezing the radioprotected fetal support tissue product prior to exposure to γ-irradiation. In some embodiments, the improvement further comprises irradiating the fetal support tissue product at frozen temperature. In some embodiments, the fetal support tissue product is exposed to γ-irradiation on dry ice.

BRIEF DESCRIPTION OF THE DRAWINGS

The novel features of the invention are set forth with particularity in the appended claims. a better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Certain Terminology

Figure 1:
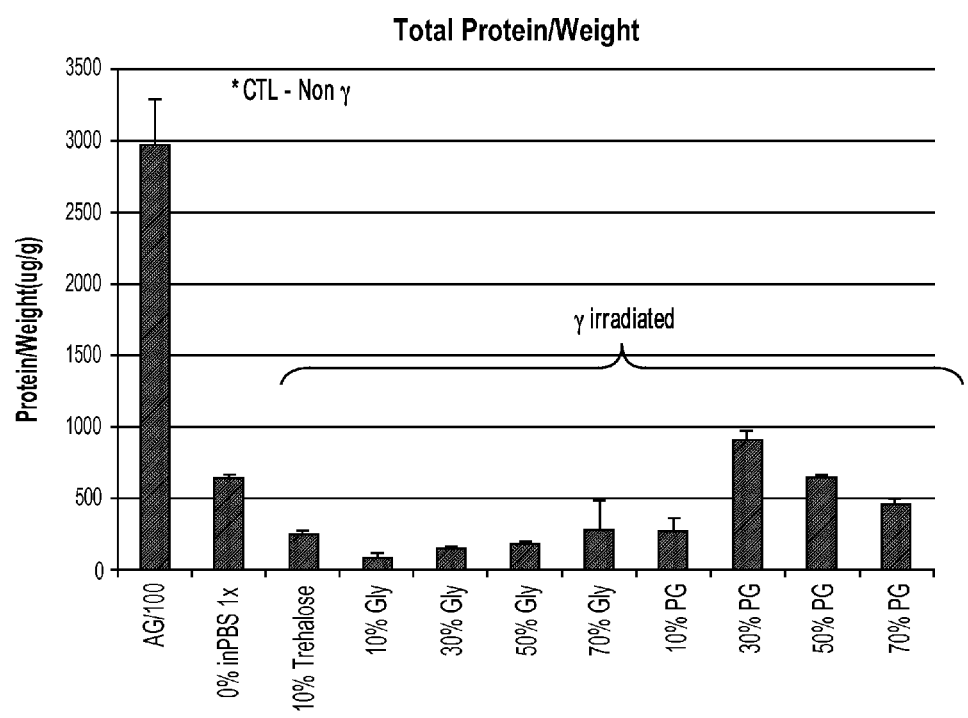
FIG. 1 exemplifies total protein extracted per weight in γ-irradiated AM samples (irradiated at RT) compared to the non γ-irradiated control.

As used herein, "fetal support tissue product" means any isolated product derived from tissue used to support the development of a fetus. Examples fetal support tissue products include, but are not limited to, (i) placental amniotic membrane (PAM), or substantially isolated PAM, (ii) umbilical cord amniotic membrane (UCAM) or substantially isolated UCAM, (iii) chorion or substantially isolated chorion, (iv) amnion-chorion or substantially isolated amnion-chorion, (v) placenta or substantially isolated placenta, (vi) umbilical cord or substantially isolated umbilical cord, or (vii) any combinations thereof. Fetal support tissue products include any form of the fetal support tissue, including lyophilized fetal support tissue or powders resulting from grinding fetal support tissue.

As used herein, a "radioprotected fetal support tissue product" refers to a fetal support tissue product contacted and a radioprotective composition.

As used herein, the phrase "maintains structural integrity" with respect to a sterilized fetal support tissue product described herein means that that the epithelial, stroma and basement membrane of the fetal support tissue remains intact following exposure to γ-irradiation as compared to a non-irradiated fetal support tissue product. Generally, a sterilized fetal support tissue product is said to maintain structural integrity if greater than 49% epithelial, stroma and basement membrane layers of the fetal support tissue remains intact compared to a non-irradiated fetal support tissue product. Where the fetal support tissue product comprises amniotic membrane, in some embodiments, the AM epithelium is present in the sterilized fetal support tissue product as assessed by Hematoxylin and Eosin staining Where the fetal support tissue product comprises amniotic membrane, in some embodiments, the AM basement membrane is present in the sterilized fetal support tissue product as assessed by Alcian Blue staining. Where the fetal support tissue product comprises amniotic membrane, in some embodiments, the AM stroma is present in the sterilized fetal support tissue product as assessed by Periodic Acid-Schiff Reaction (PAS) staining.

As used herein, the phrase "maintains biological activity" with respect to a sterilized fetal support tissue product disclosed herein means that that the sterilized fetal support tissue product maintains at least one biological activity of the fetal support tissue product following exposure to γ-irradiation as compared to a non-irradiated fetal support tissue product. Generally, a sterilized fetal support tissue product is said to maintain at least one biological activity if the sterilized fetal support tissue maintains at least 10%, 15%, 20%, 25%, 30%, 35%, 40%, 45%, 50%, 55%, 60%, 65%, 70%, 75%, 80%, 85%, 90%, 95%, or greater of that biological activity as compared to a non-irradiated fetal support tissue product. In some embodiments, a sterilized fetal support tissue product disclosed herein maintains substantially all biological activity as compared to a non-irradiated fetal support tissue product. Exemplary activities a fetal support tissue product include but are not limited to inhibiting or reducing inflammation, inhibiting or reducing scarring, inhibiting or reducing angiogenesis, inhibiting or reducing adhesion, and promoting wound healing.

As used herein, a radiation dosage refers to the amount of radiation delivered. Radiation dosage is calculated as the rate of radiation multiplied by the length of time the product is exposed to γ-irradiation.

As used herein, "placental amniotic membrane" (PAM) means amniotic membrane derived from the placenta. In some embodiments, the PAM is substantially isolated.

As used herein, "umbilical cord amniotic membrane" (UCAM) means amniotic membrane derived from the umbilical cord. UCAM is a translucent membrane. The UCAM has multiple layers: an epithelial layer; a basement membrane; a compact layer; a fibroblast layer; and a spongy layer. It lacks blood vessels or a direct blood supply. In some embodiments, the UCAM is substantially isolated. In some embodiments, the UCAM comprises Wharton's Jelly. In some embodiments, the UCAM comprises blood vessels and/or arteries. In some embodiments, the UCAM comprises Wharton's Jelly and blood vessels and/or arteries.

As used herein, "umbilical cord" means the organ that connects a developing fetus to the placenta. The umbilical cord is composed of Wharton's jelly, a gelatinous substance made largely from mucopolysaccharides. It comprises one vein, which carries oxygenated, nutrient-rich blood to the fetus, and two arteries that carry deoxygenated, nutrient-depleted blood away.

As used herein, "placenta" means the organ that connects a developing fetus to the maternal uterine wall to allow nutrient uptake, waste elimination, and gas exchange via the maternal blood supply. The placenta is composed of three layers. The innermost placental layer surrounding the fetus is called amnion. The allantois is the middle layer of the placenta (derived from the embryonic hindgut); blood vessels originating from the umbilicus traverse this membrane. The outermost layer of the placenta, the chorion, comes into contact with the endometrium. The chorion and allantois fuse to form the chorioallantoic membrane.

As used herein, "chorion" means the membrane formed by extraembryonic mesoderm and the two layers of trophoblast. The chorionic villi emerge from the chorion, invade the endometrium, and allow transfer of nutrients from maternal blood to fetal blood. The chorion consists of two layers: an outer layer formed by the trophoblast, and an inner layer formed by the somatic mesoderm; the amnion is in contact with the latter. The trophoblast is made up of an internal layer of cubical or prismatic cells, the cytotrophoblast or layer of Langhans, and an external layer of richly nucleated protoplasm devoid of cell boundaries, the syncytiotrophoblast. The avascular amnion is adherent to the inner layer of the chorion.

As used herein, "amnion-chorion" means a product comprising amnion and chorion. In some embodiments, the amnion and the chorion are not separated (i.e., the amnion is naturally adherent to the inner layer of the chorion). In some embodiments, the amnion is initially separated from the chorion and later combined with the chorion during processing.

"Substantially isolated" or "isolated" means that the fetal support tissue product has been separate from undesired materials (e.g., red blood cells, blood vessels, and arteries) derived from the original source organism. Purity, or "isolation" may be assayed by standard methods, and will ordinarily be at least about 10% pure, more ordinarily at least about 20% pure, generally at least about 30% pure, and more generally at least about 40% pure; in further embodiments at least about 50% pure, or more often at least about 60% pure; in still other embodiments, at least about 95% pure.

As used herein, "biological activity" means the activity of polypeptides and polysaccharides. In some embodiments, the activity of polypeptides and polysaccharides found in umbilical cord (and substantially isolated umbilical cord), UCAM (and substantially isolated UCAM), placenta (and substantially isolated placenta), PAM (and substantially isolated PAM), chorion (and substantially isolated chorion), or amnion-chorion (and substantially isolated amnion-chorion).

As used herein, the substantial preservation of biological activity or structural integrity means that when compared to the biological activity and structural integrity of non-processed tissue, the biological activity and structural integrity of the fetal support tissue product has only decreased by about 5%, about 10%, about 15%, about 20%, about 25%, about 30%, about 35%, about 40%, about 50%, or about 60%.

As used herein, "freezing" refers to exposing the fetal support tissue product below about or at 0° C., −5° C., −10° C., −20° C., −40° C., −50° C., −60° C., −70° C., −80° C., −90° C., or −100° C. for a period of time of about 1 hour, 2 hours, 3 hours, 4 hours, 5 hours, 6 hours, 7 hours, 8 hours, 9 hours, 10 hours, 11 hours, 12 hours, 18 hours, 24 hours, or longer.

As used herein, "powder" means matter in the form of fine dry particles or matrix. In some embodiments, the particles are not uniform in size. In some embodiments, the particles are substantially uniform in size.

As used herein, "grinding" means any method of reducing fetal support tissue to small particles or a powder. The term grinding includes micronizing, pulverizing, homogenizing, filing, milling, grating, pounding, and crushing.

The term "fresh" refers to tissue that is less than 24 hours old following birth, and which is in substantially the same form as it was following birth.

The terms "subject" and "individual" are used interchangeably. as used herein, both terms mean any animal, preferably a mammal, including a human or non-human. The terms patient, subject, and individual are used interchangeably. None of the terms are to be interpreted as requiring the supervision of a medical professional (e.g., a doctor, nurse, physician's assistant, orderly, hospice worker).

The terms "treat," "treating" or "treatment," as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Overview of Sterilization

Amniotic membrane (AM) modulates adult wound healing and facilitates tissue regeneration. In certain instances, AM promotes epithelialization while suppressing stromal inflammation, angiogenesis and scarring. AM has been used successfully as a surgical graft or temporary biological patch for the treatment of ophthalmic conditions which require corneal and conjunctival surface reconstruction, including, but not limited to, persistent epithelial defect, deep corneal ulcer, infectious keratitis, symptomatic bullous keratopathy, acute Stevens Johnson Syndrome/Toxic Epidermal Necrolysis (SJS/TEN), limbal stem cell deficiency, pterygium, pinguecula, conjunctivochalasis, symblepharon, formix reconstruction, and conjunctival tumors.

Different preservation methods employed in the preparation of a fetal support tissue product, such as cryopreservation, lyophilization and exposure to γ-irradiation, result in changes in the properties of the AM, which in turn affects the clinical outcome of AM transplantation. as described herein, methods to assess AM properties, such as biological, biophysical, biochemical and histological properties, are employed to ascertain the effects of different preservation methods.

The fetal support tissue product currently indicated for transplantation in ophthalmic surgery is categorized into two forms, "wet" and "dry". Handling processes of AM that result in a "wet" AM include processing in isotonic solutions and cryopreservation. The "dry" form of AM results from a variety of preservation methods that include processing in different non-isotonic solutions, air-drying, lyophilization (freeze drying), dehydration in an incubator or oven, and silica gel desiccation. a comparison of different preservation methods, Cryo-AM, CryoDMSO-AM, Lyo-AM, AD-AM and SG-AM, is shown in Table 1.

TABLE 1

Amniotic Membrane (AM) Preservation Methods

| | | Wet | | Dry | |
|---|---|---|---|---|---|
| | | Cryopreservation in DMSO (CryoDMSO-AM) | | | |
| Amniotic Membrane Preparation Methods/Processing Steps | Cryo-preservation (Cryo-AM) Lee et al. (1997) *Am J Ophthalmol.* 123: 303-312 | Azuara-Blanco et al. (1999) *Br J Ophthalmol.* 8339: 399-402 or Kubo et al. (2001) *Invest Ophthalmol Vis Sci.* 42: 1539-1546 | Lyophilization (Lyo-AM) Nakamura et al. (2008) *Biomaterials* 29: 3729-3737 | Air-Drying (AD-AM) Singh et al. (2003) *Cell Tissue Bank* 4: 95-100 | Silica Gel Dessication (SG-AM) Miljudin E et al. (2004) *Cell Tissue Bank* 5: 271-275 |
| 1. Thawing, Washing & Separation of Amnion | Washed with Earle's balanced saline | Washed with PBS followed by 0.56M, 1.12M & 1.41M in PBS for 5 min each (Azuara-Blanco) or Washed with saline followed by 0.5M 1.0M & 1.5M in DMSO for 5 min each (Kubo) | Washed in PBS; Removal of HAEC by 0.02% (0.589 mM) EDTA in unknown solution at 37° C. for 2 hrs; Incubated with 0.10% Trehalose solution at 37° C. for 2 hrs | Washed with saline followed by NaClO and distilled water | Washed in antiseptics |

TABLE 1-continued

Amniotic Membrane (AM) Preservation Methods

| | Wet | | | Dry | |
|---|---|---|---|---|---|
| | | Cryopreservation in DMSO (CryoDMSO-AM) | | | |
| Amniotic Membrane Preparation Methods/Processing Steps | Cryo-preservation (Cryo-AM) Lee et al. (1997) *Am J Ophthalmol.* 123: 303-312 | Azuara-Blanco et al. (1999) *Br J Ophthalmol.* 8339: 399-402 or Kubo et al. (2001) *Invest Ophthalmol Vis Sci.* 42: 1539-1546 | Lyophilization (Lyo-AM) Nakamura et al. (2008) *Biomaterials* 29: 3729-3737 | Air-Drying (AD-AM) Singh et al. (2003) *Cell Tissue Bank* 4: 95-100 | Silica Gel Dessication (SG-AM) Miljudin E et al. (2004) *Cell Tissue Bank* 5: 271-275 |
| 2. Backing Material | Nitrocellulose Paper | Nitrocellulose Paper | N/A | N/A | N/A |
| 3. Storing Solution | DMEM/glycerol (1:1) | 10% DMSO | N/A | N/A | Glycerol |
| 4. Freezing/ Drying | −80° C. | −70° C. (Azuara-Blanco) or −80° C. (Kubo)) | Freeze drying under vacuum conditions | Dried in RT air from laminar flow cabinet | Drying over silica gel on frames |
| Sterilization by γ-irradiation | — | — | 20 kGy | 25 kGy | γ-irradiation (N/A) |

Abbr:
DMEM—Dulbecco's Modified Eagle's Medium,
DMSO—Dimethyl sulfoxide,
EDTA—Ethylene Diamine Teraacetic Acid,
PAA—Peracetic Acid,
PES—Peracetic Acid-Ethanol Sterilization,
N/A—Not Available)

Cryopreservation appears to be the better preservation method in terms of retaining the biological, biochemical and histological function of the AM compared with other methods (Table 1). Lyophilization is an alternative method of resolving the storage and transportation and sterilization challenges of cryopreservation. However, it remains a concern that Lyo-AM possesses relatively low protein amounts and growth factors compared to Cryo-AM. Noting that there is a wide variation of growth factors and other proteins among placenta donors, it is important that these elements remain preserved as further processing and sterilization by exposure to γ-irradiation decreases protein content.

As described herein, preservation of the protein content and active components of a fetal support tissue product is improved by the addition of protective agents such as glycerol, propylene glycol and DMSO. as shown in the Examples provided pre-incubation of the fetal support tissue product in a high concentration of glycerol (e.g., ranging from about 30%-70%) or a low concentration of propylene glycol (e.g., ranging from about 10%-30%) best protected AM against radiation damage as assessed by total protein, HA and other active ingredients extracted from the tissue as well as histology and biological activity.

The methods provided herein for terminal sterilization of a fetal support tissue product allow for the room temperature storage of the fetal support tissue product. The methods provided herein for terminal sterilization of a fetal support tissue product also allow for the shipping of the fetal support tissue product at room temperature. In some embodiments, the sterilized fetal support tissue product is the sterilized fetal support tissue product is stable at room temperature for 1 month, 2 months, 3 months, 4 months, 5 months, 6 months, 7 months, 8 months, 9 months, 10 months, 11, months, 1 year, 2 years 3 years, 4 years, 5 years or longer. In some embodiment, the sterilized fetal support tissue product is stable at room temperature for at least 1 year. In some embodiment, the sterilized fetal support tissue product is stable at room temperature for at least 2 years. In some embodiment, the sterilized fetal support tissue product is stable at room temperature for at least 3 years. In some embodiment, the sterilized fetal support tissue product is stable at room temperature for at least 4 years. In some embodiment, the sterilized fetal support tissue product is stable at room temperature for at least 4 years.

Provided herein are improved methods for the preparation and sterilization of fetal support tissue products with or without lyophilization including the addition of agents which serve as cryoprotectants and/or radioprotectants. Provided herein are improved methods for the preparation and sterilization of fetal support tissue products with or without lyophilization including the addition of agents which serve as cryoprotectants and/or radioprotectants and freezing of the radioprotected fetal support tissue product before and/or during exposure to γ-irradiation. The methods of sterilization provided herein are effective in protecting the active ingredient of AM and reducing the destruction of the protein and growth factors during the lyophilization process and terminal sterilization using γ-irradiation. The methods of sterilization provided herein are effective in maintain the biological activity and structural integrity of the fetal support tissue product during and following γ-irradiation.

Methods for the Preparation and Sterilization of Fetal Support Tissue Products

Provided herein are methods for the preparation and sterilization of a fetal support tissue product. The methods provided herein reduce the level of one or more active biological contaminants or pathogens, such as, for example, viruses, bacteria, yeasts, molds, fungi, spores, or prions in a prepared fetal support tissue product. The methods provided herein provide a sterilized fetal support tissue product with a sterility assurance level (SAL) of at least $10^{-6}$.

The methods provided herein comprise contacting the fetal support tissue product with a radioprotective composition (RPC) (i.e. the solution preserves the biological activity of the fetal support tissue product during radiation and may also preserve the structural integrity of the fetal support tissue) prior to sterilization of the product by exposure to γ-irradiation. In some embodiments, the radioprotecting agent also is a cryoprotective composition (CPC) (i.e. preserves the structural integrity and biological activity of the fetal support tissue product during freezing). In some embodiments, the method comprises contacting the fetal support tissue product with a radioprotective composition (RPA) and a cryoprotective composition (CPC).

In some embodiments, a method of sterilizing a fetal support tissue product comprises (a) contacting the fetal support tissue product with a radioprotective composition (RPC) to generate a radioprotected fetal support tissue product, and (b) exposing the radioprotected fetal support tissue product to radiation to sterilize the fetal support tissue product. In some embodiments, the radiation is γ-radiation. In some embodiments, a method of sterilizing a fetal support tissue product comprises (a) contacting the fetal support tissue product with a radioprotective composition (RPC) to generate a radioprotected fetal support tissue product, and (b) exposing the radioprotected fetal support tissue product to γ-irradiation at a dosage sufficient to sterilize the fetal support tissue product.

In some embodiments, the radioprotected fetal support tissue product is exposed to γ-irradiation at a dosage sufficient to sterilize the fetal support tissue product. In some embodiments, the radioprotected fetal support tissue product is exposed to γ-irradiation at a dosage sufficient to sterilize the fetal support tissue product according pursuant to ISO 11137, ISO 11737 or AAMI TIR 33 standard. In some embodiments, the radioprotected fetal support tissue product is exposed to γ-irradiation for a period of time sufficient to sterilize the fetal support tissue product and at a dosage effective to sterilize the fetal support tissue product. In some embodiments, a method of sterilizing a fetal support tissue product comprises (a) contacting the fetal support tissue product with a radioprotective composition for a predetermined period of time; and exposing fetal support tissue product to γ-irradiation at a dosage effective to sterilize the fetal support tissue product. In some embodiments, a method of sterilizing a fetal support tissue product comprises (a) contacting the fetal support tissue product with a radioprotective composition for a predetermined period of time; and exposing fetal support tissue product to γ-irradiation for a period of time sufficient to sterilize the fetal support tissue product and at a dosage effective to sterilize the fetal support tissue product. In some embodiments, dosimetry is employed to determine the exact amount of radiation administered.

In some embodiments, the radiation is administered at an effective rate. In some embodiments the effective rate of exposure to γ-irradiation is not more than about 0.3 kGy/hr, 1.0 kGy/hr, 2.0 kGy/hr, 3.0 kGy/hr, 6.0 kGy/hr, 18.0 kGy/hr, 30.0 kGy/hr, or 45.0 kGy/hr. In some embodiments, dose range of the γ-irradiation is between about 10 kGy and about 60 kGy, such as for example, between about 17 kGy and about 20 kGy, between about 20 kGy and about 24 kGy, or between about 25 kGy and about 30 kGy. In some embodiments, the radiation is administered for at or about 1 minute, 5 minutes, 10 minutes, 20 minutes, 30 minutes, 40 minutes, 50 minutes, 1 hour or longer.

In some embodiments, the fetal support tissue product is sterilized by electron beam irradiation. Methods for electron beam irradiation of biological tissues are known in the art and include, for example, methods described in U.S. Pat. No. 6,203,755.

In some embodiments, the radioprotective composition comprises glycerol, propylene glycol, DMSO, trehalose or any combination thereof. In particular embodiments, the radioprotective composition comprises glycerol. In particular embodiments, the radioprotective composition comprises propylene glycol. In some embodiments, the radioprotective composition comprises glycerol, propylene glycol, DMSO, trehalose or a combination thereof. In some embodiments, the radioprotective composition comprises glycerol and propylene glycol. In some embodiments, the radioprotective composition further comprises DMSO or trehalose. In some embodiments, the radioprotective composition is a solution comprising glycerol. In some embodiments, the radioprotective composition is a solution comprising propylene glycol.

In some embodiments, a method of sterilizing a fetal support tissue product comprises exposing a radioprotected fetal support tissue product to an effective dosage of radiation sufficient to sterilize the fetal support tissue product, wherein the radioprotected fetal support tissue product comprises a fetal support tissue product and a radioprotective composition (RPC) comprising glycerol, propylene glycol, DMSO, trehalose or a combination thereof. In some embodiments, the radiation is γ-radiation. In some embodiments, a method of sterilizing a fetal support tissue product comprises exposing a radioprotected fetal support tissue product to an effective dosage of γ-irradiation sufficient to sterilize the fetal support tissue product, wherein the radioprotected fetal support tissue product comprises a fetal support tissue product and a radioprotective composition (RPC) comprising glycerol, propylene glycol, DMSO, trehalose or a combination thereof. In some embodiments, the radioprotected fetal support tissue product is a frozen radioprotected fetal support tissue product.

In some embodiments, the method further comprises a step of freezing the radioprotected fetal support tissue product prior to irradiating the radioprotected fetal support tissue product. In some embodiments, the radioprotected fetal support tissue protect also is cryoprotected. In some embodiments the radioprotected fetal support tissue product is frozen at about 0° C., −5° C., −10° C., −20° C., −40° C., −50° C., −60° C., −70° C., or −80° C. In some embodiments, the radioprotected fetal support tissue product is exposed to γ-irradiation (i.e., irradiated) at or below about 0° C. In some embodiments, the radioprotected fetal support tissue product is exposed to γ-irradiation at about 0° C., −5° C., −10° C., −20° C., −40° C., −50° C., −60° C., −70° C., or −80° C. In some embodiments, the radioprotected fetal support tissue product is exposed to γ-irradiation on dry ice.

In some embodiments, a method of sterilizing a fetal support tissue product comprises exposing a frozen radioprotected fetal support tissue product to an effective dosage of radiation sufficient to sterilize the fetal support tissue product, wherein the radioprotected fetal support tissue product comprises a fetal support tissue product and a radioprotective composition (RPC) comprising glycerol, propylene glycol, DMSO, trehalose or a combination thereof. In some embodiments, a method of sterilizing a fetal support tissue product comprises: (a) freezing a radioprotected fetal support tissue product; and (b) exposing a frozen radioprotected fetal support tissue product to an effective dosage of radiation sufficient to sterilize the fetal support tissue product, wherein the radioprotected fetal support tissue product comprises a fetal support tissue product and a radioprotective composition (RPC) comprising glycerol, propylene glycol, DMSO, trehalose or a combination thereof. In some embodiments, the radioprotected fetal support tissue product is exposed to γ-irradiation at or below about 0° C. In some embodiments, the radioprotected fetal support tissue product is exposed to γ-irradiation at about 0° C., −5° C., −10° C., −20° C., −40° C., −50° C., −60° C., −70° C., or −80° C. In some embodiments, the radioprotected fetal support tissue product is exposed to γ-irradiation on dry ice.

In some embodiments, a method of sterilizing a fetal support tissue product comprises (a) contacting the fetal support tissue product with a radioprotective composition (RPC) comprising glycerol, propylene glycol, DMSO, trehalose or a combination thereof to generate a radioprotected fetal support tissue product; and (b) exposing the radioprotected fetal support tissue product to radiation to sterilize the fetal support tissue product. In some embodiments, the radiation is γ-radiation. In some embodiments, a method of sterilizing a fetal support tissue product comprises (a) contacting the fetal support tissue product with a radioprotective composition (RPC) comprising glycerol, propylene glycol, DMSO, trehalose or a combination thereof to generate a radioprotected fetal support tissue product; and (b) exposing the radioprotected fetal support tissue product to γ-irradiation at a dosage sufficient to sterilize the fetal support tissue product.

In some embodiments, the radioprotected fetal support tissue product is a frozen radioprotected fetal support tissue product. In some embodiments, the method further comprises a step of freezing the radioprotected fetal support tissue product prior to irradiating the fetal support tissue product. In some embodiments, a method of sterilizing a fetal support tissue product comprises (a) contacting a fetal support tissue product with a radioprotective composition (RPC) comprising glycerol, propylene glycol, DMSO, trehalose or a combination thereof to generate a radioprotected fetal support tissue product; (b) freezing the radioprotected fetal support tissue product; and (c) exposing the radioprotected fetal support tissue product to radiation to sterilize the fetal support tissue product. In some embodiments, a method of sterilizing a fetal support tissue product comprises (a) contacting a fetal support tissue product with a radioprotective composition (RPC) comprising glycerol, propylene glycol, DMSO, trehalose or a combination thereof to generate a radioprotected fetal support tissue product; (b) freezing the radioprotected fetal support tissue product; and (c) exposing the radioprotected fetal support tissue product to radiation to sterilize the fetal support tissue product. In some embodiments, the radioprotected fetal support tissue product is exposed to γ-irradiation at or below about 0° C. In some embodiments, the radioprotected fetal support tissue product is exposed to γ-irradiation at about 0° C., −5° C., −10° C., −20° C., −40° C., −50° C., −60° C., −70° C., or −80° C. In some embodiments, the radioprotected fetal support tissue product is exposed to γ-irradiation on dry ice.

In some embodiments, a method of sterilizing a fetal support tissue product comprises (a) contacting the fetal support tissue product with a radioprotective composition (RPC) comprising glycerol and propylene glycol or a combination thereof to generate a radioprotected fetal support tissue product; and (b) exposing the radioprotected fetal support tissue product to radiation to sterilize the fetal support tissue product. In some embodiments, the radiation is γ-radiation. In some embodiments, a method of sterilizing a fetal support tissue product comprises (a) contacting the fetal support tissue product with a radioprotective composition (RPC) comprising glycerol and propylene glycol or a combination thereof to generate a radioprotected fetal support tissue product; and (b) exposing the radioprotected fetal support tissue product to γ-irradiation at a dosage sufficient to sterilize the fetal support tissue product.

In some embodiments, the radioprotective composition is a solution comprising about 20% glycerol to about 80% glycerol, such as for example, about 20% glycerol to about 70% glycerol, such as for example, about 30% glycerol to about 70% glycerol, such as for example, about 30% glycerol to about 60% glycerol, such as for example, about 30% glycerol to about 50% glycerol. In some embodiments, the radioprotective composition is solution comprising about 30%, 35%, 40%, 45%, 50%, 55%, 60%, 65%, 70%, 75% or 80% glycerol. In some embodiments, the radioprotective composition is in a solution comprising about 30%-70% glycerol. In some embodiments, the radioprotective composition is a solution comprising about 50% glycerol.

In some embodiments, the radioprotective composition is a solution comprising about 1% propylene glycol to about 40% propylene glycol, such as for example, about 1% to about 30% propylene glycol, such as, for example, about 5% propylene glycol to about 30% propylene glycol, such as for example, about 10% propylene glycol to about 30% propylene glycol, such as for example, about 10% propylene glycol to about 25% propylene glycol, such as for example, about 10% propylene glycol to about 30% propylene glycol. In some embodiments, the radioprotective composition is a solution comprising about 1%, 2%, 3%, 4%, 5%, 10%, 15%, 20%, 25%, 30%, 35%, or 40% propylene glycol. In some embodiments, the radioprotective composition is a solution comprising about 1%-30% propylene glycol. In some embodiments, the radioprotective composition is a solution comprising about 10% propylene glycol.

In some embodiments, radioprotective composition is prepared by mixing a radioprotecting agent (e.g., glycerol or propylene glycol) in a buffer or other isotonic solution. In some embodiments, the mixture is homogenized. In some embodiments, the buffer is phosphate buffered saline (PBS). In some embodiments, the buffer is DMEM.

In some embodiments, a method of sterilizing a fetal support tissue product comprises (a) contacting the fetal support tissue product with a radioprotective composition comprising glycerol to generate a radioprotected fetal support tissue product; and (b) exposing the radioprotected fetal support tissue product to radiation to sterilize the fetal support tissue product. In some embodiments, the radiation is γ-radiation. In some embodiments, a method of sterilizing a fetal support tissue product comprises (a) contacting the fetal support tissue product with a radioprotective composition comprising glycerol to generate a radioprotected fetal support tissue product; and (b) exposing the radioprotected fetal support tissue product to γ-irradiation at a dosage sufficient to sterilize the fetal support tissue product. In some embodiments the radioprotected fetal support tissue product is frozen prior to exposure to γ-irradiation. In some embodiments, the radioprotected fetal support tissue product is exposed to γ-irradiation at or below about 0° C. In some embodiments, the radioprotected fetal support tissue product is exposed to γ-irradiation at about 0° C., −5° C., −10° C., −20° C., −40° C., −50° C., −60° C., −70° C., or −80° C. In some embodiments, the radioprotected fetal support tissue product is exposed to γ-irradiation on dry ice.

In some embodiments, a method of sterilizing a fetal support tissue product comprises (a) contacting the fetal support tissue product with a radioprotective composition comprising about 30%-70% glycerol to generate a radioprotected fetal support tissue product; and (b) exposing the radioprotected fetal support tissue product to radiation to sterilize the fetal support tissue product. In some embodiments, the radiation is γ-radiation. In some embodiments, a method of sterilizing a fetal support tissue product comprises (a) contacting the fetal support tissue product with a radioprotective composition comprising about 30%-70% glycerol to generate a radioprotected fetal support tissue product; and (b) exposing the radioprotected fetal support tissue product to γ-irradiation at a dosage sufficient to sterilize the fetal support tissue product. In some embodiments the radioprotected fetal support tissue product is frozen prior to exposure to γ-irradiation. In some embodiments, the radioprotected fetal support tissue product is exposed to γ-irradiation at or below about 0° C. In some embodiments, the radioprotected fetal support tissue product is exposed to γ-irradiation at about 0° C., −5° C., −10° C., −20° C., −40° C., −50° C., −60° C., −70° C., or −80° C. In some embodiments, the radioprotected fetal support tissue product is exposed to γ-irradiation on dry ice.

In some embodiments, a method of sterilizing a fetal support tissue product comprises (a) contacting the fetal support tissue product with a radioprotective composition comprising at or about 50% glycerol to generate a radioprotected fetal support tissue product; and (b) exposing the radioprotected fetal support tissue product to radiation to sterilize the fetal support tissue product. In some embodiments, the radiation is γ-radiation. In some embodiments, a method of sterilizing a fetal support tissue product comprises (a) contacting the fetal support tissue product with a radioprotective composition comprising at or about 50% glycerol to generate a radioprotected fetal support tissue product; and (b) exposing the radioprotected fetal support tissue product to γ-irradiation at a dosage sufficient to sterilize the fetal support tissue product. In some embodiments the radioprotected fetal support tissue product is frozen prior to exposure to γ-irradiation. In some embodiments, the radioprotected fetal support tissue product is exposed to γ-irradiation at or below about 0° C. In some embodiments, the radioprotected fetal support tissue product is exposed to γ-irradiation at about 0° C., −5° C., −10° C., −20° C., −40° C., −50° C., −60° C., −70° C., or −80° C. In some embodiments, the radioprotected fetal support tissue product is exposed to γ-irradiation on dry ice.

In some embodiments, a method of sterilizing a fetal support tissue product comprises (a) contacting the fetal support tissue product with a radioprotective composition comprising propylene glycol to generate a radioprotected fetal support tissue product; and (b) exposing the radioprotected fetal support tissue product to radiation to sterilize the fetal support tissue product. In some embodiments, the radiation is γ-radiation. In some embodiments, a method of sterilizing a fetal support tissue product comprises (a) contacting the fetal support tissue product with a radioprotective composition comprising propylene glycol to generate a radioprotected fetal support tissue product; and (b) exposing the radioprotected fetal support tissue product to γ-irradiation at a dosage sufficient to sterilize the fetal support tissue product. In some embodiments the radioprotected fetal support tissue product is frozen prior to exposure to γ-irradiation. In some embodiments, the radioprotected fetal support tissue product is exposed to γ-irradiation at or below about 0° C. In some embodiments, the radioprotected fetal support tissue product is exposed to γ-irradiation at about 0° C., −5° C., −10° C., −20° C., −40° C., −50° C., −60° C., −70° C., or −80° C. In some embodiments, the radioprotected fetal support tissue product is exposed to γ-irradiation on dry ice.

In some embodiments, a method of sterilizing a fetal support tissue product comprises (a) contacting the fetal support tissue product with a radioprotective composition comprising about 10%-30% propylene glycol to generate a radioprotected fetal support tissue product; and (b) exposing the radioprotected fetal support tissue product to radiation to sterilize the fetal support tissue product. In some embodiments, the radiation is γ-radiation. In some embodiments, a method of sterilizing a fetal support tissue product comprises (a) contacting the fetal support tissue product with a radioprotective composition comprising about 10%-30% propylene glycol to generate a radioprotected fetal support tissue product; and (b) exposing the radioprotected fetal support tissue product to γ-irradiation at a dosage sufficient to sterilize the fetal support tissue product. In some embodiments the radioprotected fetal support tissue product is frozen prior to exposure to γ-irradiation. In some embodiments, the radioprotected fetal support tissue product is exposed to γ-irradiation at or below about 0° C. In some embodiments, the radioprotected fetal support tissue product is exposed to γ-irradiation at about 0° C., −5° C., −10° C., −20° C., −40° C., −50° C., −60° C., −70° C., or −80° C. In some embodiments, the radioprotected fetal support tissue product is exposed to γ-irradiation on dry ice.

In some embodiments, a method of sterilizing a fetal support tissue product comprises (a) contacting the fetal support tissue product with a radioprotective comprising at or about 10% propylene glycol to generate a radioprotected fetal support tissue product; and (b) exposing the radioprotected fetal support tissue product to radiation to sterilize the fetal support tissue product. In some embodiments, the radiation is γ-radiation. In some embodiments, a method of sterilizing a fetal support tissue product comprises (a) contacting the fetal support tissue product with a radioprotective composition comprising at or about 10% propylene glycol to generate a radioprotected fetal support tissue product; and (b) exposing the radioprotected fetal support tissue product to γ-irradiation at a dosage sufficient to sterilize the fetal support tissue product. In some embodiments the radioprotected fetal support tissue product is frozen prior to exposure to γ-irradiation. In some embodiments, the radioprotected fetal support tissue product is exposed to γ-irradiation at or below about 0° C. In some embodiments, the radioprotected fetal support tissue product is exposed to γ-irradiation at about 0° C., −5° C., −10° C., −20° C., −40° C., −50° C., −60° C., −70° C., or −80° C. In some embodiments, the radioprotected fetal support tissue product is exposed to γ-irradiation on dry ice.

In an exemplary method, the radioprotective composition is added to the fetal support tissue product and incubated for a period of time. In some embodiments, the radioprotective composition is added to the fetal support tissue product and incubated for 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours or longer. In some embodiments, the radioprotective composition and the fetal support tissue product are incubated at about room temperature. In some embodiments, the radioprotective composition and the fetal support tissue product are incubated at about 4° C. In some embodiments, the radioprotective composition is a cryoprotective agent. In some embodiments, fetal support tissue product is incubated with a radioprotective composition and a cryoprotective agent.

In some embodiments, the fetal support tissue product is frozen following incubation of the fetal support tissue product with the radioprotective composition and prior to exposure to radiation. In some embodiments the radioprotective composition is a cryoprotecting agent. In some embodiments, the fetal support tissue product is frozen following incubation of the fetal support tissue product with the radioprotective composition and a cryoprotective agent and prior to exposure to radiation In some embodiments, the fetal support tissue product is lyophilized prior to exposure of the fetal support tissue product to radiation. Exemplary methods for the lyophilization are provided herein. In some embodiments, the fetal support tissue product is frozen prior to lyophilization of the fetal support tissue product. In some embodiments, the frozen fetal support tissue product is thawed and then lyophilized prior to exposure to γ-irradiation. In some embodiments, about 10%, 20%, 30%, 40%, 50%, 60%, 70%, 80%, 90%, 95%, 96%, 97%, 98%, 99%, or greater of the water content in the fetal support tissue product is removed by lyophilization. In some embodiments, the fetal support tissue product is lyophilized complete dryness. In some embodiments, the fetal support tissue product is not lyophilized to complete dryness.

In some embodiments, a method of sterilizing a fetal support tissue product comprises (a) contacting the fetal support tissue product with a radioprotective composition (RPC) to generate a radioprotected fetal support tissue product; (b) lyophilizing the radioprotected fetal support tissue product; and (c) exposing the radioprotected fetal support tissue product to radiation to sterilize the fetal support tissue product. In some embodiments, the radiation is γ-radiation. In some embodiments, a method of sterilizing a fetal support tissue product comprises (a) contacting the fetal support tissue product with a radioprotective composition (RPC) to generate a radioprotected fetal support tissue product; (b) lyophilizing the radioprotected fetal support tissue product; and (c) exposing the radioprotected fetal support tissue product to γ-irradiation at a dosage sufficient to sterilize the fetal support tissue product. In some embodiments the radioprotected fetal support tissue product is frozen prior to exposure to γ-irradiation. In some embodiments, the radioprotected fetal support tissue product is exposed to γ-irradiation at or below about 0° C. In some embodiments, the radioprotected fetal support tissue product is exposed to γ-irradiation at about 0° C., −5° C., −10° C., −20° C., −40° C.,−50° C., −60° C., −70° C., or −80° C. In some embodiments, the radioprotected fetal support tissue product is exposed to γ-irradiation on dry ice.

In some embodiments, a method of sterilizing a fetal support tissue product comprises (a) contacting the fetal support tissue product with a radioprotective composition comprising glycerol to generate a radioprotected fetal support tissue product; (b) lyophilizing the radioprotected fetal support tissue product; and (c) exposing the radioprotected fetal support tissue product to radiation to sterilize the fetal support tissue product. In some embodiments, the radiation is γ-radiation. In some embodiments, a method of sterilizing a fetal support tissue product comprises (a) contacting the fetal support tissue product with a radioprotective composition comprising glycerol to generate a radioprotected fetal support tissue product; (b) lyophilizing the radioprotected fetal support tissue product; and (c) exposing the radioprotected fetal support tissue product to γ-irradiation at a dosage sufficient to sterilize the fetal support tissue product. In some embodiments the radioprotected fetal support tissue product is frozen prior to exposure to γ-irradiation. In some embodiments, the radioprotected fetal support tissue product is exposed to γ-irradiation at or below about 0° C. In some embodiments, the radioprotected fetal support tissue product is exposed to γ-irradiation at about 0° C., −5° C., −10° C., −20° C., −40° C., −50° C., −60° C., −70° C., or −80° C. In some embodiments, the radioprotected fetal support tissue product is exposed to γ-irradiation on dry ice.

In some embodiments, a method of sterilizing a fetal support tissue product comprises (a) contacting the fetal support tissue product with a radioprotective composition comprising about 30%-70% glycerol to generate a radioprotected fetal support tissue product; (b) lyophilizing the radioprotected fetal support tissue product; and (c) exposing the radioprotected fetal support tissue product to radiation to sterilize the fetal support tissue product. In some embodiments, the radiation is γ-radiation. In some embodiments, a method of sterilizing a fetal support tissue product comprises (a) contacting the fetal support tissue product with a radioprotective composition comprising about 30%-70% glycerol to generate a radioprotected fetal support tissue product; (b) lyophilizing the radioprotected fetal support tissue product; and (c) exposing the radioprotected fetal support tissue product to γ-irradiation at a dosage sufficient to sterilize the fetal support tissue product. In some embodiments the radioprotected fetal support tissue product is frozen prior to exposure to γ-irradiation. In some embodiments, the radioprotected fetal support tissue product is exposed to γ-irradiation at or below about 0° C. In some embodiments, the radioprotected fetal support tissue product is exposed to γ-irradiation at about 0° C., −5° C., −10° C., −20° C., −40° C., −50° C., −60° C., −70° C., or −80° C. In some embodiments, the radioprotected fetal support tissue product is exposed to γ-irradiation on dry ice.

In some embodiments, a method of sterilizing a fetal support tissue product comprises (a) contacting the fetal support tissue product with a radioprotective composition comprising at or about 50% glycerol to generate a radioprotected fetal support tissue product; (b) lyophilizing the radioprotected fetal support tissue product; and (c) exposing the radioprotected fetal support tissue product to radiation to sterilize the fetal support tissue product. In some embodiments, the radiation is γ-radiation. In some embodiments, a method of sterilizing a fetal support tissue product comprises (a) contacting the fetal support tissue product with a radioprotective composition comprising at or about 50% glycerol to generate a radioprotected fetal support tissue product; (b) lyophilizing the radioprotected fetal support tissue product; and (c) exposing the radioprotected fetal support tissue product to γ-irradiation at a dosage sufficient to sterilize the fetal support tissue product. In some embodiments the radioprotected fetal support tissue product is frozen prior to exposure to γ-irradiation. In some embodiments, the radioprotected fetal support tissue product is exposed to γ-irradiation at or below about 0° C. In some embodiments, the radioprotected fetal support tissue product is exposed to γ-irradiation at about 0° C., −5° C., −10° C., −20° C., −40° C., −50° C., −60° C., −70° C., or −80° C. In some embodiments, the radioprotected fetal support tissue product is exposed to γ-irradiation on dry ice.

In some embodiments, a method of sterilizing a fetal support tissue product comprises (a) contacting the fetal support tissue product with a radioprotective composition comprising propylene glycol to generate a radioprotected fetal support tissue product; (b) lyophilizing the radioprotected fetal support tissue product; and (c) exposing the radioprotected fetal support tissue product to radiation to sterilize the fetal support tissue product. In some embodiments, the radiation is γ-radiation. In some embodiments, a method of sterilizing a fetal support tissue product comprises (a) contacting the fetal support tissue product with a radioprotective composition comprising propylene glycol to generate a radioprotected fetal support tissue product; (b) lyophilizing the radioprotected fetal support tissue product; and (c) exposing the radioprotected fetal support tissue product to γ-irradiation at a dosage sufficient to sterilize the fetal support tissue product. In some embodiments the radioprotected fetal support tissue product is frozen prior to exposure to γ-irradiation. In some embodiments, the radioprotected fetal support tissue product is exposed to γ-irradiation at or below about 0° C. In some embodiments, the radioprotected fetal support tissue product is exposed to γ-irradiation at about 0° C., −5° C., −10° C., −20° C., −40° C., −50° C., −60° C., −70° C., or −80° C. In some embodiments, the radioprotected fetal support tissue product is exposed to γ-irradiation on dry ice.

In some embodiments, a method of sterilizing a fetal support tissue product comprises (a) contacting the fetal support tissue product with a radioprotective composition comprising about 10%-30% propylene glycol to generate a radioprotected fetal support tissue product; (b) lyophilizing the radioprotected fetal support tissue product; and (c) exposing the radioprotected fetal support tissue product to radiation to sterilize the fetal support tissue product. In some embodiments, the radiation is γ-radiation. In some embodiments, a method of sterilizing a fetal support tissue product comprises (a) contacting the fetal support tissue product with a radioprotective composition comprising about 10%-30% propylene glycol to generate a radioprotected fetal support tissue product; (b) lyophilizing the radioprotected fetal support tissue product; and (c) exposing the radioprotected fetal support tissue product to γ-irradiation at a dosage sufficient to sterilize the fetal support tissue product. In some embodiments the radioprotected fetal support tissue product is frozen prior to exposure to γ-irradiation. In some embodiments, the radioprotected fetal support tissue product is exposed to γ-irradiation at or below about 0° C. In some embodiments, the radioprotected fetal support tissue product is exposed to γ-irradiation at about 0° C., −5° C., −10° C., −20° C., −40° C., −50° C., −60° C., −70° C., or −80° C. In some embodiments, the radioprotected fetal support tissue product is exposed to γ-irradiation on dry ice.

In some embodiments, a method of sterilizing a fetal support tissue product comprises (a) contacting the fetal support tissue product with a radioprotective composition comprising at or about 10% propylene glycol to generate a radioprotected fetal support tissue product; (b) lyophilizing the radioprotected fetal support tissue product; and (c) exposing the radioprotected fetal support tissue product to radiation to sterilize the fetal support tissue product. In some embodiments, the radiation is γ-radiation. In some embodiments, a method of sterilizing a fetal support tissue product comprises (a) contacting the fetal support tissue product with a radioprotective composition comprising at or about 10% propylene glycol to generate a radioprotected fetal support tissue product; (b) lyophilizing the radioprotected fetal support tissue product; and (c) exposing the radioprotected fetal support tissue product to γ-irradiation at a dosage sufficient to sterilize the fetal support tissue product. In some embodiments the radioprotected fetal support tissue product is frozen prior to exposure to γ-irradiation. In some embodiments, the radioprotected fetal support tissue product is exposed to γ-irradiation at or below about 0° C. In some embodiments, the radioprotected fetal support tissue product is exposed to γ-irradiation at about 0° C., −5° C., −10° C., −20° C., −40° C., −50° C., −60° C., −70° C., or −80° C. In some embodiments, the radioprotected fetal support tissue product is exposed to γ-irradiation on dry ice.

In some embodiments, the excess radioprotective composition is removed from radioprotected fetal support tissue product prior to sterilization by irradiation. In some embodiments, the radioprotected fetal support tissue product is blotted with an absorbent material to remove excess radioprotective composition. In some embodiments, the radioprotected fetal support tissue product is rinsed with water or an isotonic buffer to remove excess radioprotective composition. In some embodiments, the radioprotected fetal support tissue product is blotted with an absorbent material to remove excess water or rinse buffer.

In some embodiments, the radioprotected fetal support tissue product is placed on a support membrane. In some embodiments, the membrane, is a polyethersulfone (PES) membrane, a nylon membrane, or a nitrocellulose membrane.

In some embodiments, the radioprotected fetal support tissue product is placed in packaging suitable for irradiation of the fetal support tissue product. Suitable packaging includes, for example, packaging that maintains a seal against the external environment during and following irradiation of the product, is not reactive with the support membrane, and does produce any chemicals that interact with the fetal support tissue product. In some embodiments, the radioprotected fetal support tissue product is place on a support membrane and then the combination of the support membrane and the fetal support tissue product is place in suitable packaging prior to exposure to γ-irradiation. In some embodiments, the membrane, is a polyethersulfone (PES) membrane, a nylon membrane, or a nitrocellulose membrane.

In some embodiments, the fetal support tissue product is prepared and stored as a "Wet" cryopreserved fetal support tissue product. In such embodiments, the fetal support tissue product is contacted with the radioprotective composition as a liquid storage media. The composition of the fetal support tissue product with the radioprotective composition is then exposed to γ-irradiation. The volume of the storage media can vary according to the type of fetal support tissue product employed. In some embodiments the volume is about 1 ml to about 10 ml. The product is kept wet in the storage medium, and there is no limit on the incubation duration except until the product expires. In some embodiments, the fetal support tissue product is stored at −80° C., −40° C., −20° C., 4° C., or Room Temperature.

In some embodiments, the fetal support tissue product is prepared and stored as a "Dry" Lyophilized fetal support tissue product. For example, the product is prepared by contacting the fetal support tissue product with the radioprotective composition for a period of time as described herein and then lyophilized. The lyophilized product is them stored at −80° C., −40° C., −20° C., 4° C., or Room Temperature prior to exposure to γ-irradiation.

Lyophilization

In some embodiments, methods provided herein for the preparation and sterilization of fetal support tissue product comprise lyophilizing the fetal support tissue product prior to exposure to γ-irradiation. Duration of lyophilization, temperature at which lyophilization is conducted, and the pressure at which lyophilization is conducted are varied according to the desired outcome. It is within the skill of one skilled in the art to determine the necessary parameters for lyophilization of the fetal support tissue product.

In some embodiments, the fetal support tissue product is lyophilized by any suitable method (e.g., exposure to a liquid gas, placement in a freezer). In some embodiments, the isolated fetal support tissue product is placed in the vacuum chamber of a lyophilization device until all or substantially all fluid (e.g., water) has been removed. In some embodiments, the fetal support tissue product is frozen prior to lyophilization. In some embodiments, the frozen fetal support tissue product is thawed prior to lyophilization. In some embodiments, the frozen fetal support tissue product is not thawed prior to lyophilization.

In some embodiments, about 10%, 20%, 30%, 40%, 50%, 60%, 70%, 80%, 90%, 95%, 96%, 97%, 98%, 99%, or greater of the water content in the fetal support tissue product is removed by lyophilization. In some embodiments, the fetal support tissue product is lyophilized complete dryness. In some embodiments, the fetal support tissue product is not lyophilized to complete dryness.

Primary Drying Cycle

The fetal support tissue product is lyophilized at any suitable temperature. In some embodiments, lyophilizing the fetal support tissue product at a temperature at or below freezing results in the fetal support tissue product having greater potency (e.g., anti-inflammatory potency, anti-scarring potency, anti-angiogenesis potency, anti-adhesion potency, or wound healing potency) as compared to a fetal support tissue product that is not lyophilized or at below freezing. In some embodiments, the fetal support tissue product is lyophilized at a temperature below freezing. In some embodiments, the fetal support tissue product is lyophilized at a temperature below about 0° C., −5° C., −10° C., −20° C., −40° C., −50° C., −60° C., −70° C., −80° C., −90° C., −100° C. In some embodiments, the fetal support tissue product is lyophilized at −5° C.

In some embodiments, the primary drying cycle occurs at a pressure of less than about 500 millitorr. In some embodiments, the primary drying cycle occurs at a pressure of less than about 400 millitorr. In some embodiments, the primary drying cycle occurs at a pressure of less than about 300 millitorr. In some embodiments, the primary drying cycle occurs at a pressure of less than about 250 millitorr. In some embodiments, the primary drying cycle occurs at a pressure of less than about 200 millitorr. In some embodiments, the fetal support tissue product is lyophilized at a pressure of 100 millitorr. In some embodiments, decreasing the lyophilization pressure decreases the lyophilization time. In some embodiments, lyophilization is more effective at a pressure of less than 500 millitorr.

In some embodiments, lyophilization occurs until substantially all moisture is removed from the fetal support tissue product. The lyophilization time required depends on the type of tissue used, the amount of tissue, and the thickness of the tissue. In some embodiments, lyophilization occurs for more than about 12 hours. In some embodiments, lyophilization occurs for more than about 14 hours. In some embodiments, lyophilization occurs for more than about 16 hours. In some embodiments, lyophilization occurs for more than about 18 hours. In some embodiments, lyophilization occurs for more than about 20 hours. In some embodiments, lyophilization occurs for more than about 21 hours. In some embodiments, lyophilization occurs for more than about 22 hours. In some embodiments, lyophilization occurs for more than about 23 hours. In some embodiments, lyophilization occurs for about 24 hours.

In some embodiments, the fetal support tissue product is lyophilized at −5° C. at a pressure of 100 millitorr. In some embodiments, the fetal support tissue product is lyophilized at −5° C. at a pressure of 100 millitorr for about 21 hours.

In some embodiments, methods provided herein for the preparation and sterilization of fetal support tissue product further comprise gradually increasing the ambient temperature of the lyophilizer to room temperature (i.e., about 25° C.) following lyophilization. The rate at which the temperature of the lyophilizer is increased depends on the capability of the equipment. In some embodiments, increasing the temperature of the lyophilizer to room temperature helps to prevent condensation when taking the tissue out of the lyophilizer.

Secondary Drying Cycle

In some embodiments, methods provided herein for the preparation and sterilization of fetal support tissue product further comprise a secondary drying cycle. In some embodiments, the secondary drying cycle occurs at room temperature (e.g., about 25° C.). The temperature of the secondary drying cycle may be any temperature above the temperature set for primary drying. In some embodiments, condensation is decreased or prevented if the temperature of the secondary drying cycle is at about room temperature (e.g., 25° C.).

In some embodiments, the secondary drying cycle occurs at a pressure of less than about 500 millitorr. In some embodiments, the secondary drying cycle occurs at a pressure of less than about 400 millitorr. In some embodiments, the secondary drying cycle occurs at a pressure of less than about 300 millitorr. In some embodiments, the secondary drying cycle occurs at a pressure of less than about 250 millitorr. In some embodiments, the secondary drying cycle occurs at a pressure of less than about 200 millitorr. In some embodiments, the secondary drying cycle occurs at a pressure of about 100 millitorr. In some embodiments, decreasing the drying pressure decreases the lyophilization time.

In some embodiments, the secondary drying cycle lasts for less than about 24 hours. In some embodiments, the secondary drying cycle lasts for less than about 20 hours. In some embodiments, the secondary drying cycle lasts for less than about 18 hours. In some embodiments, the secondary drying cycle lasts for less than about 16 hours. In some embodiments, the secondary drying cycle lasts for about 16 hours. In some embodiments, the secondary drying cycle lasts for less than about 14 hours. In some embodiments, the secondary drying cycle lasts for less than about 12 hours. In some embodiments, the secondary drying cycle lasts for less than about 10 hours. In some embodiments, the secondary drying cycle lasts for less than about 8 hours. In some embodiments, the secondary drying cycle lasts for less than about 6 hours. In some embodiments, the secondary drying cycle lasts for less than about 4 hours. In some embodiments, the secondary drying cycle lasts for less than about 2 hours. In some embodiments, the secondary drying cycle lasts for less than about 1 hours.

Sterilized Fetal Support Tissue Products and Properties Thereof

Provided herein are sterilized fetal support tissue products produced by the methods provided herein for the preparation and sterilization of fetal support tissue products. In some embodiments, the sterilized fetal support tissue products provided herein retain one or more activities or properties of a fetal support tissue product that has not been sterilized by the methods provided herein. In some embodiments, the sterilized fetal support tissue products provided herein retain one or more activities or properties of a fetal support tissue product that is freshly isolated. In some embodiments, the sterilized fetal support tissue products provided herein has the equivalent or similar activity compared to a cryopreserved fetal support tissue product. In some embodiments, the sterilized fetal support tissue products provided herein has increased activity compared to a cryopreserved fetal support tissue product. In some embodiments, the sterilized fetal support tissue products provided herein has decreased activity compared to a cryopreserved fetal support tissue product. Exemplary properties or therapeutic activities include, but are not limited to, anti-inflammation, anti-scarring, anti-adhesion, wound healing or tissue regeneration. In some embodiments, the sterilized fetal support tissue products provided herein retains about 10%, 20%, 30%, 40%, 50%, 60%, 70%, 80%, 90% or greater activity compared a fetal support tissue product that is freshly isolated. In some embodiments, activity is assessed by an osteoclast inhibition assay, a macrophage viability assay, or a TGF-β promoter activity assay. Exemplary assays for activity are provided herein and known in the art.

In some embodiments, the structural integrity the sterilized fetal support tissue product is preserved. For examples, in some embodiments, the sterilized fetal support tissue product comprises intact AM layers, including epithelium, stroma and basement membrane. In some embodiments, the structural integrity of the epithelium, stroma and basement membrane in the sterilized fetal support tissue product is not compromised. In some embodiments, the AM epithelium is present in the sterilized fetal support tissue product as assessed by Hematoxylin and Eosin staining. In some embodiments, the AM basement membrane is present in the sterilized fetal support tissue product as assessed by Alcian Blue staining. In some embodiments, the AM stroma is present in the sterilized fetal support tissue product as assessed by Periodic Acid-Schiff Reaction (PAS) staining.

In some embodiments, the structural integrity of the sterilized fetal support tissue product is preserved for 6 months, 12 month 18 months, 24 months, 30 months, 36 months, 42 months, 48 months, or longer. In some embodiments, the therapeutic activity of the sterilized fetal support tissue product is preserved for 6 months, 12 month 18 months, 24 months, 30 months, 36 months, 42 months, 48 months, or longer.

In some embodiments, the sterilized fetal support tissue product is provided as a lyophilized product. In some embodiments, a fetal support tissue product is rehydrated prior to use as a therapeutic. In some embodiments, a fetal support tissue product disclosed herein is rehydrated by contacting the fetal support tissue product with a buffer or with water. In some embodiments, a fetal support tissue product disclosed herein is contacted with an isotonic buffer. In some embodiments, a fetal support tissue product disclosed herein is contacted with saline, PBS, Ringer's solution, TRIS-buffered saline, Hank's balanced salt solution, Hartmann's solution. In some embodiments, a fetal support tissue product disclosed herein is contacted with water (e.g. distilled water).

Fetal Support Tissue Products for Use in the Methods

The methods provided herein for the preparation and sterilization of a fetal support tissue product are applicable to any biological product comprising a fetal support tissue. A fetal support tissue product is obtained from any suitable source of fetal support tissues (e.g., a hospital or tissue bank). In some embodiments, the fetal support tissue is obtained from any mammal, such as a human, non-human primate, cow or pig.

In some embodiments, the fetal support tissue product is derived from placental amniotic membrane (PAM) or substantially isolated PAM. In some embodiments, the fetal support tissue product is derived from umbilical cord amniotic membrane (UCAM) or substantially isolated UCAM. In some embodiments, the fetal support tissue product is derived from chorion or substantially isolated chorion. In some embodiments, the fetal support tissue product is derived from amnion-chorion or substantially isolated amnion-chorion. In some embodiments, the fetal support tissue product is derived from placenta or substantially isolated placenta. In some embodiments, the fetal support tissue product is derived from umbilical cord or substantially isolated umbilical cord. In some embodiments, the fetal support tissue product is derived from any combinations of one or more of placental amniotic membrane (PAM), or substantially isolated PAM, (ii) umbilical cord amniotic membrane (UCAM) or substantially isolated UCAM, (iii) chorion or substantially isolated chorion, (iv) amnion-chorion or substantially isolated amnion-chorion, (v) placenta or substantially isolated placenta, (vi) umbilical cord or substantially isolated umbilical cord. In some embodiments, the fetal support tissue product is AmnioGraft®, ProRem®, AmnioGuard®, Neox 100®, Neox 1k® or Clarix®.

In some embodiments, all processing of the fetal support tissue product is done following Current Good Tissue Practices (cGTP) to ensure that no contaminants are introduced into the fetal support tissue products In some embodiments, the fetal support tissue product is frozen (e.g., at or below 0° C.) until donor and specimen eligibility has been determined. In some embodiments, freezing the fetal support tissue product kills substantially all cells found in the fetal support tissue product. In some embodiments, freezing the fetal support tissue product kills substantially all cells found in fetal support tissue product while maintaining or increasing the biological activity of the fetal support tissue product relative to fresh (i.e., non-frozen) fetal support tissue product. In some embodiments, freezing the fetal support tissue product results in the loss of metabolic activity in substantially all cells found in the fetal support tissue product. In some embodiments, freezing the fetal support tissue product results in the loss of metabolic activity in substantially all cells found in the fetal support tissue product while maintaining or increasing the biological activity of the fetal support tissue product (e.g., its anti-inflammatory, anti-scarring, anti-antigenic, and anti-adhesion properties) relative to fresh (i.e., non-frozen) fetal support tissue product. In some embodiments, the fetal support tissue product is frozen prior to the application of the methods provided herein for the preparation and sterilization of a fetal support tissue product.

In some embodiments, the fetal support tissue product is not frozen. If the fetal support tissue product is not frozen, it is processed as described according to the methods provided herein for the preparation and sterilization of a fetal support tissue product.

In some embodiments, substantially all blood is removed from the fetal support tissue product. In some embodiments, substantially all blood is removed from the fetal support tissue product before the fetal support tissue product is frozen. In some embodiments, substantially all blood is removed from the fetal support tissue product before the fetal support tissue product is processed as described according to the methods provided herein for the preparation and sterilization of a fetal support tissue product.

In some embodiments, blood is not removed from the fetal support tissue product. In some embodiments, blood is not removed from the fetal support tissue product before the fetal support tissue product is frozen. In some embodiments, substantially all blood is removed from the thawed fetal support tissue product before the fetal support tissue product is processed as described according to the methods provided herein for the preparation and sterilization of a fetal support tissue product.

In some embodiments, the fetal support tissue product is contacted with an isotonic buffer. In some embodiments, the fetal support tissue product is contacted with saline, PBS, PBS 1×, Ringer's solution, Hartmann's solution, TRIS-buffered saline, HEPES-buffered saline, EBSS, HBSS, Tyrode's salt Solution, Grey's Balanced Salt Solution, DMEM, EMEM, GMEM, RPMI, or any combinations thereof.

In some embodiments, the fetal support tissue product is washed with buffer with agitation to remove excess blood and tissue. In some embodiments, the fetal support tissue product is washed with agitation.

In some embodiments, the fetal support tissue product is umbilical cord or umbilical cord amniotic membrane. In some embodiments, the Wharton's Jelly is not removed from the umbilical cord or the umbilical cord amniotic membrane. In some embodiments, part or all of the Wharton's Jelly is removed from the umbilical cord or the umbilical cord amniotic membrane.

Umbilical cord comprises two arteries (the umbilical arteries) and one vein (the umbilical vein). In certain instances, the vein and arteries are surrounded (or suspended or buried) within the Wharton's Jelly. In some embodiments, the veins and arteries are not removed from the umbilical cord. In some embodiments, the vein and arteries are removed from the umbilical cord. In some embodiments, the vein and arteries are removed concurrently with the removal of the Wharton's Jelly.

In some embodiments, the fetal support tissue product is tested for HIV-1, HIV-2, HTLV-1, hepatitis B and C, West Nile virus, cytomegalovirus, chagas, human transmissible spongiform encephalopathy (e.g., Creutzfeldt-Jakob disease) and *treponema pallidum* using an FDA licensed screening test. any indication that the tissue is contaminated with HIV-1, HIV-2, HTLV-1, hepatitis B and C, West Nile virus, or cytomegalovirus results in the immediate quarantine and subsequent destruction of the tissue specimen.

Further, the donor's medical records are examined for risk factors for and clinical evidence of hepatitis B, hepatitis C, or HIV infection. any indication that the donor has risk factors for, and/or clinical evidence of, infection with HIV-1, HIV-2, HTLV-1, hepatitis B and C, West Nile virus, cytomegalovirus, chagas, human transmissible spongiform encephalopathy (e.g., Creutzfeldt-Jakob disease) and *treponema pallidum* results in the immediate quarantine and subsequent destruction of the tissue specimen.

Freezing

In some embodiments, the fetal support tissue product is frozen prior to the application of the methods provided herein for the preparation and sterilization of a fetal support tissue product. In some embodiments, the fetal support tissue product is frozen by exposure to a temperature below about 0° C., −5° C., −10° C., −20° C., −40° C., −50° C., −60° C., −70° C., −80° C., −90° C., −100° C. prior to the application of the methods provided herein for the preparation and sterilization of a fetal support tissue product. In some embodiments, the fetal support tissue product is contacted with a radioprotective composition prior to freezing. In some embodiments, the fetal support tissue product is contacted with a cryoprotecting agent prior to freezing. In some embodiments, the radioprotective composition is a cryoprotecting agent. In some embodiments, the fetal support tissue product is contacted with a radioprotective composition and a cryoprotecting agent prior to freezing.

In some embodiments, the samples are frozen at about −40° C. In some embodiments, freezing the fetal support tissue product prior to lyophilization results in the fetal support tissue product having greater potency (e.g., anti-inflammatory potency, anti-scarring potency, anti-angiogenesis potency, anti-adhesion potency, or wound healing potency) as compared to a fetal support tissue product that is not frozen prior to lyophilization.

In some embodiments, methods of making fetal support tissue products comprise (a) freezing the fetal support tissue product, and (b) drying the fetal support tissue product.

Processing to Make a Fetal Support Tissue Product Powder

In some embodiments, the fetal support tissue product is in the form of a powder. In some embodiments, the fetal support tissue product is lyophilized and then ground into a powder.

Lyophilization

In some embodiments, methods of making a fetal support tissue powder product comprise lyophilizing the fetal support tissue before grinding the fetal support tissue. Duration of lyophilization, temperature at which lyophilization is conducted, and the pressure at which lyophilization is conducted may be varied according to the desired outcome. It is within the skill of one skilled in the art to determine the necessary parameters.

In some embodiments, the isolated fetal support tissue is lyophilized by any suitable method (e.g., exposure to a liquid gas, placement in a freezer). In some embodiments, the isolated fetal support tissue is placed in the vacuum chamber of a lyophilization device until all or substantially all fluid (e.g., water) has been removed.

In some embodiments, the fetal support tissue is frozen prior to lyophilization.

Primary Drying Cycle

The fetal support tissue is lyophilized at any suitable temperature. In some embodiments, lyophilizing the fetal support tissue at a temperature at or below freezing results in the fetal support tissue powder product having greater potency (e.g., anti-inflammatory potency, anti-scarring potency, anti-angiogenesis potency, anti-adhesion potency, or wound healing potency) as compared to a fetal support tissue powder product that is not lyophilized at or below freezing. In some embodiments, the fetal support tissue is lyophilized at a temperature below freezing. In some embodiments, the fetal support tissue is lyophilized at a temperature below about 0° C., −20° C., −40° C., −50° C., −60° C., −70° C., −75° C., −80° C., −90° C., −100° C.). In some embodiments, the fetal support tissue is lyophilized at −5° C.

In some embodiments, the primary drying cycle occurs at a pressure of less than about 500 millitorr. In some embodiments, the primary drying cycle occurs at a pressure of less than about 400 millitorr. In some embodiments, the primary drying cycle occurs at a pressure of less than about 300 millitorr. In some embodiments, the primary drying cycle occurs at a pressure of less than about 250 millitorr. In some embodiments, the primary drying cycle occurs at a pressure of less than about 200 millitorr. In some embodiments, the fetal support tissue is lyophilized at a pressure of 100 millitorr. In some embodiments, decreasing the lyophilization pressure decreases the lyophilization time. In some embodiments, lyophilization is more effective at a pressure of less than 500 millitorr.

In some embodiments, lyophilization occurs until the fetal support tissue is dry enough for the fetal support tissue to be effectively ground. Grinding ease and efficiency is increased with the dryness of the fetal support tissue. In some embodiments, lyophilization occurs until substantially all moisture is removed from the fetal support tissue. The lyophilization time required depends on the type of tissue used, the amount of tissue, and the thickness of the tissue. In some embodiments, lyophilization occurs for more than about 12 hours. In some embodiments, lyophilization occurs for more than about 14 hours. In some embodiments, lyophilization occurs for more than about 16 hours. In some embodiments, lyophilization occurs for more than about 18 hours. In some embodiments, lyophilization occurs for more than about 20 hours. In some embodiments, lyophilization occurs for more than about 21 hours. In some embodiments, lyophilization occurs for more than about 22 hours. In some embodiments, lyophilization occurs for more than about 23 hours. In some embodiments, lyophilization occurs for about 24 hours.

In some embodiments, the fetal support tissue is lyophilized at −5° C. at a pressure of 100 millitorr. In some embodiments, the fetal support tissue is lyophilized at −5° C. at a pressure of 100 millitorr for about 21 hours.

In some embodiments, methods of making a fetal support tissue powder product further comprise gradually increasing the ambient temperature of the lyophilizer to room temperature (i.e., about 25° C.) following lyophilization. The rate at which the temperature of the lyophilizer is increased depends on the capability of the equipment. In some embodiments, increasing the temperature of the lyophilizer to room temperature helps to prevent condensation when taking the tissue out of the lyophilizer Secondary Drying Cycle In some embodiments, methods of making fetal support tissue powder products further comprise a secondary drying cycle. In some embodiments, the secondary drying cycle occurs at room temperature (e.g., about 25° C.). The temperature of the secondary drying cycle may be any temperature above the temperature set for primary drying. In some embodiments, condensation is decreased or prevented if the temperature of the secondary drying cycle is at about room temperature (e.g., 25° C.).

In some embodiments, the secondary drying cycle occurs at a pressure of less than about 500 millitorr. In some embodiments, the secondary drying cycle occurs at a pressure of less than about 400 millitorr. In some embodiments, the secondary drying cycle occurs at a pressure of less than about 300 millitorr. In some embodiments, the secondary drying cycle occurs at a pressure of less than about 250 millitorr. In some embodiments, the secondary drying cycle occurs at a pressure of less than about 200 millitorr. In some embodiments, the secondary drying cycle occurs at a pressure of about 100 millitorr. In some embodiments, decreasing the drying pressure decreases the lyophilization time.

In some embodiments, the secondary drying cycle lasts for less than about 24 hours. In some embodiments, the secondary drying cycle lasts for less than about 20 hours. In some embodiments, the secondary drying cycle lasts for less than about 18 hours. In some embodiments, the secondary drying cycle lasts for less than about 16 hours. In some embodiments, the secondary drying cycle lasts for about 16 hours. In some embodiments, the secondary drying cycle lasts for less than about 14 hours. In some embodiments, the secondary drying cycle lasts for less than about 12 hours. In some embodiments, the secondary drying cycle lasts for less than about 10 hours. In some embodiments, the secondary drying cycle lasts for less than about 8 hours. In some embodiments, the secondary drying cycle lasts for less than about 6 hours. In some embodiments, the secondary drying cycle lasts for less than about 4 hours. In some embodiments, the secondary drying cycle lasts for less than about 2 hours. In some embodiments, the secondary drying cycle lasts for less than about 1 hours.

In some embodiments, methods of making fetal support tissue powder products further comprise a secondary drying cycle at 25° C. at a pressure of 100 millitorr. In some embodiments, methods of making fetal support tissue powder products further comprise a secondary drying cycle at 25° C. at a pressure of 100 millitorr for less than about 16 hours.

In some embodiments, methods of making fetal support tissue powder products comprise a primary drying cycle at about −5° C. at a pressure of about 100 millitorr, and a secondary drying cycle at about 25° C. at a pressure of about 100 millitorr. In some embodiments, methods of making fetal support tissue powder products comprise a primary drying cycle at about −5° C. at a pressure of about 100 millitorr for about 21 hours, and a secondary drying cycle at about 25° C. at a pressure of about 100 millitorr for less than about 16 hours.

Grinding

In some embodiments, the fetal support tissue is ground by any suitable method. Duration and frequency of grinding may be varied according to the desired outcome. It is within the skills of one skilled in the art to determine the necessary parameters.

In some embodiments, the lyophilized fetal support tissue is ground by use of a grinding container. In some embodiments, the lyophilized fetal support tissue is ground by use of a pulverizer (e.g., a Bessman Tissue Pulverizer or a Covaris CryoPrep). In some embodiments, the lyophilized fetal support tissue is ground by use of a tissue grinder (e.g., a Potter-Elvehjem grinder or a Wheaton Overhead Stirrer). In some embodiments, the lyophilized fetal support tissue is ground by use of a sonicator. In some embodiments, the lyophilized fetal support tissue is ground by use of a bead beater. In some embodiments, the lyophilized fetal support tissue is ground by use of a freezer/mill (e.g., a SPEX SamplePrep Freezer/Mill). In some embodiments, lyophilized fetal support tissue is ground by use of a pestle and mortar. In some embodiments, the lyophilized fetal support tissue is ground by manual use of a pestle and mortar.

In some embodiments, the lyophilized fetal support tissue is ground by use of a grinding container. In some embodiments, the fetal support tissue is ground at a frequency of between about 10 Hz and about 25 Hz. In some embodiments, the fetal support tissue is ground at a frequency of about 10 Hz. In some embodiments, the fetal support tissue is ground at a frequency of about 15 Hz. In some embodiments, the fetal support tissue is ground at a frequency of about 20 Hz. In some embodiments, the fetal support tissue is ground at a frequency of about 25 Hz. In some embodiments, grinding lasts for any suitable time period. The lower the grinding frequency, the greater the amount of time required to grind the lyophilized fetal support tissue. The duration of grinding varies with the desired form of the powder. In some embodiments, grinding lasts for between about 1 and about 6 minutes, for example about 1 minute, about 2 minutes, about 3 minutes, about 4 minutes, about 5 minutes, or about 6 minutes.

In some embodiments, grinding the lyophilized fetal support tissue further comprises continuously freezing the lyophilized fetal support tissue. For example, in some embodiments, the lyophilized fetal support tissue is placed in a grinding container and the grinding container is exposed to temperatures below 0° C. (e.g., the grinding container is immersed in liquid nitrogen or the container comprises an automated liquid nitrogen cooling feature).

Methods of Use

Provided herein are methods of using a sterilized fetal support tissue product disclosed herein. In some embodiments, a sterilized fetal support tissue product disclosed herein is used to inhibit at least one of the following: scarring, inflammation, adhesion and angiogenesis. In some embodiments, a sterilized fetal support tissue product disclosed herein is used to promote wound healing. In some embodiments, the use is a homologous use. In some embodiments, a sterilized fetal support tissue product disclosed herein is minimally manipulated. In some embodiments, a sterilized fetal support tissue product disclosed herein does not comprise another article, except for water, crystalloids, or a sterilizing, preserving, or storage agent. In some embodiments, a sterilized fetal support tissue product disclosed herein does not have a systemic effect and is not dependent upon the metabolic activity of living cells for its primary function.

In some embodiments, a sterilized fetal support tissue product disclosed herein is used as a covering (e.g., a wound covering). In some embodiments, the use is a homologous use. In some embodiments, the sterilized fetal support tissue product is minimally manipulated. In some embodiments, the sterilized fetal support tissue product does not comprise another article, except for water, crystalloids, or a sterilizing, preserving, or storage agent. In some embodiments, the sterilized fetal support tissue product does not have a systemic effect and is not dependent upon the metabolic activity of living cells for its primary function.

In some embodiments, a sterilized fetal support tissue product disclosed herein is used to promote wound repair. In some embodiments, the use is a homologous use. In some embodiments, the sterilized fetal support tissue product is minimally manipulated. In some embodiments, the sterilized fetal support tissue product does not comprise another article, except for water, crystalloids, or a sterilizing, preserving, or storage agent. In some embodiments, the sterilized fetal support tissue product does not have a systemic effect and is not dependent upon the metabolic activity of living cells for its primary function.

In some embodiments, a sterilized fetal support tissue product disclosed herein is used as a barrier to adhesion. In some embodiments, the use is a homologous use. In some embodiments, the sterilized fetal support tissue product is minimally manipulated. In some embodiments, the sterilized fetal support tissue product does not comprise another article, except for water, crystalloids, or a sterilizing, preserving, or storage agent. In some embodiments, the sterilized fetal support tissue product does not have a systemic effect and is not dependent upon the metabolic activity of living cells for its primary function.

In some embodiments, a sterilized fetal support tissue product disclosed herein comprises proteins, glycans, protein-glycan complexes (e.g., a complex of hyaluronic acid and a heavy chain of IαI and PTX3) and enzymes that promote tissue repair. For example, the stroma of AM comprises growth factors, anti-angiogenic and anti-inflammatory proteins, as well as natural inhibitors to various proteases. In some embodiments, proteins and enzymes found in a sterilized fetal support tissue product disclosed herein diffuse out of the sterilized fetal support tissue product and into the surrounding tissue.

Injured Tissue Repair and Supplementation

Disclosed herein, in certain embodiments, is the use of a sterilized fetal support tissue product disclosed herein for repairing, reconstructing, replacing, or supplementing a recipient's damaged, compromised, or missing tissue. In some embodiments, a sterilized fetal support tissue product disclosed herein is used as a wound covering or is used to facilitate wound repair. In some embodiments, the use is a homologous use (e.g., a functional homologous use or a structural homologous use). In some embodiments, the sterilized fetal support tissue product is minimally manipulated. In some embodiments, the sterilized fetal support tissue product does not comprise another article, except for water, crystalloids, or a sterilizing, preserving, or storage agent. In some embodiments, the sterilized fetal support tissue product does not have a systemic effect and is not dependent upon the metabolic activity of living cells for its primary function.

In some embodiments, the tissue was damaged, compromised, or lost due to an injury (e.g., a burn; a surgical incision; an area of necrosis resulting from an infection, trauma, or a toxin; a laceration). In some embodiments, the tissue was damaged, compromised, or lost due to a burn. In some embodiments, the tissue was damaged, compromised, or lost due to a wound (e.g., an incision, laceration, abrasion). In some embodiments, the tissue was damaged, compromised, or lost due to necrosis. In some embodiments, the tissue was damaged, compromised, or lost due to ulceration.

In some embodiments, a sterilized fetal support tissue product disclosed herein comprises proteins, glycans, protein-glycan complexes (e.g., a complex of hyaluronic acid and a heavy chain of IαI and PTX3) and enzymes that promote tissue repair. For example, the stroma of AM comprises growth factors, anti-angiogenic and anti-inflammatory proteins, as well as natural inhibitors to various proteases. In some embodiments, proteins and enzymes found in a sterilized fetal support tissue product disclosed herein diffuse out of the sterilized fetal support tissue product and into the surrounding tissue.

Burns

In some embodiments, a sterilized fetal support tissue product disclosed herein is applied to a burn. In some embodiments, a sterilized fetal support tissue product disclosed herein is applied to a first degree burn. In some embodiments, a sterilized fetal support tissue product disclosed herein is applied to a second degree burn. In some embodiments, a sterilized fetal support tissue product disclosed herein is applied to a third degree burn. In some embodiments, the sterilized fetal support tissue product is applied to a substrate prior to be placed on the burn.

Wounds

In some embodiments, a sterilized fetal support tissue product disclosed herein is applied to a wound in the skin (e.g., an incision, laceration, abrasion, ulcer, puncture, penetration). In some embodiments, the sterilized fetal support tissue product is applied to a substrate prior to being placed on the wound.

In some embodiments, a sterilized fetal support tissue product disclosed herein is applied to an incision in an organ (e.g., the skin, brain, stomach, kidneys, liver, intestines, lungs, bladder, trachea, esophagus, vagina, ureter, and blood vessel walls). In some embodiments, a sterilized fetal support tissue product disclosed herein is applied to a surgical incision. In some embodiments, a sterilized fetal support tissue product disclosed herein is applied to the site of a colon resection. In some embodiments, a sterilized fetal support tissue product disclosed herein is applied to the site of a gastrectomy. In some embodiments, a sterilized fetal support tissue product disclosed herein is applied to the site of a breast surgery (e.g., breast reduction surgery, breast augmentation surgery, and mastectomy). In some embodiments, the sterilized fetal support tissue product is applied to a substrate prior to being placed on the wound.

In some embodiments, a sterilized fetal support tissue product disclosed herein is used as a covering over an incision in the skin (e.g., an incision to the epidermis, dermis, and/or hypodermis). In some embodiments, a sterilized fetal support tissue product disclosed herein is used to repair or supplement the skin following hemorrhoid surgery. In some embodiments, the sterilized fetal support tissue product is applied to a substrate prior to being placed on the wound.

Necrosis

In some embodiments, a sterilized fetal support tissue product disclosed herein is used as a protective graft over an area of necrotic tissue (e.g., from an infection). In some embodiments, a sterilized fetal support tissue product disclosed herein is used as a protective graft over an area of necrotic skin. In some embodiments, a sterilized fetal support tissue product disclosed herein is placed on an area of necrotic tissue. In some embodiments, the sterilized fetal support tissue product is applied to a substrate prior to being placed on the necrotic tissue.

Ulcer

In some embodiments, a sterilized fetal support tissue product disclosed herein is used as a protective covering over an ulcer. In some embodiments, the sterilized fetal support tissue product is applied to a substrate prior to being placed on the ulcer.

In some embodiments, the ulcer is a foot ulcer (e.g., a diabetic foot ulcer or an arterial insufficiency ulcer). In some embodiments, treating a foot ulcer comprises (a) preparing the wound (e.g., debriding the wound); and (b) placing a sterilized fetal support tissue product disclosed herein on the wound. In some embodiments, treating a foot ulcer comprises (a) preparing the wound (e.g., debriding the wound); (b) placing a sterilized fetal support tissue product disclosed herein on the wound; and (c) covering the sterilized fetal support tissue product with a protective barrier (e.g., a silvercell dressing, metipel, gauze, or a bandage). In some embodiments, the sterilized fetal support tissue product is applied to a substrate prior to being placed on the ulcer.

In some embodiments, the ulcer is a venous stasis (VS) ulcer. In some embodiments, treating a VS ulcer comprises (a) preparing the wound (e.g., debriding the wound); and (b) placing A sterilized fetal support tissue product disclosed herein on the wound. In some embodiments, treating a VS ulcer comprises (a) preparing the wound (e.g., debriding the wound); (b) placing a sterilized fetal support tissue product disclosed herein on the wound; and (c) covering the sterilized fetal support tissue product with a protective barrier (e.g., a wound veil, antimicrobial dressing, gauze, or a bandage). In some embodiments, the sterilized fetal support tissue product is applied to a substrate prior to being placed on the wound.

In some embodiments, the ulcer is a corneal ulcer (i.e., ulcerative keratitis). In some embodiments, treating a corneal ulcer comprises (a) preparing the wound (e.g., debriding the wound); and (b) placing a sterilized fetal support tissue product disclosed herein on the wound. In some embodiments, treating a corneal ulcer comprises (a) preparing the wound (e.g., debriding the wound); (b) placing a sterilized fetal support tissue product disclosed herein on the wound; and (c) covering the sterilized fetal support tissue product or sterilized fetal support tissue product with a protective barrier (e.g., a contact lens or a bandage). In some embodiments, the sterilized fetal support tissue product is applied to a substrate prior to being placed on the wound.

Soft Tissue Uses

Disclosed herein, in certain embodiments, is the use of a sterilized fetal support tissue product disclosed herein for repairing, reconstructing, replacing, or supplementing a recipient's damaged, compromised, or missing soft tissue (e.g., tendons). In some embodiments, the use is a homologous use. In some embodiments, the sterilized fetal support tissue product is minimally manipulated. In some embodiments, the sterilized fetal support tissue product does not comprise another article, except for water, crystalloids, or a sterilizing, preserving, or storage agent. In some embodiments, the sterilized fetal support tissue product does not have a systemic effect and is not dependent upon the metabolic activity of living cells for its primary function.

In some embodiments, a sterilized fetal support tissue product disclosed herein comprises proteins, glycans, protein-glycan complexes (e.g., a complex of hyaluronic acid and a heavy chain of IαI and PTX3) and enzymes that promote tissue repair. For example, the stroma of AM comprises growth factors, anti-angiogenic and anti-inflammatory proteins, as well as natural inhibitors to various proteases. In some embodiments, proteins and enzymes found in a sterilized fetal support tissue product disclosed herein diffuse out of the sterilized fetal support tissue product and into the surrounding tissue.

In some embodiments, a sterilized fetal support tissue product disclosed herein described herein is used as a covering over an incision in soft tissue (e.g., eyelids form the tissue plane between different layers of soft tissue). In some embodiments, the sterilized fetal support tissue product is applied to a substrate and then used as a covering over an incision in soft tissue (e.g., eyelids form the tissue plane between different layers of soft tissue).

In some embodiments, a sterilized fetal support tissue product disclosed herein is used as structural (tectonic) support for soft tissue.

In some embodiments, a sterilized fetal support tissue product disclosed herein prevents adhesion in joint or tendon repairs.

In some embodiments, a sterilized fetal support tissue product disclosed herein is used in the repair a tendon or joint (such as rotator cuff repairs, hand tendon repairs). In some embodiments, a sterilized fetal support tissue product disclosed herein is used to reinforce a tendon or joint. In some embodiments, a sterilized fetal support tissue product disclosed herein is used to prevent adhesion of a healing tendon to surrounding tissue, tendons or joints. In some embodiments, a sterilized fetal support tissue product disclosed herein is used to prevent the formation of scar tissue on a tendon.

In some embodiments, a sterilized fetal support tissue product disclosed herein is applied to a substrate and the substrate/sterilized fetal support tissue product is used to augment smaller tendons and ligaments of the foot and ankle, including the posterior tibial tendon, the personneal tendons, the flexor and extensor tendons, and the ligaments of the lateral ankle complex. In some embodiments, a sterilized fetal support tissue product disclosed herein is applied to a substrate and the substrate/sterilized fetal support tissue product is used to reinforce primary repair of the quadriceps and patellar tendons surrounding the knee. In some embodiments, a sterilized fetal support tissue product disclosed herein is applied to a substrate and the substrate/ sterilized fetal support tissue product is used as a periosteal patch for bone graft in joint replacement. In some embodiments, a sterilized fetal support tissue product disclosed herein is applied to a substrate and the substrate/sterilized fetal support tissue product is used to augment deficient hip and knee capsular tissue following total joint revision surgery.

In some embodiments, a sterilized fetal support tissue product disclosed herein is applied to a substrate and the substrate/sterilized fetal support tissue product is used in the repair of a torn rotator cuff. In some embodiments, a sterilized fetal support tissue product disclosed herein is applied to a substrate and the substrate/sterilized fetal support tissue product is used as a patch over a rotator cuff muscle or tendon (e.g., the supraspinatus tendon). In some embodiments, a sterilized fetal support tissue product disclosed herein is applied to a substrate and the substrate/sterilized fetal support tissue product is used to reconstruct a rotator cuff muscle or tendon (e.g., the supraspinatus tendon). In some embodiments, a sterilized fetal support tissue product disclosed herein is applied to a substrate and the substrate/sterilized fetal support tissue product is used to augment a rotator cuff muscle or tendon (e.g., the supraspinatus tendon). In some embodiments, a sterilized fetal support tissue product disclosed herein is applied to a substrate and the substrate/sterilized fetal support tissue product is used to reinforce a rotator cuff muscle or tendon (e.g., the supraspinatus tendon). In some embodiments, a sterilized fetal support tissue product disclosed herein is applied to a substrate and the substrate/sterilized fetal support tissue product is used to prevent adhesion of soft tissue to a rotator cuff muscle or tendon (e.g., the supraspinatus tendon).

In some embodiments, a sterilized fetal support tissue product disclosed herein is used in the repair gingiva. In some embodiments, a sterilized fetal support tissue product disclosed herein is used in the repair gingival recession. In some embodiments, a sterilized fetal support tissue product disclosed herein is applied to a substrate and used as a patch over gingiva. In some embodiments, a sterilized fetal support tissue product disclosed herein is applied to substrate and used as a patch over an exposed tooth root surface. In some embodiments, a sterilized fetal support tissue product disclosed herein is used to reconstruct gingiva. In some embodiments, a sterilized fetal support tissue product disclosed herein is used to augment gingiva. In some embodiments, a sterilized fetal support tissue product disclosed herein is used to reinforce gingiva. In some embodiments, a sterilized fetal support tissue product disclosed herein is used to prevent adhesion of soft tissue to gingiva.

In some embodiments, a sterilized fetal support tissue product described herein is applied to a substrate and the substrate/sterilized fetal support tissue product is used as a protective graft over an incision or tear in the fascia. In some embodiments, a sterilized fetal support tissue product disclosed herein is applied to a substrate and the substrate/sterilized fetal support tissue product is used as structural (tectonic) support the fascia. In some embodiments, a sterilized fetal support tissue product disclosed herein is applied to a substrate and the substrate/sterilized fetal support tissue product is used as a replacement or supplement for the fascia. In some embodiments, a sterilized fetal support tissue product disclosed herein is applied to a substrate and the substrate/sterilized fetal support tissue product is used to repair a hernia (e.g., to repair the fascia). In some embodiments, a sterilized fetal support tissue product disclosed herein is applied to a substrate and the substrate/sterilized fetal support tissue product is used to repair an inguinal hernia. In some embodiments, a sterilized fetal support tissue product disclosed herein is applied to a substrate and the substrate/sterilized fetal support tissue product is used to repair a femoral hernia. In some embodiments, a sterilized fetal support tissue product disclosed herein is applied to a substrate and the substrate/sterilized fetal support tissue product is used to repair an umbilical hernia. In some embodiments, a sterilized fetal support tissue product disclosed herein is applied to a substrate and the substrate/sterilized fetal support tissue product is used to repair an incisional hernia. In some embodiments, a sterilized fetal support tissue product disclosed herein is applied to a substrate and the substrate/sterilized fetal support tissue product is used to repair a diaphragmatic hernia. In some embodiments, a sterilized fetal support tissue product disclosed herein is applied to a substrate and the substrate/sterilized fetal support tissue product is used to repair a Cooper's hernia, an epigastric hernia, an hiatal hernia, a Littre's hernia, a lumbar hernia, a maydl hernia, an obturator hernia, a pantaloon hernia, a paraesophageal hernia, a paraumbilical hernia, a perineal hernia, a properitoneal hernia, a Richter's hernia, a sliding hernia, a sciatic hernia, a spigelian hernia, a sports hernia, a Velpeau hernia, or a Amyand's hernia.

In some embodiments, a sterilized fetal support tissue product disclosed herein is applied to a substrate and the substrate/sterilized fetal support tissue product is used to repair a spinal disc herniation. In some embodiments, a sterilized fetal support tissue product disclosed herein is applied to a substrate and the substrate/sterilized fetal support tissue product is used as a protective graft over an incision or tear in a spinal disc. In some embodiments, a sterilized fetal support tissue product disclosed herein is applied to a substrate and the substrate/sterilized fetal support tissue product is used as a protective graft over an incision or tear in an annulus fibrosis. In some embodiments, a sterilized fetal support tissue product disclosed herein is applied to a substrate and the substrate/sterilized fetal support tissue product is used as structural (tectonic) support a spinal disc. In some embodiments, a sterilized fetal support tissue product disclosed herein is applied to a substrate and the substrate/sterilized fetal support tissue product is used as structural (tectonic) support an annulus fibrosis. In some embodiments, a sterilized fetal support tissue product disclosed herein is applied to a substrate and the substrate/sterilized fetal support tissue product is used as a replacement or supplement for a spinal disc. In some embodiments, a sterilized fetal support tissue product disclosed herein is applied to a substrate and the substrate/sterilized fetal support tissue product is used as structural (tectonic) support a spinal disc. In some embodiments, a sterilized fetal support tissue product disclosed herein is applied to a substrate and the substrate/sterilized fetal support tissue product is used as a replacement or supplement for an annulus fibrosis.

In some embodiments, a sterilized fetal support tissue product disclosed herein is applied to a substrate and the substrate/sterilized fetal support tissue product is used over an incision in the brain, or in one (or all) of the meninges (i.e., the dura mater, the pia mater, and/or the arachnoid mater). In some embodiments, a sterilized fetal support tissue product disclosed herein is applied to a substrate and the substrate/sterilized fetal support tissue product is used as structural (tectonic) support for one (or all) of the meninges (i.e., the dura mater, the pia mater, and/or the arachnoid mater). In some embodiments, a sterilized fetal support tissue product disclosed herein is applied to a substrate and the substrate/sterilized fetal support tissue product is used as a replacement for one (or all) of the meninges (i.e., the dura mater, the pia mater, and/or the arachnoid mater).

In some embodiments, a sterilized fetal support tissue product disclosed herein is applied to a substrate and the substrate/sterilized fetal support tissue product is used over an incision in a lung or in the pleura. In some embodiments, a sterilized fetal support tissue product disclosed herein is applied to a substrate and the substrate/sterilized fetal support tissue product is used as structural (tectonic) support for the pleura. In some embodiments, a sterilized fetal support tissue product disclosed herein is applied to a substrate and the substrate/sterilized fetal support tissue product is used as a replacement for the pleura.

In some embodiments, a sterilized fetal support tissue product disclosed herein is applied to a substrate and the substrate/sterilized fetal support tissue product is used over an incision in a tympanic membrane. In some embodiments, a sterilized fetal support tissue product disclosed herein is applied to a substrate and the substrate/sterilized fetal support tissue product is used as structural (tectonic) support for a tympanic membrane. In some embodiments, a sterilized fetal support tissue product disclosed herein is applied to a substrate and the substrate/sterilized fetal support tissue product is used as a replacement for a tympanic membrane.

In some embodiments, a sterilized fetal support tissue product disclosed herein is applied to a substrate and the substrate/sterilized fetal support tissue product is used as a protective graft over an incision in the heart or the pericardium. In some embodiments, a sterilized fetal support tissue product disclosed herein is applied to a substrate and the substrate/sterilized fetal support tissue product is used as structural (tectonic) support for the pericardium. In some embodiments, a sterilized fetal support tissue product disclosed herein is applied to a substrate and the substrate/sterilized fetal support tissue product is used as a replacement for the pericardium.

In some embodiments, a sterilized fetal support tissue product disclosed herein is applied to a substrate and the substrate/sterilized fetal support tissue product is used as a protective graft over an incision in the peritoneum. In some embodiments, a sterilized fetal support tissue product disclosed herein is applied to a substrate and the substrate/sterilized fetal support tissue product is used as structural (tectonic) support for the peritoneum. In some embodiments, a sterilized fetal support tissue product disclosed herein is applied to a substrate and the substrate/sterilized fetal support tissue product is used as a replacement for the peritoneum.

Ophthalmic Uses

Disclosed herein, in certain embodiments, is the use of a sterilized fetal support tissue product disclosed herein for repairing, reconstructing, replacing, or supplementing a recipient's damaged, compromised, or missing ocular tissue. In some embodiments, the use is a homologous use. In some embodiments, the sterilized fetal support tissue product is minimally manipulated. In some embodiments, the sterilized fetal support tissue product does not comprise another article, except for water, crystalloids, or a sterilizing, preserving, or storage agent. In some embodiments, the sterilized fetal support tissue product disclosed herein does not have a systemic effect and is not dependent upon the metabolic activity of living cells for its primary function.

In some embodiments, a sterilized fetal support tissue product disclosed herein comprises proteins, glycans, protein-glycan complexes (e.g., a complex of hyaluronic acid and a heavy chain of IαI and PTX3) and enzymes that promote tissue repair. For example, the stroma of AM comprises growth factors, anti-angiogenic and anti-inflammatory proteins, as well as natural inhibitors to various proteases. In some embodiments, proteins and enzymes found in a sterilized fetal support tissue product disclosed herein diffuse out of the sterilized fetal support tissue product and into the surrounding tissue.

Treatment of Glaucoma

As used herein, "Glaucoma" means a disorder characterized by the loss of retinal ganglion cells in the optic nerve. In certain instances, glaucoma partially or fully results from an increase in intraocular pressure in the anterior chamber (AC). Intraocular pressure varies depending on the production of liquid aqueous humor by the ciliary processes of the eye and the drainage of the aqueous humor through the trabecular meshwork.

Glaucoma Drainage Devices (GDD) are medical devices that are implanted into an eye to relieve intraocular pressure by providing an alternative pathway for the aqueous humor to drain. If left uncovered, a GDD tube will erode and leave the eye susceptible to intraocular infection. Thus, the GDD tube needs to be covered. Currently, patches used to cover GDD tubes are made from pericardium, sclera and cornea. These patches are about 400-550 microns thick. The thinness of these patches results in their melting by 25% in 2 years potentially leaving the shunt tube exposed again.

In some embodiments, a sterilized fetal support tissue product disclosed herein is applied to a substrate and the substrate/sterilized fetal support tissue product is used to cover GDD tubes. In some embodiments, the substrate/sterilized fetal support tissue product is 300-600 microns thick. In some embodiments, the substrate/sterilized fetal support tissue product does not melt by 25% in 2 years.

Treatment of Ocular Ulcers

In some embodiments, a sterilized fetal support tissue product disclosed herein is applied to a substrate and the substrate/sterilized fetal support tissue product is used to cover persistent epithelial defects and/or ulcers in eyes.

In some embodiments, the base of the ulcer is debrided with surgical sponges and the poorly adherent epithelium adjacent to the edge of the ulcer is removed (e.g., to the section of the eye where the epithelium becomes quite adherent). In some embodiments, a sterilized fetal support tissue product disclosed herein is applied to a substrate and the substrate/sterilized fetal support tissue product is transferred to the recipient eye. In some embodiments, a sterilized fetal support tissue product disclosed herein is applied to a substrate and the substrate/sterilized fetal support tissue product is then secured to the eye by sutures (e.g., interrupted 10-0 nylon sutures or running 10-0 nylon sutures) with the suture knots being buried. In some embodiments, a sterilized fetal support tissue product disclosed herein is applied to a substrate and the substrate/sterilized fetal support tissue product is secured to the eye by use of fibrin glue. In some embodiments, a protective layer is applied over the sterilized fetal support tissue product/substrate or the entire eye (e.g., a contact lens). In some embodiments, the substrate/sterilized fetal support tissue product further comprises an antibiotic (e.g., neomycin, polymyxin b sulfate and dexamethasone).

Conjunctival, Scleral, Lid, and Orbital Rim Surface Reconstruction

In some embodiments, a sterilized fetal support tissue product disclosed herein is applied to a substrate and the substrate/sterilized fetal support tissue product is used in conjunctival, scleral, lid, and orbital rim surface reconstruction. In some embodiments, damage to the conjunctival surface results from symblepharon lysis; surgical removal of tumor, lesion, and/or scar tissue; excimer laser photorefractive keratectomy and therapeutic keratectomy; or combinations thereof.

Coronary Uses

Disclosed herein, in certain embodiments, is the use of a sterilized fetal support tissue product disclosed herein for repairing, reconstructing, replacing, or supplementing a recipient's damaged, compromised, or missing coronary tissue. In some embodiments, the use is a homologous use. In some embodiments, the sterilized fetal support tissue product is minimally manipulated. In some embodiments, the AM does not comprise another article, except for water, crystalloids, or a sterilizing, preserving, or storage agent. In some embodiments, the sterilized fetal support tissue product does not have a systemic effect and is not dependent upon the metabolic activity of living cells for its primary function.

In some embodiments, a sterilized fetal support tissue product disclosed herein comprises proteins, glycans, protein-glycan complexes (e.g., a complex of hyaluronic acid and a heavy chain of I$\alpha$I and PTX3) and enzymes that promote tissue repair. For example, the stroma of AM comprises growth factors, anti-angiogenic and anti-inflammatory proteins, as well as natural inhibitors to various proteases. In some embodiments, proteins and enzymes found in the sterilized fetal support tissue product diffuse out of the sterilized fetal support tissue product and into the surrounding tissue.

Coronary Artery Bypass

Disclosed herein, is the use of a sterilized fetal support tissue product described herein in coronary artery bypass surgery. In some embodiments, a sterilized fetal support tissue product disclosed herein is applied to a substrate and the substrate/sterilized fetal support tissue product is grafted onto a coronary artery to bypass a section of the artery that is characterized by atherosclerosis.

Heart Valves

In some embodiments, a sterilized fetal support tissue product disclosed herein is applied to a substrate and the substrate/sterilized fetal support tissue product is applied over a heart valve. In some embodiments, a sterilized fetal support tissue product disclosed herein is applied to a substrate and the substrate/sterilized fetal support tissue product is used as structural (tectonic) support for a heart valve. In some embodiments, a sterilized fetal support tissue product disclosed herein is applied to a substrate and the substrate/sterilized fetal support tissue product is used as a replacement for a heart valve.

Veins and Arteries

In some embodiments, a sterilized fetal support tissue product disclosed herein is applied to a substrate and the substrate/sterilized fetal support tissue product is applied to a vein or artery. In some embodiments, a sterilized fetal support tissue product disclosed herein is applied to a substrate and the substrate/sterilized fetal support tissue product is used as structural (tectonic) support for a vein or artery.

Nerve Uses

Disclosed herein, in certain embodiments, is the use of a sterilized fetal support tissue product disclosed herein for repairing, reconstructing, replacing, or supplementing a recipient's damaged, compromised, or missing nerve. In some embodiments, the use is a homologous use. In some embodiments, the sterilized fetal support tissue product is minimally manipulated. In some embodiments, the sterilized fetal support tissue product does not comprise another article, except for water, crystalloids, or a sterilizing, preserving, or storage agent. In some embodiments, the sterilized fetal support tissue product does not have a systemic effect and is not dependent upon the metabolic activity of living cells for its primary function.

In some embodiments, a sterilized fetal support tissue product disclosed herein comprises proteins, glycans, protein-glycan complexes (e.g., a complex of hyaluronic acid and a heavy chain of I$\alpha$I and PTX3) and enzymes that promote tissue repair. For example, the stroma of AM comprises growth factors, anti-angiogenic and anti-inflammatory proteins, as well as natural inhibitors to various proteases. In some embodiments, proteins and enzymes found in a sterilized fetal support tissue product disclosed herein diffuse out of the sterilized fetal support tissue product and into the surrounding tissue.

In some embodiments, a sterilized fetal support tissue product disclosed herein is applied to a substrate and the substrate/sterilized fetal support tissue product is used as a covering over a nerve (e.g., a peripheral nerve). In some embodiments, a sterilized fetal support tissue product disclosed herein is applied to a substrate and the substrate/sterilized fetal support tissue product is used as a covering over a nerve graft, nerve transfer, or a repaired nerve. In some embodiments, a sterilized fetal support tissue product disclosed herein is applied to a substrate and the substrate/sterilized fetal support tissue product is used as a covering over an incision in a nerve (e.g., a peripheral nerve). In some embodiments, a sterilized fetal support tissue product disclosed herein is applied to a substrate and the substrate/sterilized fetal support tissue product is used as structural (tectonic) support for a nerve (e.g., a peripheral nerve). In some embodiments, a sterilized fetal support tissue product disclosed herein prevents adhesion in nerve repair.

In some embodiments, a sterilized fetal support tissue product disclosed herein is applied to a substrate and the substrate/sterilized fetal support tissue product is used as a non-constricting encasement for injured nerves. In some embodiments, a sterilized fetal support tissue product described herein prevents or minimizes scar formation, encapsulation, chronic compression, tethering of a nerve, and nerve entrapment. In some embodiments, a sterilized fetal support tissue product described herein prevents or minimizes neuroma formation. In some embodiments, a sterilized fetal support tissue product described herein prevents or minimizes the migration of endogenous growth factors (i.e. Nerve Growth Factor) present during nerve repair.

Spinal Uses

Disclosed herein, in certain embodiments, is the use of a sterilized fetal support tissue product described herein during spinal surgery. In some embodiments, a sterilized fetal support tissue product described herein is used during a laminectomy. In some embodiments, the use is a homologous use. In some embodiments, the sterilized fetal support tissue product is minimally manipulated. In some embodiments, the sterilized fetal support tissue product does not comprise another article, except for water, crystalloids, or a sterilizing, preserving, or storage agent. In some embodiments, the sterilized fetal support tissue product does not have a systemic effect and is not dependent upon the metabolic activity of living cells for its primary function.

In some embodiments, a sterilized fetal support tissue product disclosed herein comprises proteins, glycans, protein-glycan complexes (e.g., a complex of hyaluronic acid and a heavy chain of I$\alpha$I and PTX3) and enzymes that promote tissue repair. For example, the stroma of AM comprises growth factors, anti-angiogenic and anti-inflammatory proteins, as well as natural inhibitors to various proteases. In some embodiments, proteins and enzymes found in a sterilized fetal support tissue product disclosed herein diffuse out of the sterilized fetal support tissue product and into the surrounding tissue.

In some embodiments, a sterilized fetal support tissue product described herein is used to reduce or prevent epidural fibrosis and/or scar adhesions following spinal surgery (e.g., laminectomy). In some embodiments, a sterilized fetal support tissue product described herein is implanted between dura mater and overlying tissue following spinal surgery (e.g., laminectomy). In some embodiments, implanting a sterilized fetal support tissue product described herein between dura mater and overlying tissue following spinal surgery (e.g., laminectomy) reduces or prevents migration of fibroblasts to the dura mater and collagen deposition on the dura mater.

In some embodiments, a sterilized fetal support tissue product described herein is used to reduce or prevent the development of proliferative scarring following spinal surgery (e.g., laminectomy). In some embodiments, a sterilized fetal support tissue product described herein is used to reduce or prevent the development of a postoperative (e.g., postlaminectomy) epidural/peridural/perineural scar. In some embodiments, a sterilized fetal support tissue product described herein is used to reduce or prevent the development of proliferative scarring following spinal surgery (e.g., laminectomy). In some embodiments, a sterilized fetal support tissue product disclosed herein is used to reduce or prevent the development of a postlaminectomy membrane.

In some embodiments, a sterilized fetal support tissue product described herein is used to reduce or prevent the development of extradural compression or dural teethering following spinal surgery (e.g., laminectomy). In some embodiments, a sterilized fetal support tissue product described herein is used to reduce or prevent the development of tethered nerve roots following spinal surgery (e.g., laminectomy). In some embodiments, a sterilized fetal support tissue product described herein is used to reduce or prevent the development of arachnoiditis following spinal surgery (e.g., laminectomy).

In some embodiments, a sterilized fetal support tissue product disclosed herein further comprises morselized bone tissue. In some embodiments, a sterilized fetal support tissue product disclosed herein comprising morselized bone tissue is used during a spinal fusion procedure. In some embodiments, a sterilized fetal support tissue product disclosed herein comprising morselized bone tissue is implanted between adjacent vertebrae. In some embodiments, implantation of a sterilized fetal support tissue product disclosed herein comprising morselized bone tissue between two adjacent vertebrae promotes fusion of the vertebrae.

In some embodiments, a sterilized fetal support tissue product disclosed herein is used as a protective graft over an incision in the dura mater. In some embodiments, a sterilized fetal support tissue product disclosed herein is applied to a substrate and the substrate/sterilized fetal support tissue product is used as structural (tectonic) support for the dura mater. In some embodiments, a sterilized fetal support tissue product disclosed herein is applied to a substrate and the substrate/sterilized fetal support tissue product is used as a replacement for the dura mater.

Miscellaneous Uses of a Sterilized Fetal Support Tissue Product

In some embodiments, a sterilized fetal support tissue product disclosed herein is applied to a patch or wound dressing.

In some embodiments, a sterilized fetal support tissue product disclosed herein is used as a dermal filler. In some embodiments, a sterilized fetal support tissue product disclosed herein is injected into subdermal facial tissues. In some embodiments, a sterilized fetal support tissue product disclosed herein is injected under wrinkles and aging lines of the face (e.g., nasolabial folds, melomental folds, "crow's feet" and forehead wrinkles). In some embodiments, a sterilized fetal support tissue product disclosed herein is used for lip augmentation. In some embodiments, a sterilized fetal support tissue product disclosed herein is injected into the lips.

In some embodiments, a sterilized fetal support tissue product disclosed herein is used to treat arthritis (e.g., osteoarthritis, rheumatoid arthritis, septic arthritis, ankylosing spondylitis, spondylosis). In some embodiments, a sterilized fetal support tissue product disclosed herein is injected into an arthritic joint (e.g., a knee).

In some embodiments, a sterilized fetal support tissue product disclosed herein is used to treat an orthodontic or a periodontal condition. In some embodiments, the periodontal condition is selected from gingivitis, gingival recession or periodontitis. In some embodiments, a sterilized fetal support tissue product disclosed herein is used as an anti-inflammatory or used to promote ossteointegration or healing. In some embodiments, a sterilized fetal support tissue product disclosed herein is used in combination with a dental implant to promote implant ossteointegration, anti-inflammation, and healing.

In some embodiments, a sterilized fetal support tissue product disclosed herein to treat hoarseness or voice disorders. In some embodiments, a sterilized fetal support tissue product disclosed herein is used for injection laryngoplasty to repair vocal cords.

In some embodiments, a sterilized fetal support tissue product disclosed herein is coated onto a medical implant. In some embodiments, a medical implant/sterilized fetal support tissue product disclosed herein is implanted into an individual in need thereof, wherein the sterilized fetal support tissue product is partially or fully released into the individual.

EXAMPLES

Example 1

In this example, an optimal radiation dosage required to achieve sterility of the fetal support tissue product was determined. according to the ISO 11137-1 2006 guidelines, the requirement for development, validation and routine control of a sterilization process for medical devices requires 1) the establishment of a maximum acceptable dose and 2) the establishment of a radiation sterilization dose which is primarily set on bioburden (i.e. initial contamination that described population of active pathogens before sterilization).

The AM samples used in this example were AminioGraft® prepared by the CryoTek™ method. Processing of the AM tissue was aseptically performed under Class II Biological Safety Cabinet using minimal manipulation of the tissue. a brief description of the preparation is as follows. Frozen placenta was thawed under controlled conditions and the amniotic membrane (AM) was isolated from the placenta. The AM was further separated from the chorion. The AM was then subjected to a series of steps: 1) Wash PBS 1×+Antibiotics; 2) Gently remove blood from stromal side of AM; 3) Wash PBS 1×+Antibiotics (Soak+Gentle Massage Optional (if blood still present)); 4) Repeat wash until tissue is cleaned to its entirety; 5) Wash PBS 1×+Antibiotics, Swirl and let sit—1 min; 6) Wash PBS 1×+Antibiotics, Swirl and let sit—1 min; 7) Wash PBS 1×—Let Sit; 8) Wash PBS 1×+Antibiotics. AM was then placed on sterile polyethersulfone (PES) membrane with stromal side down and the tissue graft was cut according to size. The tissue grafts were then placed in pouches filled with preservation media (1:1 DMEM/Glycerol) and sealed. The products were kept in a deep-freezing cycle (−80° C.) until needed.

1) Maximum Dose Test=30±3 kGy

A maximum dosage of 30 kGy was selected based on the average total bioburden data previously determined for the finished fetal support tissue product (Average bioburden=0 CFU with 3-5 out of 200 lots<8 CFU annually). For the maximum dose test, several fetal support tissue products were subjected to γ-irradiation at 30 kGy to determine if there was any significant damage to product packaging or the fetal support tissue product itself. The objective of this test was to determine if 30 kGy damages the packaging and the biophysical aspects of the AM itself.

The packaging of the product consists of an inner and outer pouch. The inner pouch was made with 48 gauge polyester/4.0 mil polyethylene (Technipaq INC; product 456). The outer pouch was made with High Barrier Foil Laminate (Technipaq INC; product TL-460).

To determine if the package was damaged ($1^{St}$ and $2^{nd}$ Pouch), the seams of the package were inspected prior and after sterilization. Photographs were taken and the peel strength of each pouch was compared. Peel strength was categorized as Excellent, Good or Poor with the Excellent being a perfect comparison to the current AM product Peel Strength. A 'Good' peel strength is still acceptable but a 'Poor' peel strength is unacceptable and requires further evaluation of the pouching system. Both the inner pouch and outer pouch had already passed the aerosol challenge test and physical challenge (burst) test. All inner and outer samples tested received an Excellent rating in the peel strength test. all sample packaging for AM did not show any signs of biophysical damage. This result was expected as both the inner pouch and outer pouch had been validated by its manufacturer to be compatible with γ-irradiation.

To determine if the biophysical aspects of the AM had been changed, physical manipulation of the AM was used. Briefly, the AM was stretched and folded with forceps before and after irradiation to determine if any physical characteristic changes (e.g. brittleness, discoloration, adherence to backing) occurred during γ-irradiation. Physical manipulation was categorized as Excellent, Good or Poor with the Excellent being a perfect comparison to the physical characteristics of the current commercial AM product. A 'Good' product is still acceptable biophysically but a 'Poor' product is unacceptable. All AM samples tested received an Excellent rating in the physical manipulation test. The physical manipulation test conducted on γ-irradiated AM showed no noticeable deviation in its physical form and characteristics (color & clarity) compared to the non-irradiated samples.

2) Substantiation of $VD_{max}^{25}$

According to the ISO 11137-1 2006 guidelines, bioburden information of the product can be used to substantiate a chosen radiation dose such as 25 kGy ($VD_{max}^{25}$). The advantage of the $VD_{max}$ method is that it requires less product samples. However, the limitation of $VD_{max}$ is that the dose cannot be lowered, even if the bioburden is extremely low. If one chooses to substantiate a protocol using $VD_{max}^{25}$, for example, the validated dose must be 25 kGy, even if the bioburden was zero. In practice, 25 kGy is routinely used in many tissue banks.

A sterilization dose of 25 kGy or 15 kGy was selected and substantiated. The methods for $VD_{max}^{25}$ and $VD_{max}^{15}$ are linked to a Sterility Assurance Level (SAL) of $10^{-6}$ (sample size, n=10). SAL refers to the probability of viable microorganisms (pathogens) present in a product after sterilization. FDA recognizes products with a SAL $10^{-6}$ as a sterile product. The $VD_{max}^{25}$ validation method is applicable to products having an average bioburden less than or equal to 1,000 CFUs (colony forming units) per unit. The $VD_{max}^{15}$ validation method is applicable to products having an average bioburden less than or equal to 1.5 CFUs (colony forming units) per unit. The $VD_{max}^{11.9}$ validation method is applicable to products having an average bioburden less than or equal to 0.2 CFUs (colony forming units) per unit.

The VDmax validation method typically is employed when the sample size is small. Because the production run of each placenta lots only yield ~100 pieces of AM, the VDmax validation method was necessary. The bioburden data indicated that the average bioburden data for AM was 0 cfu, which is within range of both the $VD_{max}^{25}$ and $VD_{max}^{15}$. Even in the event of a positive microsample, the bioburden sample has never been above 8 CFU, which still falls safely within $VD_{max}^{25}$ bioburden range. Table 2 presents the results obtained from the substantiation of $VD_{max}^{25}$ for amniotic membrane tissue product.

TABLE 2

Substantiation of $VD_{max}^{25}$ for Amniotic Membrane

| Term | Value | Comment |
|---|---|---|
| Stage 1 | | |
| SAL | $10^{-6}$ | The method substantiates 25 kGy as a sterilization dose to achieve maximally an SAL of $10^{-6}$ |
| SIP | 1.0 | The product size was ready for performance tests of sterility. The whole AM piece was selected for testing. AM size 2.0 × 2.0 cm was used throughout to satisfy the surface area calculation for SIP |
| Number of Product Items | 40 | 10 from each 3 batches for bioburden determination plus 10 for verification dose experiment. |
| Stage 2 | | |
| Overall SIP average bioburden | 0 | SIP bioburdens of N/A were observed for 3 batches tested for an overall SIP average bioburden of N/A. The historical data shows that average bioburden ~0 cfu and even if it is positive for micro it is always <8 cfu. |

TABLE 2-continued

Substantiation of $VD_{max}^{25}$ for Amniotic Membrane

| Term | Value | Comment |
|---|---|---|
| Overall average bioburden | 0 | The average bioburden for the entire product of each of the batches was calculated:<br>N/A/1.0 = N/A<br>N/A/1.0 = N/A<br>The overall average bioburden was N/A. None of the individual batch average bioburdens was twice the overall average bioburden, therefore the overall average bioburden was used to calculate the verification dose.<br>Stage 3 |
| Verification dose | 0.0 kGy | Table 9 of ISO 11137-2 2006 guideline was used to obtain the verification dose. A bioburden of 0 is not listed in the table so the next higher bioburden of ≤0.1 was used, The $VD_{max}^{25}$ dose for an SIP of 1.0 was calculated using the following equation:<br>SIP $VD_{max}^{25}$ = (SIP = 1.0 $VD_{max}^{25}$) + (SIP dose reduction factor × log SIP)<br>SIP $VD_{max}^{25}$ = 0.0 kGy + (n/a × log 1) = 0.0 kGy<br>Stage 4 |
| Results of tests of sterility | 0 positives | Highest dose to any item was N/A and the arithmetic mean was N/A. The doses delivered to the product times were within the specified range |
| Sterilization dose | 25 kGy | The tests of sterility results were acceptable as the allowed limit was one positive test. Therefore 25 kGy was substantiated. |

Example 2

The HC-HA/PTX3 complex (which comprises Petraxin 3 (PTX3) and the heavy chains (HC) of inter alpha trypsin inhibitor (IαI) covalently bound to hyaluronan (HA)) is the active component in AM responsible in part for clinically observed anti-inflammatory and anti-scarring actions of AM. By testing HC-HA/PTX3 stability and activity, the functional requirements set forth by the AM indication before and after sterilization can be verified. In the first experiment, the concentration of HC-HA/PTX3 in cryopreserved AM (50% DMEM+50% glycerol) and umbilical cord AM (UCAM) product was assessed.

In order to establish a baseline HC-HA/PTX3 Assay, the following steps, which minimized experimental errors, were taken to obtain an accurate measure of the HC-HA/PTX3 content in the fetal support tissue product: 1) surface area of AM samples was standardized (Size: 2.0 cm×2.0 cm); 2) weight of fetal support tissue product was measured; 3) protein concentration for each sample was determined; 4) HC-HA/PTX3 data was normalized with the protein concentration.

To get an accurate and reproducible weight measurement, each fetal support tissue product (with nylon membrane backing) was "dried" by slowly placing it face up and face down on a sterile cotton pad (CVS, Cat#606061) before weighing. The average weight of the 2 cm×2 cm AM fetal support tissue product was 39.8±0.3 mg. The average weight of the 2 cm×2 cm UC fetal support tissue product was 840.6±0.6 mg.

AM and UCAM (P-182) kept in preservation media (50% DMEM+50% glycerol) could be stored at room temperature (RT) if the product was sterile. This would be advantageous since AM in its native environment is kept at body temperature and would eliminate the need to keep the product frozen. The currently available fetal support tissue product is not terminally sterilized. Thus, the current method of storage of AM product is in a frozen state to inhibit the risk of potential of bacteria growth at RT. In order to show that the cryopreserved and sterilized products are functionally similar (e.g. the HC-HA/PTX3 complex has not degraded in the sterilized sample) the concentration of HC-HA/PTX3 in the samples was compared. a maximum gamma radiation dose of 40 kGy and a radiation sterilization dose of 25 kGy were compared to determine the effect of radiation dosage on HC-HA/PTX3 concentration.

Several radioprotectants which potentially have the ability of preserving the HC-HA/PTX3 complex while undergoing γ-irradiation were identified for testing. The use of a radioprotectant in ionizing radiation methods reduces the deleterious effect of free radicals generated indirectly by the radiation due to the radiolysis of water. The protective effect also increases the resistance of pathogens to radiation. Therefore, selection of a radioprotective composition for its preservation capabilities is balanced with maintaining effective sterilization of the product. Table 3 summarizes exemplary radioprotectants. Some of the radioprotectants identified also are cryoprotectants which help harden water (vitrification). Vitrification prevents the formation of ice crystals which can cause damage to cells during the freezing process. Table 4 summarizes exemplary cryoprotectants and their effects.

TABLE 3

Exemplary Radioprotectants (RPA)

| Radioprotectant | Concentration | Mechanism |
|---|---|---|
| Glycerol | 2.74M<br>0.28M | Glycerol binds (imbibes) and sequesters water distributing it throughout the tissue and as such has been suggested to be a radioprotectant by removing water as a target for gamma rays preventing formation of free radicals. |

TABLE 3-continued

Exemplary Radioprotectants (RPA)

| Radioprotectant | Concentration | Mechanism |
|---|---|---|
| Propylene Glycol (PG) | 11.6M | The penetration of PG involves diffusion and binding, but there is no attenuation of transport as the concentration increased. |
| DMSO | 1.0M | Classic radical scavenger and radioprotective composition. When applied in radioprotective doses, in the absence of any subsequent irradiation, it is highly toxic in animals. |
| Glucose | 100 mM | γ-irradiation reduces crosslink density and fragmentation of collagen (for tendon tissue). Glucose forms exogenous crosslinks in collagen during irradiation. |
| Glutathione (GSH) | 0.1M 0.01M | Radical scavenging, restoration of damaged molecules by hydrogen donation, reduction of peroxides and maintenance of thiols in reduced state. Hydrogen donation to DNA radicals most important. Oxidized GSH best used in frozen insulin solution. |
| Ascorbic Acid (Sodium Ascorbate, Ascorbic Acid Glycoside) | 0.34M 0.2M 0.1M | The most powerful and least toxic of natural antioxidants, it is water-soluble and is found in high concentrations in many tissues. Used in conjunction with aqueous insulin. AA best used in aqueous insulin solution. |
| Rosmarinic Acid (RO) | 3 mM | Free radical scavenger. RO has a number of interesting biological activities, including antiviral, antibacterial, anti-inflammatory and antioxidant effects. |
| Mannitol (MA) | 0.28M 0.5M | Sugar alcohol acts as a free radical scavenger to sequester radicals and limit their damage. |
| Riboflavin | 100 mM | |
| Cocktail 1 (PG-USP, DMSO-USP, Mannitol USP, Trehalose) | 2.2M PG, 3.1M DMSO, 150 mM Mannitol, 100 mM trehalose | Cocktail added for 4 hours at 40° C. with gentle agitation. |

TABLE 4

Exemplary Cryoprotectants (CPA)

| Cryoprotectant | Concentration | Mechanism |
|---|---|---|
| Glycerol | 6.85M | Anti-freezing agent that reduces ice formation and lowers freezing point. |
| DMSO | 1.5M (Saline) 1.4M (PBS) | DMSO passes through cell membranes more readily than glycerol, but can be more toxic at higher temperatures. Usually given in gradually increasing concentrations to give time for equilibration to prevent osmotic damage |
| Propylene Glycol (PG), Ethylene Glycol (EG) | 0.82M (PG) 1.1M (EG) | Ethylene glycol - automobile anti-freeze Propylene glycol - formerly used to reduce ice formation in ice cream & preserve human embryo |
| Glucose | 200-500 mM | Northern frogs use glucose as a cryoprotectant. |
| Sucrose (Fructose, Glucose) | 0.5M | Sucrose is the most common sugar found in freezing-tolerant plants which can increase their sucrose levels ten-fold in response to low temperature. Sucrose and trehalose inhibit the membrane mixing associated with chilling but only protect the inner cell membranes of organisms that synthesize them. |
| Trehalose (Glucose, Glucose) | 0.45M 1.61M | Trehalose constitutes 20% of the dry weight of organisms able to survive complete dehydration. Trehalose protects cells and proteins from oxidative damage, whereas sucrose does not. Enhances thermotolerance and reduces aggregation of denatured proteins by acting as a free radical scavenger. |
| Dimethylamine (DMA) | 2.12M | Cryoprotectant for spermatozoa of rainbow trout, small abalone and rooster. |
| Mannitol | 15.0M | Mannitol found to prevent PLGAmPEG nanoparticle aggregation upon lyophilization. Also combined with sucrose at weight ratio 1:0.8:0.6 (phospholipids:mannitol:sucrose) to protect polymyxin E sulfate liposome during freeze-drying. Prevents aggregation and oxidation of alpha-2a (IFNalpha2a) particles during drying. 1:20:100 (w/w) |

TABLE 4-continued

Exemplary Cryoprotectants (CPA)

| Cryoprotectant | Concentration | Mechanism |
|---|---|---|
| Polyvinylpyrrolidone (PVP) | 0.05M | Cryoprotectant for porcine preadipocytes |
| Sorbitol | 2.0M | A non-permeating cryoprotectant used to protect yeast cells with concentration of 2M in hypertonic solution. Act as lyoprotectant for IgG1 antibody when combined with sucrose |

An initial experiment was performed to determine the effect of γ-irradiation on AM or UCAM and its active ingredient with or without the presence of cryoprotective agent (CPA)/radioprotective composition (RPA). For the first experimental trial, the radiation dosage was set at 30 kGy to determine the maximal dosage for the fetal support tissue product. All of the AM used for the trial were processed from a single lot to prevent donor variability of the active ingredients. The AM was prepared in a Class 100 000 R&D Lab using an established AM preparation protocol (Cryotek method (see above)) and a UCAM preparation protocol. The AM tissues were cut to uniform size (2.0 cm×2.0 cm).

Three pieces of fetal support tissue product (AM or UCAM) were kept in 50% DMEM+50% Glycerol while 24 other pieces of fetal support tissue product (AM or UCAM) were allocated for post-processing incubation with CPA/RPA to determine their radioprotective effect on AM. The concentration of CPA and RPA was set at 0.45M in 1X PBS. Because the tissues are not sterilized at this stage of processing yet, the AM products were kept at −80° C. while the preparation for CPA/RPA incubation was done at 4° C. This minimized the risk of potential microorganism growth. Table 5 lists the CPA/RPA conditions tested.

TABLE 5

List CPA/RPA Tested

| AM/UCAM Additives | Concentration (M) | Solution | Manufacturer | Cat. No. |
|---|---|---|---|---|
| 1. Glycerol* | 6.85M (50%) | DMEM | Cellgro | 99971CVC |
| 2. Trehalose | 0.45M (10%) | PBS 1X | Spectrum Chemicals | T1097 |
| 3. Glycerol | 0.45M (3.3%) | PBS 1X | Fisher | BP229-1 |
| 4. DMSO | 0.45M (3.2%) | PBS 1X | Sigma | D2650 |
| 5. Mannitol | 0.45M (5.5%) | PBS 1X | Sigma | M-9546 |
| 6. Propylene Glycol (PG) | 0.45M (3.3%) | PBS 1X | Spectrum Chemicals | P1456 |

*denotes the control AM

The CPA/RPA solution was prepared by mixing required amount of CPA/RPA into 50 ml of 1×PBS. The CPA/RPA solution was mixed using a Mini Vortexer (VWR Scientific) at medium speed for 30 seconds. The CPA/RPA solution was then homogenized using a mixer at 4° C. for 2 hours. Three pieces of processed AM (2.0×3.0 cm) were soaked in a 100 ml culture dish with the CPA/RPA solution. The edges of culture dish were wrapped with Parafilm and placed at 4° C. for 16 hours overnight with mild agitation using a maxi rotator (Labline). After incubation, the AM samples were weighed and individually pouched without media in a clear inner pouch with a heat sealer. The inner pouch was then sealed in a second outer foil pouch. Table 6 lists the AM samples used in the assay and their respective weights. Table 7 lists the UCAM samples used in the assay and their respective weights.

TABLE 6

AM Samples Prior to Sterilization

| AM | | Weight (g) | Comment |
|---|---|---|---|
| 1. Glycerol (50%) | a | 0.130 | 10 ml |
| | b | 0.099 | 10 ml |
| | c | 0.102 | Not Sterilized (10 ml) |
| | d | 0.130, 0.109 | Not Sterilized (10 ml) |
| | e | 0.112, 0.143 | 10 ml |
| | f | 0.132, 0.098 | w/o 10 ml |
| | g | 0.163, 0.107 | Not Sterilized (w/o 10 ml) |
| | h | 0.102, 0.102 | w/o 10 ml |
| 2. Trehalose | a | 0.086 | |
| | b | 0.098 | |
| | c | 0.136 | |
| 3. Glycerol | a | 0.084 | |
| | b | 0.065 | |
| | c | 0.102 | |
| 4. DMSO | a | 0.075 | |
| | b | 0.076 | |
| | c | 0.090 | |
| 5. Mannitol | a | 0.089 | |
| | b | 0.067 | |
| | c | 0.064 | |
| 6. PG | a | 0.093 | |
| | b | 0.099 | |
| | c | 0.103 | |
| 7. Control (AM w/o Sterilization) | a | 0.101 | |
| | b | 0.104 | |
| | c | 0.087 | |

TABLE 7

UCAM Samples Prior to Sterilization

| UCAM | | Weight (g) | Comment |
|---|---|---|---|
| 8. Glycerol (50%) | a | 0.885 | |
| | b | 1.070 | |
| | c | 0.941 | |
| 9. Trehalose | a | 1.234 | |
| | b | 0.539 | |
| | c | 1.102 | |
| 10. Glycerol | a | 0.700 | |
| | b | 0.834 | |
| | c | 0.498 | |
| 11. DMSO | a | 1.123 | |
| | b | 1.112 | |
| | c | 0.588 | |
| 12. Mannitol | a | 0.693 | |
| | b | 1.003 | |
| | c | 1.495 | |
| 13. PG | a | 0.960 | |
| | b | 0.533 | |
| | c | 0.601 | |
| 14. Control (UCAM w/o Sterilization) | a | 1.001 | |
| | b | — | Used for 39b |
| | c | 0.448 | |
| | d | 0.650 | 10 ml |
| | e | 0.694 | 10 ml |

A second set of samples was prepared to test the effects of lyophilization of the fetal support tissue product prior to sterilization. The AM and UCAM samples were prepared in CPA/RPA solution as described above and weighed. After incubation, the samples were lyophilized at −46° C. for 16 hours at 0.035 mBar (26.3 millitorr) (Labconco Freezone 4.5). Following lyophilization, the lyophilized samples were weighed and individually pouched without media in a clear inner pouch with a heat sealer. The inner pouch was then sealed in a second outer foil pouch. Table 8 lists the AM samples used in the assay and their respective weights before and after lyophilization. Table 9 lists the UCAM samples used in the assay and their respective weights before and after lyophilization.

TABLE 8

AM Samples Prior to Sterilization (Weight Before and After Lyophilization)

| AM | | Weight (g) Wet | Lyo | Comment |
|---|---|---|---|---|
| 29. Glycerol (50%) | a | 0.109 | 0.065 | |
|  | b | 0.098 | 0.067 | |
|  | c | 0.084 | 0.053 | |
| 30. Trehalose | a | 0.074 | 0.038 | |
|  | b | 0.099 | 0.040 | |
|  | c | 0.103 | 0.038 | |
| 31. Glycerol | a | 0.065 | 0.021 | |
|  | b | 0.075 | 0.029 | |
|  | c | 0.066 | 0.024 | |
| 32. DMSO | a | 0.074 | 0.028 | |
|  | b | 0.066 | 0.021 | |
|  | c | 0.085 | 0.031 | |
| 33. Mannitol | a | 0.077 | 0.028 | |
|  | b | 0.097 | 0.029 | |
|  | c | 0.068 | 0.025 | |
| 34. PG | a | 0.085 | 0.022 | |
|  | b | 0.131 | 0.026 | |
|  | c | 0.063 | 0.026 | |
| 35. Control (AM Lyo w/o Steri) | a | 0.104 | 0.066 | |
|  | b | 0.102 | 0.071 | |
|  | c | 0.084 | 0.055 | |

TABLE 9

UCAM Samples Prior to Sterilization (Weight Before and After Lyophilization)

| UCAM | | Weight (g) Wet | Lyo | Comment |
|---|---|---|---|---|
| 36. Glycerol (50%) | a | 0.878 | 0.426 | Doesn't Dry (Stays Translucent) |
|  | b | 1.035 | 0.506 | |
|  | c | 0.917 | 0.475 | |
| 37. Trehalose | a | 1.283 | 0.244 | Crystalline Like |
|  | b | 0.798 | 0.185 | |
|  | c | 0.986 | 0.187 | |
| 38. Glycerol | a | 0.996 | 0.090 | |
|  | b | 0.926 | 0.079 | |
|  | c | 0.735 | 0.072 | |
| 39. DMSO | a | — | — | |
|  | b | 0.712 | 0.059 | |
|  | c | 0.531 | 0.048 | |
| 40. Mannitol | a | 1.026 | 0.081 | |
|  | b | 0.958 | 0.056 | |
|  | c | — | — | |
| 41. PG | a | 0.807 | 0.066 | |
|  | b | 0.892 | 0.068 | |
|  | c | 0.776 | 0.059 | |
| 42. Control (UCAM Lyo w/o Steri) | a | — | — | Not enough sample to conduct this study. |
|  | b | — | — | |
|  | c | — | — | |

The prepared pouched samples were then irradiated at 30 kGy. The cryopreserved product was kept on dry ice for duration of the irradiation procedure. The samples were irradiated in a C-cell irradiator at 30 kGy. Dosimeters were employed to calculate the delivered radiation dose. An average dosage of 30 kGy was delivered to the samples.

Following irradiation, protein concentration and HC-HA/PTX3 content were analyzed. Because of the difference in weights between the various AM samples, the tissues were first homogenized in a minimum total volume of 100 µl to obtain protein concentration data. Homogenization was performed using a Bullet Blender 24 in a 4° C. fridge at speed level 10 for 5 minutes and an additional 5 minutes. The homogenized samples were then spun in a centrifuge at 4° C. and 15 000 rcf. Both the AM and lyophilized AM samples were homogenized completely, but UCAM and lyophilized UCAM samples did not homogenize completely. a visual check revealed that most of the UCAM remained intact after a complete homogenization run using the BulletBlender. This was due to the thickness of the UCAM which ranges from 400-900 µm compared to the thickness of AM which only ranges from 100-300 µm. Because the samples were processed identically, equivalent samples of the partially homogenizes UCAM extracts were isolated and assayed.

HC-HA/PTX3 concentration was then normalized. Protein concentration was measured using 40 µl of the homogenized extract and a standard BCA protein assay (Pierce (Rockford, Ill.) Cat. No. 23225). HC-HA/PTX3 content was assessed by (ELISA) in a 96-well plate. AM homogenized extracts were sampled at 1:5 dilution (20 µl volume) in duplicate and run with HC-HA/PTX3 standards to determine HC-HA/PTX3 concentration. an HA concentration assay was then performed using the same 96 well plate. The plates were washed four times with 300 µl 1×PBS. Then 100 µl of HRP-conjugated HABP solution was added to the wells. HA concentration was then determined according to the manufacturer's instructions. (HA Quantitative Test Kit Corgenix (Westminster, Colo.) Product: 029-001).

The ELISA was performed according to the following procedure: AM extracts or HC·HAs were with the reaction buffer (from HA Kit). The diluted sample solution (100 µl) was added to HA coated 96 wells in duplicate and incubated for 2 hours at room temperature. The solution was removed and the wells were washed 4 times with PBS. The wells were blocked with 150 µl of 2.5% skim milk in PBS at room temperature for 1 h, and then the blocking solution was removed. 100 µl of anti-IαI antibody (Rabbit anti-IαI polyclonal antibody (DAKO, A0301)) was added to each of wells and incubated 60 minutes at room temperature. The wells were then washed 4 times with PBS. 100 µl of HRP-conjugated the secondary antibody was then added to each of wells and incubated 60 minutes at room temperature. The wells were then washed 4 times with PBS and 100 µl one-component Substrate solution (from HA Kit) was added to each well and incubated for 30 minutes. 100 µl Stop solution (from HA Kit) was added to each well to stop enzyme reaction. The O.D of each well was read at 450 nm (650 nm reference) and the concentration was calculated based on standard samples of HA (Hyaluronic acid sodium salt, from human umbilical cord (Sigma, Cat#H1876) and Healon® (51-0050-00, UD30256, Advanced Medical Optics-AMO, Santa Ana, Calif.).

Tables 10, 11 and 12 depict the average weight, average protein concentration, average HA concentration and average HC-HA/PTX3 concentration of the AM, AM lyophilized (AM lyo) and UCAM γ-irradiated samples, respectively. Due to the limited amount of lyophilized UCAM samples, analysis of the UCAM lyo data was not performed as there were no controls available for that category.

As expected, the protein concentration for the non-irradiated samples (control) of AM and lyophilized AM was higher (353 µg/ml and 261 µg/ml, respectively) compared to the samples that had undergone γ-irradiation. This trend also was observed in the HC-HA/PTX3 concentration data where the results for the non-irradiated samples (control) of AM, lyophilized AM and UCAM (336 ng/ml, 188 ng/ml and 216 ng/ml, respectively) was higher compared to the samples that has undergone γ-irradiation. This finding correlated with previous studies which concluded that γ-irradiation damages various chemical and molecular bonds. This study revealed that γ-irradiation does indeed damage biological properties of the AM, since HC-HA/PTX3 is one of the active ingredients contributing to the therapeutic and biological function of AM.

The average concentration of HA for the non-irradiated samples (control) is lower than some of its gamma irradiated samples for all 3 samples categories. This is clearly delineated in data for AM where the non-irradiated sample has an average HA concentration of 179 ng/ml compared to readings above 200 ng/ml for all AM samples which had been irradiated under various conditions.

An independent one tailed T-Test was conducted to determine if there was a significant difference between the non-irradiated samples (control) and the irradiated samples preserved under varying conditions for each category. An independent T-Test was selected as there are two groups of samples that are independent of one another. One-tail was selected as it was predicted that the values for the non-irradiated samples would be higher than the data for the irradiated samples. The threshold chosen for statistical significance was <0.05.

All the P-values recorded in Table 10 are >0.05 indicating that none of the irradiated samples are significantly different than the non-irradiated samples in terms of protein concentration, HA concentration and HC-HA/PTX3 concentration. However, a cell by cell analysis of Table 10 revealed deviation in some of the data set. One such example is the total protein concentration data for 0.45M Glycerol and 0.45M Mannitol which was recorded at 149 µg/ml and 95 µg/ml respectively compared to 354 µg/ml of the non-irradiated control. This 58% and 73% drop in protein concentration for 0.45M Glycerol and 0.45M Mannitol, respectively, showed that these two radioprotectants were the weakest in protecting AM proteins undergoing γ-irradiation. This trend continued for 0.45M Mannitol in protecting HC-HA/PTX3 where the concentration of HC-HA/PTX3 was recorded at 36 ng/ml compared to 336.43 ng/ml for the control (non-irradiated AM). 0.45M Glycerol, though, showed notable protective ability for HC-HA/PTX3 with a HC-HA/PTX3 concentration of 216 ng/ml and was only slightly less effective than 0.45M Propylene Glycol (HC-HA/PTX3 concentration reading of 302 ng/ml) in terms of protecting AM's active ingredient. The data based on HC-HA/PTX3 concentration was given more weight in the study since HC-HA/PTX3 as one of the active ingredients in AM.

Based on Table 10, the agents that protect cryopreserved AM best during γ-irradiation according to rank are: 0.45M Propylene Glycol>0.45M Glycerol>0.45M DMSO. 0.45M Mannitol provided the least protection for cryopreserved AM undergoing γ-irradiation.

TABLE 10

Data for AM and Rank of Each Cryo/Radio-protectant

| Content | Avg. Weight (g) | Avg. Protein Conc (ug/ml) | P-value (Protein) | Avg. HA Conc (ng/ml) | P-value (HA) | Avg. HC-HA/PTX3 Conc (ng/ml) | P-value (HC-HA/PTX3) | HC-HA/PTX3 Rank | Overall Rank |
|---|---|---|---|---|---|---|---|---|---|
| 50% Glycerol + 50% DMEM | 0.025 ± 0.004 | 313.024 ± 68.2 | 0.373 | 207.128 ± 40.2 | 0.355 | 126.821 ± 36.4 | 0.165 | 5 | 2 |
| 0.45M Trehalose | 0.027 ± 0.005 | 251.334 ± 49.5 | 0.221 | 209.895 ± 56.2 | 0.349 | 159.550 ± 96.4 | 0.199 | 4 | 4 |
| 0.45M Glycerol | 0.020 ± 0.006 | 148.904 ± 127 | 0.099 | 275.659 ± 83.3 | 0.149 | 216.386 ± 30.4 | 0.271 | 2 | 5 |
| 0.45M DMSO | 0.023 ± 0.004 | 204.377 ± 182 | 0.187 | 200.274 ± 46.7 | 0.391 | 163.767 ± 65.7 | 0.203 | 3 | 1 |
| 0.45M Mannitol | 0.021 ± 0.006 | 94.869 ± 3.3 | 0.068 | 208.020 ± 75.2 | 0.376 | 36.372 ± 27.8 | 0.104 | 6 | 6 |
| 0.45M Propylene Glycol | 0.025 ± 0.003 | 226.427 ± 58.4 | 0.178 | 232.114 ± 58.9 | 0.258 | 302.321 ± 334 | 0.450 | 1 | 3 |
| Non-irradiated (50% Gly/DMEM) | 0.027 ± 0.007 | 353.560 ± 185 | N/A | 179.160 ± 110.6 | N/A | 336.43 ± 285 | N/A | N/A | N/A |

TABLE 11

Data for Lyophilized AM and Rank of Each Cryo/Radio-protectant

| Content | Average Weight (g) | Average Protein Conc (ug/ml) | P-value (Protein) | Average HA Conc (ng/ml) | P-value (HA) | Average HC-HA/PTX3 Conc (ng/ml) | P-value (HC-HA/PTX3) | HA Rank | Overall Rank |
|---|---|---|---|---|---|---|---|---|---|
| 50% Glycerol + 50% DMEM | 0.016 ± 0.006 | 82.989 ± 35.4 | 0.238 | 357.347 ± 55.0 | 0.014 | 157.459 ± 123 | 0.424 | 2 | 4 |
| 0.45M Trehalose | 0.017 ± 0.004 | 48.766 ± 56.5 | 0.204 | 162.125 ± 22.2 | 0.040 | 42.275 ± 55.4 | 0.183 | 6 | 6 |
| 0.45M Glycerol | 0.013 ± 0.003 | 79.916 ± 67.2 | 0.235 | 204.126 ± 15.9 | 0.453 | 84.996 ± 75.7 | 0.253 | 3 | 2 |
| 0.45M DMSO | 0.017 ± 0.004 | 145.428 ± 127 | 0.319 | 266.741 ± 60.3 | 0.099 | 162.88 ± 72.0 | 0.433 | 1 | 1 |
| 0.45M Mannitol | 0.014 ± 0.003 | 107.761 ± 87.1 | 0.267 | 145.9 ± 15.1 | 0.010 | 62.565 ± 69.6 | 0.214 | 5 | 5 |
| 0.45M Propylene Glycol | 0.011 ± 0.001 | 89.461 ± 72.8 | 0.246 | 170.044 ± 68.2 | 0.252 | 64.230 ± 60.3 | 0.216 | 4 | 3 |
| Non-irradiated (50% Gly/DMEM) | 0.015 ± 0.003 | 260.986 ± 354 | N/A | 202.274 ± 19.6 | N/A | 187.550 ± 217.2 | N/A | N/A | N/A |

The P-values calculated in Table 11 for HA concentration of 50% DMEM/50% Glycerol, 0.45M Glycerol and 0.45M Mannitol (0.014, 0.040 & 0.010 respectively) showed that there are significant differences between the lyophilized AM samples kept in their respective conditions compared to the non-irradiated lyophilized AM control. A review of the actual HA concentration however showed that the HA concentration of 50% DMEM/50% Glycerol (357 ng/ml) was higher than the lyophilized AM control's HA concentration (202 ng/ml). The only inference drawn was that 50% DMEM/50% Glycerol has no reduced efficiency in protecting lyophilized AM's protein during γ-irradiation. This observation was further supported using 50% DMEM/50% Glycerol HC-HA/PTX3 data where HC-HA/PTX3 concentration was recorded at 157 ng/ml compared to 188 ng/ml for the non-irradiated lyophilized AM control. The best HC-HA/PTX3 protection was provided by 0.45M DMSO with a concentration reading 163 ng/ml.

Based on Table 11, the agents that protect lyophilized AM best during γ-irradiation according to rank are: 0.45M DMSO>50% DMEM/50% Glycerol>0.45M Propylene Glycol. 0.45M Mannitol and 0.45M Trehalose provided the least protection for cryopreserved lyophilized AM undergoing γ-irradiation.

TABLE 12

| Data for UCAM and Rank of Each Cryo/Radio-protectant | | | | | | | | | |
|---|---|---|---|---|---|---|---|---|---|
| Content | Average Weight (g) | Average Protein Conc (ug/ml) | P-value (Protein) | Average HA Conc (ng/ml) | P-value (HA) | Average HC-HA/PTX3 Conc (ng/ml) | P-value (HC-HA/PTX3) | HC-HA/PTX3 Rank | Overall Rank |
| 50% Glycerol + 50% DMEM | 0.057 ± 0.010 | 1088.465 ± 278 | 0.013 | 225.575 ± 38.3 | 0.261 | 0 ± 0 | 0.032 | 6 | 6 |
| 0.45M Trehalose | 0.058 ± 0.003 | 361.893 ± 86.8 | 0.315 | 222.112 ± 61.7 | 0.273 | 12.756 ± 22.1 | 0.032 | 5 | 3 |
| 0.45M Glycerol | 0.056 ± 0.012 | 312.709 ± 77.3 | 0.487 | 256.870 ± 48.387 | 0.414 | 43.980 ± 39.6 | 0.040 | 1 | 1 |
| 0.45M DMSO | 0.056 ± 0.003 | 179.865 ± 38.5 | 0.097 | 200.210 ± 13.7 | 0.045 | 36.124 ± 39.069 | 0.036 | 3 | 5 |
| 0.45M Mannitol | 0.056 ± 0.000 | 351.517 ± 108 | 0.364 | 153.382 ± 3.03 | 0.015 | 20.530 ± 35.6 | 0.031 | 4 | 4 |
| 0.45M Propylene Glycol | 0.050 ± 0.006 | 230.658 ± 51.3 | 0.182 | 284.422 ± 56.3 | 0.204 | 47.688 ± 82.6 | 0.044 | 2 | 2 |
| Non-irradiated (50% Gly/DMEM) | 0.066 ± 0.003 | 315.791 ± 125 | N/A | 249.105 ± 30.2 | N/A | 215.746 ± 98.9 | N/A | N/A | N/A |

From Table 12, the p-value (0.013) for the protein concentration of 50% DMEM/50% Glycerol (1088 μg/ml) showed a significant difference compared to the concentration of 316 μg/ml for the non-irradiated UCAM control. Because the protein concentration of gamma irradiated UCAM preserved in 50% DMEM/50% Glycerol is higher than the control (non-irradiated UCAM) it was concluded that 50% DMEM/50% Glycerol has no reduced efficiency in protecting UCAM's protein during γ-irradiation. All the p-values for HC-HA/PTX3 concentration of gamma irradiated UCAM showed significant differences (<0.05) compared to its non-irradiated UCAM control. For the UCAM HA concentration, only the p-value 0.45M DMSO and 0.45 Mannitol (0.045 and 0.015, respectively) showed significant difference compared to the control.

Based on the results of Table 12, the agents that protect UCAM best during γ-irradiation according to rank are 0.45 M Glycerol and 0.45M Propylene Glycol. It was also concluded (according to rank) that 0.45M DMSO, 0.45M Mannitol and 50% DMEM/50% Glycerol provided the least protection for cryopreserved UCAM undergoing γ-irradiation.

Table 13 provides a succinct overview of the strong and weak protective agents for AM undergoing γ-irradiation. Propylene Glycol and Glycerol were identified as the stronger agents in protecting AM. In contrast, Mannitol provided the least protection.

TABLE 13

Summary of Strongest and Weakest Cryo/Radio-protectant for Each Category
Protective Efficiency of Radio-agents Against γ-irradiation

| AM | | AM Lyo | | UCAM | |
|---|---|---|---|---|---|
| Stronger | Weaker | Stronger | Weaker | Stronger | Weaker |
| 1) 0.45M Propylene Glycol 2) 0.45M Glycerol 3) 0.45M DMSO | 0.45M Mannitol | 1) 0.45M DMSO 2) 50% DMEM/50% Glycerol 3) 0.45M Propylene Glycol and 0.45M Glycerol | 1) 0.45M Mannitol 2) 0.45M Trehalose | 1) 0.45M Glycerol 2) 0.45M Propylene Glycol | 1) 0.45M DMSO 2) 0.45M Mannitol 3) 50% DMEM/50% Glycerol |

Example 3

In the previous example, Propylene Glycol and Glycerol were identified as cryo/radioprotective compositions of the fetal support tissue product. In this example, the effects of Propylene Glycol and Glycerol concentration on lyophilization of AM on the extractability of AM proteins, HA and HC-HA/PTX3 were examined. AM samples were prepared as described in Example 2. For CPA/RPA incubations, the samples were incubated in DMEM (with +4.5 g/L D-Glucose, with L-Glutamine, with 25 mM HEPES, without Sodium Pyruvate & without Phenol Red (GIBCO, 21063)) containing increasing concentrations of glycerol or propylene glycol according to Table 14. Glycerol (Gly) has a density of 1.261 g/cm$^3$ while Propylene Glycol (PG) has a density of 1.036 g/cm$^3$. The samples were incubated at 4° C. for 16 hours with mild agitation using a Maxi Rotator (Labline). A set of AM samples was prepared without lyophilization and a set of AM samples was prepared with lyophilization (see Example 2). Weight, protein concentration, HA concentration and HC-HA/PTX3 concentration for each sample were determined as described in Example 2.

TABLE 14

Glycerol and Propylene Concentration

| Cryo-Radioprotectant | Concentration | Base Media |
|---|---|---|
| Glycerol (Manufacturer: Fisher, Catalog # BP229-1) | 0% 10% 20% 30% 40% 50% (Cellgro, 99971CVC) | DMEM |
| Propylene Glycol, PG (Manufacturer: Spectrum Chemicals, Catalog # P1456) | 0% 10% 20% 30% 40% 50% | DMEM |

Following incubation, the prepared samples were inspected visually to note differences in size or appearance. AM preserved in Gly without lyophilization progressively shrunk the AM sample as the concentration of Gly increased. AM preserved in PG without lyophilization also progressively shrunk the AM sample as the concentration of PG increased though the effect was less pronounced. Lyophilized AM preserved in Gly (10%-50%) did not dry out as the samples were still transparent after 6 hours of lyophilization. In contrast, lyophilized AM preserved in PG dried out completely for all samples preserved in different concentrations. One possible explanation for this observation is the ability of Gly to imbibe (bind) water thereby, preserving the hydration of AM even though an external force (lyophilization) was used to remove the water.

An independent one tailed T-Test was conducted to determine if there was a significant difference between the AM samples in DMEM (0% Gly or 0% PG aka control) and the samples preserved under varying concentrations of Gly and PG with or without lyophilization. An independent T-Test was selected since there were two groups of samples that are independent of each other. Two-tail was selected it could not be predicted which group would be higher. The threshold chosen for statistical significance was <0.05. Due to the limited amount of lyophilized AM samples, testing was not conducted for 0% AM PG. However, because the base solution for all the 0% samples was the same (DMEM) for both 0% PG and 0% Gly, 0% AM PG was exactly the same as 0% AM Gly, the later results were used to analyze the resulting lyophilized AM with varying PG concentration (10%-50%).

Table 15 shows the AM weight distribution preserved in various concentration of Gly or PG with or without lyophilization. Based on Table 15, the average weight of AM preserved in Gly and PG without lyophilization increases as their respective concentration increases. With this analysis and the observation made on the appearance of the AM, it was concluded that with increasing concentrations, the thickness of the AM tissue increases since the physical size shrinks while the average weight continues to increase. This observation is not as prominent for PG suggesting that PG does not bound water as effectively as Gly. This model assumes that the amount of bounded water that maintains the hydration AM directly correlates to its average weight.

For the AM preserved in Gly with lyophilization, the average weight increases as the concentration increases. The significant difference in weight correlates with the observation of where the AM remains "wet" (for higher concentrations) even though an external force was used (lyophilization) to try and remove the water. In contrast, the average weight of AM preserved in PG with lyophilization did not have a large fluctuation as it ranged between 12.0-13.3 g even with increasing concentration. This finding corresponds with the observation that the AM, irrespective of its PG concentration became dry after undergoing lyophilization. The cross analysis of these data with physical appearance indicates that the mechanism of how Glycerol and PG bound to water and its subsequent incorporation into the AM matrix differ from each other.

lyophilization and Gly with lyophilization (with the exception of 10% Gly without lyophilization and 20% Gly with lyophilization in their respective cases) was observed. Glycerol has been shown to stabilize the native structure of globular proteins. Glycerol induces protein compaction, reduces protein flexibility, stabilizes specific partially unfolded intermediates, and affects both native and non-native protein aggregation.

For AM preserved in PG both with and without lyophilization, the protein concentration increased as the concentration of PG increased until 40% before dropping at 50%. Additionally, lyophilized AM preserved in 10% Gly yielded a negligible amount of protein (1.44 µg/ml) and this finding correlates with the observation that the AM dried out during the lyophilization process compared to the other AM which remains "wet" when lyophilized and preserved in higher concentration of Gly. Unlike Gly, the protein extraction efficiency of PG (concentration) as a whole falls within the same concentration range for both with and without lyophilization.

In sum, in terms of protein extraction efficiency, AM preserved in increasing concentration of Gly yielded increasing amount of protein (highest protein concentration at 50% Glycerol). a similar trend for lyophilized AM preserved in increasing Gly concentration also was observed although the overall protein concentration range (<100 µg/ml) was significantly reduced suggesting a dampening

TABLE 15

Weight of AM and AM Lyo in Varying Concentrations of Gly and PG

| | Content | Average Weight (mg) | Weight St Dev | P-value Weight | | Content | Average Weight (mg) | Weight St Dev | P-value Weight |
|---|---|---|---|---|---|---|---|---|---|
| AM | 0% Gly | 22.67 | 2.1 | n/a | AM | 0% PG | 19.00 | 1.4 | n/a |
| | 10% Gly | 25.33 | 2.3 | 0.212 | | 10% PG | 25.33 | 5.9 | 0.196 |
| | 20% Gly | 20.67 | 1.5 | 0.257 | | 20% PG | 26.00 | 5.6 | 0.153 |
| | 30% Gly | 26.00 | 5.0 | 0.373 | | 30% PG | 22.00 | 2.6 | 0.199 |
| | 40% Gly | 28.00 | 5.3 | 0.216 | | 40% PG | 26.67 | 3.8 | 0.059 |
| | 50% Gly | 32.67 | 8.5 | 0.173 | | 50% PG | 29.33 | 2.1 | 0.008 |
| AM Lyo | 0% Gly | 15.67 | 0.6 | n/a | AM Lyo | 0% PG/ 0% Gly | 15.67 | 0.6 | n/a |
| | 10% Gly | 15.00 | 2.0 | 0.628 | | 10% PG | 12.67 | 1.5 | 0.062 |
| | 20% Gly | 16.00 | 2.0 | 0.804 | | 20% PG | 12.67 | 2.1 | 0.121 |
| | 30% Gly | 19.33 | 1.5 | 0.040 | | 30% PG | 12.00 | 1.0 | 0.010 |
| | 40% Gly | 21.67 | 1.5 | 0.012 | | 40% PG | 13.00 | 1.0 | 0.025 |
| | 50% Gly | 23.00 | 3.0 | 0.047 | | 50% PG | 13.33 | 3.5 | 0.369 |

Table 16 shows the AM protein concentration preserved in various concentration of Gly or PG with or without lyophilization. The only significant deviation (p=0.014) of the protein data was recorded for AM preserved in 50% Gly without lyophilization, yielding 3× higher protein when compared to the control, indicating that 50% glycerol is unique in dissociating protein from ECM and lyophilization dampens such an effect. An increasing trend for the protein concentration of AM preserved in both Gly without effect of extraction efficiency due to lyophilization. Protein extraction efficiency for AM preserved in PG with and without lyophilization were in the protein concentration range of AM preserved in Glycerol with lyophilization (<100 µg/ml). This not only indicated that lyophilization dampens the extraction efficiency of protein but provided an insight that glycerol may preferentially disassociate protein from the matrix of AM during homogenization while preventing them from aggregating.

TABLE 16

Protein Concentration of AM and AM Lyo in Varying Concentrations of Gly and PG

| | Content | Average Protein (ug/ml) | Protein St Dev | P-value Protein | | Content | Average Protein (ug/ml) | Protein St Dev | P-value Protein |
|---|---|---|---|---|---|---|---|---|---|
| AM | 0% Gly | 82.31 | 31.3 | n/a | AM | 0% PG | 85.33 | 58.9 | n/a |
| | 10% Gly | 132.34 | 107.2 | 0.509 | | 10% PG | 97.70 | 74.0 | 0.850 |
| | 20% Gly | 114.52 | 68.6 | 0.517 | | 20% PG | 97.64 | 95.2 | 0.870 |
| | 30% Gly | 114.68 | 111.4 | 0.670 | | 30% PG | 72.45 | 54.3 | 0.827 |
| | 40% Gly | 163.02 | 102.2 | 0.303 | | 40% PG | 105.40 | 87.7 | 0.780 |
| | 50% Gly | 258.80 | 53.9 | 0.014 | | 50% PG | 80.96 | 70.4 | 0.945 |
| AM Lyo | 0% Gly | 38.21 | 30.5 | n/a | AM Lyo | 0% PG/ 0% Gly | 38.21 | 30.5 | n/a |
| | 10% Gly | 1.44 | 2.5 | 0.172 | | 10% PG | 46.14 | 35.6 | 0.784 |
| | 20% Gly | 64.76 | 50.8 | 0.490 | | 20% PG | 54.88 | 64.1 | 0.713 |
| | 30% Gly | 47.39 | 15.7 | 0.675 | | 30% PG | 70.26 | 17.7 | 0.208 |
| | 40% Gly | 54.08 | 8.2 | 0.466 | | 40% PG | 139.00 | 185.3 | 0.446 |
| | 50% Gly | 93.44 | 69.1 | 0.302 | | 50% PG | 89.72 | 136.0 | 0.582 |

Table 17 shows that there was no significant difference (all p-values >0.05) in the HA concentration recorded for AM preserved in Gly or PG with or without lyophilization, indicating that HA is readily extractable due to its water-soluble property and such a property is not affected by lyophilization. The HA concentration of AM preserved in Gly without lyophilization showed an increasing trend as the concentration of Gly increased until 40% before dropping, indicating that glycerol helps dissociate HA-containing ECM so that both HA and protein are more easily extracted. There were no trends observed for the remainder of the conditions but the conditions that yielded the most HA in each of their respective categories were 40% PG without lyophilization, 30% Gly with lyophilization and 50% PG with lyophilization.

TABLE 17

HA Concentration of AM and AM Lyo in Varying Concentrations of Gly and PG

| | Content | Average HA (ng/ml) | HA St Dev | P-value HA | | Content | Average HA (ng/ml) | HA St Dev | P-value HA |
|---|---|---|---|---|---|---|---|---|---|
| AM | 0% Gly | 267.84 | 130.0 | n/a | AM | 0% PG | 217.39 | 0.6 | n/a |
| | 10% Gly | 109.16 | 95.8 | 0.171 | | 10% PG | 291.58 | 97.2 | 0.317 |
| | 20% Gly | 172.01 | 27.8 | 0.329 | | 20% PG | 204.70 | 73.7 | 0.794 |
| | 30% Gly | 213.19 | 29.2 | 0.545 | | 30% PG | 203.80 | 39.0 | 0.608 |
| | 40% Gly | 238.16 | 128.6 | 0.793 | | 40% PG | 308.24 | 90.7 | 0.225 |
| | 50% Gly | 219.94 | 27.5 | 0.592 | | 50% PG | 237.98 | 69.2 | 0.658 |
| AM Lyo | 0% Gly | 245.02 | 40.7 | n/a | AM Lyo | 0% PG/ 0% Gly | 245.02 | 40.7 | n/a |
| | 10% Gly | 286.61 | 77.9 | 0.472 | | 10% PG | 230.57 | 31.9 | 0.655 |
| | 20% Gly | 254.07 | 87.6 | 0.882 | | 20% PG | 224.82 | 18.8 | 0.495 |
| | 30% Gly | 294.83 | 80.0 | 0.408 | | 30% PG | 197.33 | 43.2 | 0.237 |
| | 40% Gly | 263.09 | 35.6 | 0.594 | | 40% PG | 237.44 | 30.0 | 0.809 |
| | 50% Gly | 228.05 | 123.8 | 0.839 | | 50% PG | 264.59 | 74.8 | 0.716 |

Table 18 shows that there was no significant difference (all p-values >0.05) in the HC-HA/PTX3 concentration recorded for AM preserved in Gly or PG with or without lyophilization. The table shows an increasing trend of HC-HA/PTX3 concentration for both AM preserved in Gly without lyophilization and PG without lyophilization as the concentration of each preservation media increases until 50% (with the exception of 10% Gly without lyophilization). For the lyophilized AM samples, the optimal Gly concentration for HC-HA/PTX3 extraction was 20% while the optimal PG concentration was 50%.

TABLE 18

HC-HA/PTX3 Concentration of AM and AM Lyo in Varying Concentrations of Gly and PG

| | Content | Average HC-HA/PTX3 (ng/ml) | HC-HA/PTX3 St Dev | P-value HC-HA/PTX3 | | Content | Average HC-HA/PTX3 (ng/ml) | HC-HA/PTX3 St Dev | P-value HC-HA/PTX3 |
|---|---|---|---|---|---|---|---|---|---|
| AM | 0% Gly | 166.60 | 236.8 | n/a | AM | 0% PG | 76.51 | 66.0 | n/a |
| | 10% Gly | 37.55 | 11.4 | 0.450 | | 10% PG | 45.75 | 30.3 | 0.628 |

TABLE 18-continued

HC-HA/PTX3 Concentration of AM and AM Lyo in Varying Concentrations of Gly and PG

|  | Content | Average HC-HA/PTX3 (ng/ml) | HC-HA/PTX3 St Dev | P-value HC-HA/PTX3 |  | Content | Average HC-HA/PTX3 (ng/ml) | HC-HA/PTX3 St Dev | P-value HC-HA/PTX3 |
|---|---|---|---|---|---|---|---|---|---|
|  | 20% Gly | 16.12 | 12.0 | 0.386 |  | 20% PG | 71.59 | 19.7 | 0.934 |
|  | 30% Gly | 57.51 | 3.9 | 0.509 |  | 30% PG | 82.32 | 64.6 | 0.931 |
|  | 40% Gly | 85.16 | 70.9 | 0.618 |  | 40% PG | 86.20 | 83.9 | 0.895 |
|  | 50% Gly | 140.98 | 184.6 | 0.890 |  | 50% PG | 142.28 | 97.9 | 0.437 |
| AM Lyo | 0% Gly | 74.91 | 84.9 | n/a | AM Lyo | 0% PG/ 0% Gly | 74.91 | 84.9 | n/a |
|  | 10% Gly | 67.32 | 93.4 | 0.922 |  | 10% PG | 12.06 | 20.9 | 0.328 |
|  | 20% Gly | 118.37 | 56.6 | 0.507 |  | 20% PG | 9.64 | 16.7 | 0.314 |
|  | 30% Gly | 60.83 | 42.9 | 0.815 |  | 30% PG | 4.51 | 7.8 | 0.287 |
|  | 40% Gly | 25.05 | 43.4 | 0.432 |  | 40% PG | 6.77 | 11.7 | 0.298 |
|  | 50% Gly | 36.58 | 58.2 | 0.558 |  | 50% PG | 76.28 | 29.2 | 0.981 |

A summary of the data from Examples 2 and 3 are presented in Tables 19-26.

TABLE 19

Cryopreserved AM preserved in Gly and PG with or without γ-Irradiation

AM Gamma Irradiated

| Content | Average Weight (mg) | Average Protein (ug/ml) | Average HA (ng/ml) | Average HC-HA/PTX3 (ng/ml) |
|---|---|---|---|---|
| 50% Gly | 25 ± 4 | 313.024 ± 68.2 | 207.128 ± 40.2 | 126.821 ± 36.4 |
| 3.3% Gly | 20 ± 6 | 148.904 ± 127 | 275.659 ± 83.3 | 216.386 ± 30.4 |
| 3.3% PG | 25 ± 3 | 226.427 ± 58.4 | 232.114 ± 58.9 | 302.321 ± 334 |
| Non-irradiated (50% Gly) | 27 ± 7 | 353.560 ± 185 | 179.160 ± 110.6 | 336.43 ± 285 |

AM Non Gamma Irradiated

| Content | Average Weight (mg) | Average Protein (ug/ml) | Average HA (ng/ml) | Average HC-HA/PTX3 (ng/ml) |
|---|---|---|---|---|
| 0% Gly | 22.67 | 82.31 | 267.84 | 166.60 |
| 10% Gly | 25.33 | 132.34 | 109.16 | 37.55 |
| 20% Gly | 20.67 | 114.52 | 172.01 | 16.12 |
| 30% Gly | 26.00 | 114.68 | 213.19 | 57.51 |
| 40% Gly | 28.00 | 163.02 | 238.16 | 85.16 |
| 50% Gly | 32.67 | 258.80 | 219.94 | 140.98 |

AM Non Gamma Irradiated

| Content | Average Weight (mg) | Average Protein (ug/ml) | Average HA (ng/ml) | Average HC-HA/PTX3 (ng/ml) |
|---|---|---|---|---|
| 0% PG | 19.00 | 85.33 | 217.39 | 76.51 |
| 10% PG | 25.33 | 97.70 | 291.58 | 45.75 |
| 20% PG | 26.00 | 97.64 | 204.70 | 71.59 |
| 30% PG | 22.00 | 72.45 | 203.80 | 82.32 |
| 40% PG | 26.67 | 105.40 | 308.24 | 86.20 |
| 50% PG | 29.33 | 80.96 | 237.98 | 142.28 |

TABLE 20

Lyophilized AM preserved in Gly and PG with or without γ Irradiation

AM Lyo Gamma Irradiated

| Content | Average Weight (mg) | Average Protein (ug/ml) | Average HA (ng/ml) | Average HC-HA/PTX3 (ng/ml) |
|---|---|---|---|---|
| 50% Gly | 16 ± 6 | 82.989 ± 35.4 | 357.347 ± 55.0 | 157.459 ± 123 |
| 3.3% Gly | 13 ± 3 | 79.916 ± 67.2 | 204.126 ± 15.9 | 84.996 ± 75.7 |
| 3.3% PG | 11 ± 1 | 89.461 ± 72.8 | 170.044 ± 68.2 | 64.230 ± 60.3 |
| Non-irradiated (50% Gly) | 15 ± 3 | 260.986 ± 354 | 202.274 ± 19.6 | 187.550 ± 217.2 |

TABLE 20-continued

Lyophilized AM preserved in Gly and PG with or without γ Irradiation

AM Lyo Non Irradiated

| Content | Average Weight (mg) | Average Protein (ug/ml) | Average HA (ng/ml) | Average HC-HA/PTX3 (ng/ml) |
|---|---|---|---|---|
| 0% Gly | 15.67 | 38.21 | 245.02 | 74.91 |
| 10% Gly | 15.00 | 1.44 | 286.61 | 67.32 |
| 20% Gly | 16.00 | 64.76 | 254.07 | 118.37 |
| 30% Gly | 19.33 | 47.39 | 294.83 | 60.83 |
| 40% Gly | 21.67 | 54.08 | 263.09 | 25.05 |
| 50% Gly | 23.00 | 93.44 | 228.05 | 36.58 |

AM Lyo Non Irradiated

| Content | Average Weight (mg) | Average Protein (ug/ml) | Average HA (ng/ml) | Average HC-HA/PTX3 (ng/ml) |
|---|---|---|---|---|
| 0% PG | 15.67 | 38.21 | 245.02 | 74.91 |
| 10% PG | 12.67 | 46.14 | 230.57 | 12.06 |
| 20% PG | 12.67 | 54.88 | 224.82 | 9.64 |
| 30% PG | 12.00 | 70.26 | 197.33 | 4.51 |
| 40% PG | 13.00 | 139.00 | 237.44 | 6.77 |
| 50% PG | 13.33 | 89.72 | 264.59 | 76.28 |

TABLE 21

Extraction Efficiency of AM (Gly and PG)

| Content | Average Weight (mg) | P-value Weight | Average Protein (ug/ml) | P-value Protein | Average HA (ng/ml) | P-value HA | Average HC-HA/PTX3 (ng/ml) | P-value HC-HA/PTX3 |
|---|---|---|---|---|---|---|---|---|
| 10% Gly | 25.33 | 1.000 | 132.34 | 0.672 | 109.16 | 0.082 | 37.55 | 0.696 |
| 10% PG | 25.33 | | 97.70 | | 291.58 | | 45.75 | |
| 20% Gly | 20.67 | 0.235 | 114.52 | 0.817 | 172.01 | 0.532 | 16.12 | 0.021 |
| 20% PG | 26.00 | | 97.64 | | 204.70 | | 71.59 | |
| 30% Gly | 26.00 | 0.307 | 114.68 | 0.598 | 213.19 | 0.756 | 57.51 | 0.575 |
| 30% PG | 22.00 | | 72.45 | | 203.80 | | 82.32 | |
| 40% Gly | 28.00 | 0.742 | 163.02 | 0.501 | 238.16 | 0.488 | 85.16 | 0.988 |
| 40% PG | 26.67 | | 105.40 | | 308.24 | | 86.20 | |
| 50% Gly | 32.67 | 0.571 | 258.80 | 0.028 | 219.94 | 0.707 | 140.98 | 0.992 |
| 50% PG | 29.33 | | 80.96 | | 237.98 | | 142.28 | |

TABLE 22

Extraction Efficiency of AM before and after Lyophilization (Gly)

| | Content | Average Weight (mg) | P-value Weight | Average Protein (ug/ml) | P-value Protein | Average HA (ng/ml) | P-value HA | Average HC-HA/PTX3 (ng/ml) | P-value HC-HA/PTX3 |
|---|---|---|---|---|---|---|---|---|---|
| AM | 10% Gly | 25.33 | 0.005 | 132.34 | 0.169 | 109.16 | 0.070 | 37.55 | 0.637 |
| AM Lyo | 10% Gly | 15.00 | | 1.44 | | 286.61 | | 67.32 | |
| AM | 20% Gly | 20.67 | 0.036 | 114.52 | 0.374 | 172.01 | 0.241 | 16.12 | 0.083 |
| AM Lyo | 20% Gly | 16.00 | | 64.76 | | 254.07 | | 118.37 | |
| AM | 30% Gly | 26.00 | 0.138 | 114.68 | 0.405 | 213.19 | 0.212 | 57.51 | 0.906 |
| AM Lyo | 30% Gly | 19.33 | | 47.39 | | 294.83 | | 60.83 | |
| AM | 40% Gly | 28.00 | 0.166 | 163.02 | 0.206 | 238.16 | 0.773 | 85.16 | 0.292 |
| AM Lyo | 40% Gly | 21.67 | | 54.08 | | 263.09 | | 25.05 | |
| AM | 50% Gly | 32.67 | 0.179 | 258.80 | 0.034 | 219.94 | 0.921 | 140.98 | 0.435 |
| AM Lyo | 50% Gly | 23.00 | | 93.44 | | 228.05 | | 36.58 | |

TABLE 23

Extraction Efficiency of AM before and after Lyophilization (PG)

| | Content | Average Weight (mg) | P-value Weight | Average Protein (ug/ml) | P-value Protein | Average HA (ng/ml) | P-value HA | Average HC-HA/PTX3 (ng/ml) | P-value HC-HA/PTX3 |
|---|---|---|---|---|---|---|---|---|---|
| AM | 10% PG | 25.33 | 0.056 | 97.70 | 0.360 | 291.58 | 0.393 | 45.75 | 0.197 |
| AM Lyo | 10% PG | 12.67 | | 46.14 | | 230.57 | | 12.06 | |
| AM | 20% PG | 26.00 | 0.040 | 97.64 | 0.558 | 204.70 | 0.687 | 71.59 | 0.015 |
| AM Lyo | 20% PG | 12.67 | | 54.88 | | 224.82 | | 9.64 | |
| AM | 30% PG | 22.00 | 0.014 | 72.45 | 0.952 | 203.80 | 0.857 | 82.32 | 0.171 |
| AM Lyo | 30% PG | 12.00 | | 70.26 | | 197.33 | | 4.51 | |
| AM | 40% PG | 26.67 | 0.019 | 105.40 | 0.796 | 308.24 | 0.308 | 86.20 | 0.241 |
| AM Lyo | 40% PG | 13.00 | | 139.00 | | 237.44 | | 6.77 | |
| AM | 50% PG | 29.33 | 0.005 | 80.96 | 0.927 | 237.98 | 0.675 | 142.28 | 0.364 |
| AM Lyo | 50% PG | 13.33 | | 89.72 | | 264.59 | | 76.28 | |

TABLE 24

γ-Irradiated Lyophilized vs. γ-Irradiated Non-lyophilized AM

| Content | Average Weight (g) | p-value (weight) | Average Protein Conc (ug/ml) | p-value [Prot] | Average HA Conc (ng/ml) | p-value [HA] | Average HC-HA/PTX3 Conc (ng/ml) | p-value [HC-HA/PTX3] |
|---|---|---|---|---|---|---|---|---|
| 50% Gly | 0.025 ± 0.004 | 0.089 | 313.024 ± 68.2 | 0.003 | 207.128 ± 40.2 | 0.021 | 126.821 ± 36.4 | 0.713 |
| 50% Gly (Lyophilized) | 0.016 ± 0.006 | | 82.989 ± 35.4 | | 357.347 ± 55.0 | | 157.459 ± 123 | |
| 3.3% Gly | 0.020 ± 0.006 | 0.199 | 148.904 ± 127 | 0.467 | 275.659 ± 83.3 | 0.274 | 216.386 ± 30.4 | 0.080 |
| 3.3% Gly (Lyophilized) | 0.013 ± 0.003 | | 79.916 ± 67.2 | | 204.126 ± 15.9 | | 84.996 ± 75.7 | |
| 3.3% PG | 0.025 ± 0.003 | 0.006 | 226.427 ± 58.4 | 0.067 | 232.114 ± 58.9 | 0.300 | 302.321 ± 334 | 0.342 |
| 3.3% PG (Lyo) | 0.011 ± 0.001 | | 89.461 ± 72.8 | | 170.044 ± 68.2 | | 64.230 ± 60.3 | |
| Non-irradiated (50% Gly) | 0.027 ± 0.007 | 0.077 | 353.560 ± 185 | 0.714 | 179.160 ± 110.6 | 0.754 | 336.43 ± 285 | 0.514 |
| Non-irradiated (50% Gly) (Lyophilized) | 0.015 ± 0.003 | | 260.986 ± 354 | | 202.274 ± 19.6 | | 187.550 ± 217.2 | |

TABLE 25

Summary Matrix

| | Lyophilization (−) | | Lyophilization (+) | |
|---|---|---|---|---|
| | Glycerol | Propylene Glycol | Glycerol | Propylene Glycol |
| γ-irradiation (−) | 1) ↑ [Gly] ↑ weight (all p > 0.05) 2) ↑ [Gly] ↑ [Protein] (50% Gly p = 0.014) 3) ↑ [Gly] ↑ [HA] from 10-40% Gly (all p > 0.05) 4) ↑ [Gly] ↑ [HC-HA/PTX3] (all p > 0.05) 1) Extractability of protein, HA or HC-HA/PTX3 is not affected by adding different concentrations of Gly or PG 2) There is a trend of increasing extractability of protein/weight by ↑ conc of Gly than PG, while there is no trend in the extractability of [HA] and [HC-HA/PTX3] when preserved in Gly or PG. Gly binds H₂O more effectively, and such binding facilitates protein extractability from AM matrix. HA and HC-HA/PTX3 are readily extractable due to its water-soluble property. | 1) ↑ [PG] ↑ weight (50% PG, p = 0.008) 2) ↑ [PG] no [Protein] difference (all p > 0.05) 3) ↑ [PG] no [HA] difference (all p > 0.05) 4) ↑ [PG] ↑ [HC-HA/PTX3] (all p > 0.05) | 1) ↑ [Gly] ↑ weight (p < 0.05 30-50% Gly) 2) ↑ [Gly] ↑ [Protein] (all p > 0.05) 3) ↑ [Gly] no [HA] difference (all p > 0.05) 3) ↑ [Gly] no [HC-HA/PTX3] trend (all p > 0.05) Extractability of weight, protein, and HC-HA/PTX3 is further reduced by lyophilization, especially in PG (weight/HC-HA/PTX3) or Gly (protein at high conc), while extractability of [HA] is not affected in Gly or PG Lyophilization does not completely remove H₂O especially in high conc of Gly, which will affect protein extractability but not HC-HA/PTX3 later at low conc of Gly | 1) ↑ [Gly] no weight difference (p < 0.05 30 & 50% PG) 2) ↑ [PG] ↑ [Protein] until 40% PG (all p > 0.05) 3) ↑ [PG] no [HA] difference (all p > 0.05) 4) ↑ [PG] no [HC-HA/PTX3] trend (all p > 0.05) |

TABLE 25-continued

Summary Matrix

| | Lyophilization (−) | | Lyophilization (+) | |
|---|---|---|---|---|
| | Glycerol | Propylene Glycol | Glycerol | Propylene Glycol |
| γ-irradiation (+) Control - Preserved in 50% Gly but not γ-irradiated | 1) No significant difference in weight for 3.3% Gly, 50% Gly, & Control (all p > 0.05) 2) No significant difference between [Protein] for 3.3% Gly, 50% Gly, & Control (all p > 0.05) 3) No significant difference between [HA] for 3.3% Gly, 50% Gly, & Control (all p > 0.05) 4) No significant difference between [HC-HA/PTX3] for 3.3% Gly, 50% Gly, & Control (all p > 0.05) Extractability of protein, HA or HC-HA/PTX3 is not affected by γ-irradiation because no statistical difference is noted in Gly (3.3% & 50%) or PG (3.3%) group | 1) No significant difference in weight for 3.3% PG, & Control (p = 0.68) 2) No significant difference between [Protein] for 3.3% PG & Control (p = 0.18) 3) No significant difference between [HA] for 3.3% PG & Control (p = 0.26) 4) No significant difference between [HC-HA/PTX3] for 3.3% PG & Control (p = 0.45) | 1) No significant difference in weight for 3.3% Gly, 50% Gly, & lyophilized Control (all p > 0.05) 2) No significant difference between [Protein] for 3.3% Gly, 50% Gly, & lyophilized Control (all p > 0.05) 3) No significant difference between [HA] for 3.3% Gly, 50% Gly, & lyophilized Control (all p > 0.05) 3) No significant difference between [HC-HA/PTX3] for 3.3% Gly, 50% Gly, & lyophilized Control (all p > 0.05) γ-irradiation does not cause additional damage to lyophilized AM preserved in 3.3% Gly, 3.3% PG, 50% Gly when compared to the non-irradiated lyophilized control. 3.3% PG showed significant difference in weight when lyophilized (p = 0.006, #3 & #19, highlighted in grey). This verifies our initial finding that PG does not bound as tightly to $H_2O$ compared to Gly. The only statistically significant data comes by comparing 50% Gly lyophilized vs. non-lyophilized as the [Protein] and [HA] has a p-value of 0.003 and 0.021 respectively. The actual data shows the [Protein] for the non-lyophilized sample is significantly higher (313 ug/ml) compared to the lyophilized sample with 83 ug/ml, reaffirming our initial finding that lyophilization dampens the extraction efficiency of protein from AM. However, the actual [HA] shows that the lyophilized sample has a higher HA concentration (357 ng/ml) compared to the non-lyophilized sample (207 ng/ml) reaffirming our initial finding that HA is easily extractable even when lyophilized due to its water-soluble property. | 1) No significant difference in weight for 3.3% PG, & Control (p = 0.15) 2) No significant difference between [Protein] for 3.3% PG & lyophilized Control (p = 0.25) 3) No significant difference between [HA] for 3.3% PG & lyophilized Control (p = 0.25) 4) No significant difference between [HC-HA/PTX3] for 3.3% PG & lyophilized Control (p = 0.22) |

TABLE 26

Study Results for Radioprotectants for AM Preservation

| | Lyophilization (−) | Lyophilization (+) |
|---|---|---|
| γ-irradiation (−) | 50% Glycerol | 50% Glycerol |
| γ-irradiation (+) | Glycerol or Propylene Glycol | 50% Glycerol |

Example 4

In Examples 2 and 3, it was measured quantitatively that γ-irradiation did not cause a statistically significant change to AM cryopreserved in Glycerol and PG in terms of protein, HA, and HC-HA/PTX3 concentrations. In this example, the structural integrity of the HC-HA/PTX3 complex was examined. a western blot analysis of the remaining AM extract with HAase digestion, which digests HA but not glycosaminoglycans such as chondroitin and chondroitin sulfate, was performed. This analysis allowed for a relative comparison of the active ingredients between the γ-irradiated samples and the non γ-irradiated samples by comparing the intensity and sharpness of the bands with or without HAase treatment. Table 27 lists the AM extract samples (from Examples 2 and 3) that were used in the experiment.

TABLE 27

AM Extract Samples for Western Blotting

| γ-irradiated | Non γ-irradiated |
|---|---|
| Cryopreserved AM | |
| A. 50% Glycerol | F. 0% Glycerol/PG |
| B. 3.3% Glycerol | G. 10% Glycerol |

TABLE 27-continued

AM Extract Samples for Western Blotting

| γ-irradiated | Non γ-irradiated |
| --- | --- |
| | Cryopreserved AM |
| C. 3.3% Propylene Glycol | H. 50% Glycerol (Donor #2) |
| D. 10% Trehalose | I. 10% Propylene Glycol |
| E. 50% Glycerol | J. 50% Propylene Glycol |
| (Non-irradiated, Donor #1) | |

AM extracts for each condition were individually prepared (n=3). The protein, HA, and HC-HA/PTX3 concentrations were previously determined for each individual extract (see Examples 2 and 3 and Table 28). A total of 40 µg of protein (20 µg with or without HAase digestion each) was required for each condition to perform Western Blot. Due to the limited amount of AM extract available, the smallest Western Blot Apparatus (12 well, 20 µl per well, 20 µg protein per well) was used.

TABLE 28

Protein Data for Samples Analyzed

| | Content | Total Volume (ml) | Protein Conc. (ug/ml) | Total Protein (ug) | HA Conc. (ng/ml) | Total HA (ng) |
| --- | --- | --- | --- | --- | --- | --- |
| Gamma Irradiated | A. 50% Gly | 0.2644 | 224.92 | 59.47 | 235.32 | 62.219 |
| | B. 3.3% Gly | 0.2088 | 102.43 | 21.39 | 306.36 | 63.968 |
| | C. 3.3% PG | 0.2178 | 161.24 | 35.12 | 263.77 | 57.449 |
| | D. 10% Trehalose | 0.1908 | 197.21 | 37.63 | 253.54 | 48.375 |
| | E. 50% Gly (CTL) | 0.2068 | 180.69 | 37.37 | 182.41 | 37.722 |
| Non Irradiated | F. 0% Gly/PG | 0.2868 | 105.35 | 30.21 | 312.44 | 89.609 |
| | G. 10% Gly | 0.2398 | 149.58 | 35.87 | 119.41 | 28.634 |
| | H. 50% Gly | 0.2368 | 121.39 | 28.74 | 243.65 | 57.696 |
| | I. 10% PG | 0.2348 | 117.50 | 27.59 | 319.04 | 74.910 |
| | J. 50% PG | 0.2518 | 110.69 | 27.87 | 264.21 | 66.528 |
| | HC-HA/PTX3 | 0.2976 | 54.31 | 16.16249 | 20000.00 | 67204.3 |

The AM extracts were extracted using 1×PBS buffer containing phosphates and salt. To normalize the loading of these extracts onto the gel with or without HAase digestion, the AM extracts were concentrated first through lyophilization. The concentrated extract containing concentrated salt and phosphate was then dialyzed to remove excess salt and phosphate from the extract. Briefly, AM extracts were topped up to the minimum 500 µl volume with dH₂O and injected into a Slide A Lyser 2K Dialysis Cassettes (Thermo Scientific, #66203). The cassettes were then dialyzed in 2 L filtered water at 4° C. for 4 hours with a change of filtered water at the midpoint (2 hour mark). The dialyzed samples were then lyophilized for 4 hours and resuspended in distilled water.

For hyaluronidase treatment, the AM extracts were treated with 20 units/ml hyaluronidase (HAase #100740, Seikagaku Biobusiness Corporation) at 60° C. for 2 h (0.02M sodium acetate-acetic acid buffer, 0.015M NaCl, pH 6.0) to specifically digest HA and not other glycoaminglycans such as chondroitin and chondroitin sulfate. HAase digestion was preferred over NaOH treatment which not only destroys ester bonds but also causes protein hydrolysis.

The samples were then run on SDS-PAGE and analyzed by Western blotting using an antibody against IαI. The amount of protein and relative amount of HA loaded in each well is listed in Table 29.

TABLE 29

Amount of Protein & HA loaded into each well

| | Content | Protein/well (ug) | HA/well (ng) |
| --- | --- | --- | --- |
| Gamma Irradiated | A. 50% Gly | 15 | 16 |
| | B. 3.3% Gly | 11 | 32 |
| | C. 3.3% PG | 15 | 24 |
| | D. 10% Trehalose | 15 | 20 |
| | E. 50% Gly (CTL) | 15 | 15 |
| Non Irradiated | F. 0% Gly/PG | 15 | 45 |
| | G. 10% Gly | 15 | 12 |
| | H. 50% Gly | 14 | 28 |
| | I. 10% PG | 13.5 | 37 |
| | J. 50% PG | 14 | 33 |

The HCs of IαI are covalently linked with HA as ester bonds formed between two HCs and the chondroitin sulfate chain of bikunin in the intact IαI molecule link HCs to HA. When run on a polyacrylamide gel, purified IαI from a cell yields a major band at ~250 kDa, a HMW band at the bottom of the loading well as well as two other bands at 75 and 120 kDa. The HMW band, where size precludes the complex from entering the gel are IαI typically components covalently linked with HMW HA which can be digested by HAase to run in the gel. The 75 kDa band corresponds to free HC while the 120 kDa band is likely HC covalently coupled with either bikunin or TSG-6. HAase digestion increases the intensity and sharpness of the 250, 120 and 75 kDa bands indicating that some of these species may be released from HA.

In this experiment, Western blotting confirmed the presence of HC-HA/PTX3 in AM extracts derived from γ-irradiated and non-irradiated AM which corresponded to the initial conclusion that γ-irradiation does not significantly alter the amount of protein, HA, and HC-HA/PTX3 extracted from the samples indicating that γ-irradiation does not significantly damage the active ingredients in AM. HAase digestion increased the intensity and sharpness of the 75 kDa band. Although the Western Blot data showed the presence of HC-HA/PTX3 from γ-irradiated samples, the intensity and sharpness of these bands are less compared to the non-irradiated samples. By comparing data from Western blot and the concentrations data from Examples 2 and 3, a general trend was observed where the higher amount of HA/well correlated with an increase in band intensity and sharpness.

Example 5

In this Example, yellowing effect from each component of the cryomedia (DMEM, Glycerol, PBS, and Antibiotics) was examined before and after γ-irradiation. Current commercial AM products uses DMEM (4.5 g/L D-Glucose, with 25 mM HEPES, with Sodium Pyruvate, without L-Glutamine & without Phenol Red by Cellgro) as the base media. However, DMEM has to be stored at 2-8° C. and has a shelf life of 1 year. Because the new fetal support tissue products will potentially be kept at room temperature (20-25° C.) after γ-irradiation, DMEM will be substituted with PBS 1× to complement this change. PBS has a storage condition of 15-30° C. and a shelf life of 3 years. The current cryomedia mixture also consists of antibiotics 0.2% Ciproflaxin and 0.5% Amphotericin B, and the MSDS by the manufacturer cautions against gamma irradiating the antibiotics. DMEM and the antibiotics turn the media yellow after γ-irradiation. Table 30 summarizes the observations of different fetal support tissue product prepared different base media before and after irradiation.

TABLE 30

Summary of Observations of Base Media Coloration Before and After γ-Irradiation

| | PBS 1x | PBS + Antibiotics | 1:1 PBS/Gly | 1:1 PBS/Gly + Antibiotics | DMEM | DMEM + Antibiotics | 1:1 DMEM/Gly | 1:1 DMEM/Gly + Antibiotics |
|---|---|---|---|---|---|---|---|---|
| Non γ | Clear | Clear | Clear | Clear | Clear | Clear | Clear | Clear |
| γ-irradiated | Clear | Yellow tint | Clear | Yellow tint | Yellow | Yellow | Yellow | Yellow |
| Comments | PBS does not turn yellow | Antibiotics turn yellow | Glycerol does not turn yellow | Glycerol + antibiotics turn yellow | DMEM turns yellow | DMEM + Antibiotics turn yellow | DMEM turns yellow | DMEM + Antibiotics turn yellow |

1×PBS 1× did not turn yellow after γ-irradiation but turned yellow when combined with antibiotics (0.2% Ciproflaxin and 0.5% Amphotericin B) indicating that only the antibiotics turns yellow after γ-irradiation. The combination of 1:1 PBS/Glycerol did not turn yellow after γ-irradiation but the combination of 1:1 PBS/Glycerol+antibiotics turned yellow reaffirming that antibiotics turn yellow after γ-irradiation. The DMEM media by itself turned yellow after γ-irradiation and DMEM plus antibiotics also turned yellow. The combination of 1:1 DMEM/Glycerol also turned yellow, which is caused by the DMEM and not Glycerol as 1:1 PBS/Glycerol did not turn yellow.

Example 6

In this example, histological evaluation was used to determine the structural integrity of the cryopreserved fetal support tissue product before and after γ-irradiation. Specifically the effects of radiation on the epithelium, basement membrane and stroma were assessed. Cryopreserved human amniotic membrane product comprises cells that have been killed via freezing thus ensuring that the tissue does not mount an immune response in the host. Histology that is typically performed on fresh tissue usually assesses live, healthy cells. In contrast, histology of the amniotic membrane product is used to establish the presence of the epithelium, the basement membrane and the stroma structures, whether continuous or discontinuous. Additionally, when looking at the cells contained as part of cryopreserved amniotic membrane tissue, the presence of ghost cells, pyknotic cells or degenerated cells is to be viewed as a desirable attribute showing that the cells are no longer alive.

The cryopreserved product was kept on dry ice for duration of the irradiation procedure. The samples were irradiated in a C-cell irradiatior at Dosimeters were employed to calculate the delivered radiation dose. An average dosage of 30 kGy was delivered to the samples.

Periodic Acid-Schiff Reaction (PAS) stain was used to demonstrate the presence of the basement membrane of amniotic membrane tissue. Alcian Blue Stain was used to demonstrate the presence of the stromal layer of the amniotic membrane tissue. Hematoxylin and Eosin (H & E) stain was used to demonstrate the presence of the epithelial layer of the amniotic membrane tissue. Morphological acceptance criteria was established as 'pass' or 'fail' based on the criteria set forth in Table 31.

TABLE 31

Tissue Grading Criteria

| Histological Evaluation | ACCEPTANCE CRITERIA | |
|---|---|---|
| | Pass | Fail |
| Epithelium (H&E stain for nucleus, chromatin, organelles, cell wall) | Epithelium present: Epithelium continuous or discontinuous with overall average ≥ 50% present Cells present (pyknotic, degenerated, ghost cells acceptable) | Epithelium absent or with overall average less than 49% present |
| Basement Membrane (BM) (PAS) | Basement Membrane present: BM continuous or discontinuous with overall average ≥ 50% present | BM absent or with overall average less than 49% |
| Stroma (Alcian Blue) | Stroma present: Stroma continuous or discontinuous with overall average ≥ 50% present Cells present (pyknotic, degenerated, ghost cells acceptable) | Stroma absent or with overall average less than 49% present |

"Pass" indicated the presence of the epithelium, stroma and basement membrane and possibly pyknotic, degenerated or ghost cells and is a sign of tissue integrity. "Fail" indicated that the tissue has suffered a loss in integrity, signaling deterioration over time with significant loss of the epithelium, stroma and basement membrane. γ-irradiated AM test samples were compared to the morphology of non γ-irradiated AM (frozen at −80° C. for 1 week) as a control; any statistically significant differences between the control and the test samples were flagged during analysis. If such changes are noted in three different samples, the condition was deemed unacceptable unless repeated with enough sample size to arrive at a statistical difference.

This evaluation was considered valid for histological integrity after undergoing γ-irradiation if no statistical significance between the control (non γ-irradiated AM) and the test condition (γ-irradiated AM) was found using three or more samples. The Student's t-test was used to determine if there were significant structural differences between the non γ-irradiated (Control) and γ-irradiated amniotic membrane (AM) with regard to histological quality attributes. Three assumptions were made when analyzing the data: 1) the data was obtained from 2 independent samples; 2) the samples were assumed to be normally distributed; and 3) the significance level is set at 1% ($\alpha=0.01$).

Nine samples (n=3) from 3 different lots (3 samples/lot) for each condition (γ-irradiated and non γ-irradiated AM) were assessed. All samples evaluated before (Control) and after γ-irradiation met the acceptance criteria of "pass" as all sample readout shows continuous or discontinuous histology with overall average >50% present. None of the sample evaluated met the "fail" criteria. Histological quality data supported that γ-irradiation does not damage cryopreserved amniotic membrane as there is no statistically significant difference between γ-irradiated and non γ-irradiated amniotic membrane with regard to histological quality attributes of epithelium, basement membrane, and stromal layers.

Example 7

In this example, the cryo and radioprotectant efficiency during γ-irradiation of cryo and radioprotectants at varying concentrations was analyzed based on biochemical (e.g. protein concentration) and functional analysis (e.g. osteocloast assay).

Because of the limitations experienced in sample preparation due to incomplete homogenization (see Example 2), an optimized method of sample preparation was used in this experiment. The AM tissue was first frozen in liquid nitrogen and pulverized into a powder form with a BioPulverizer. The powder was then diluted in 1×PBS 1:3 w/v and homogenized with a Wheaton Douncer. The proteins were then subsequently extracted in 4M Guanidine/HCl and dialyzed against PBS for biochemical analysis and functional assays.

The cryo/radioprotectants analyzed in Example 2 were re-assessed (with the exception of Mannitol as the data collected did not show a protection effect) along with varying concentrations of Propylene Glycol and Glycerol that were previously identified as the best protective agents using the new sample preparation protocol. The concentrations of Gly and PG were varied to obtain a dose curve to identify optimal concentrations. Preparation of the samples was performed as described in Example 2. The concentration for the panel of cryo/radioprotectants was set at 10% for Glycerol, PG, Trehalose and DMSO while the optimization study varied the concentration of both Glycerol and PG at 0%, 10%, 30%, 50% and 70%. The control was set to be cryopreserved AM in 1:1 DMEM/Glycerol without γ-irradiation. The samples were analyzed based on total protein, total HA, and biological/functional assay. Protein concentrations were measured by BCA Protein Assay kit (Pierce, Rockford, Ill.) using the extracted supernatant. HA concentration is quantified using the HA Test Kit (Corgenix #029-001, Broomfield, Colo.).

Tissue Color Change after γ-Irradiation at Ambient Temperature

1×PBS has a storage condition of 15-30° C. and a shelf life of 3 years and is a suitable base media for storage at room temperature. Current commercial AM products uses DMEM (4.5 g/L D-Glucose, with 25 mM HEPES, with Sodium Pyruvate, without L-Glutamine & without Phenol Red by Cellgro) as the base media. However, DMEM has to be stored at 2-8° C. and has a shelf life of 1 year. Because the new fetal support tissue products will be kept at room temperature (20-25° C.) after γ-irradiation, DMEM was substituted with 1×PBS to complement this change. DMEM and antibiotics also turn the media yellow after γ-irradiation, whereas 1×PBS does not (Example 5).

Previously, all AM tissue was γ-irradiated frozen (i.e. with dry ice) which revealed that the media and tissue turned yellow (Example 5) due to the presence of DMEM and antibiotics (Ciproflaxin and Amphotericin B). In this example, γ-irradiation was performed at Room temperature and it was noted that only the AM tissue changed color after γ-irradiation. AM tissue γ-irradiated in Trehalose and Glycerol turned yellow while AM tissue γ-irradiated in Propylene Glycol turned pink/red. Only the control AM and γ-irradiated AM in PBS remained clear. The color changes are likely due to the hydroxyl group (—OH) present in trehalose (11 hydroxyl groups), glycerol (3 hydroxyl groups) and propylene glycol (2 hydroxyl group). Studies have revealed that sensitivity of drugs is significantly degraded by γ-irradiation in aqueous solution due to highly reactive radiolytic species of water comprising of hydroxyl radicals (OH), hydrogen atoms (H) and electrons (e). In an earlier study, the authors revealed that the sensitivity of drug to radiation depends on the position of the hydroxyl group in the aliphatic chain and also increased as the number of hydroxyl groups in the aliphatic alcohol increased. The order of organic solvent with regard to the sensitivity of drugs to radiation is: 1,3 pronanediol>glycerol>propylene glycol>n-propanol. The sensitivity of drug to radiation can be counteracted with free radical scavengers found in different types of surfactants such as sodium lauryl sulfate, Tween-80 and benzalkonium chloride. The brown coloration change is also observed in HA (present abundantly in AM) is exposed to microwave irradiation resulting in an increased in antioxidant activities.

Biochemical Analysis

The total protein extracted per weight was lower in all γ-irradiated samples compared to the non γ-irradiated control (FIG. 1). This suggests that γ-irradiation at ambient temperature affects the protein present in the tissue. One mechanism to explain this result is the increased cross linking effect of γ-irradiation at ambient temperature causing the tissue to be fixed hence the lower amount of protein extracted. In spite of this, general trends were observed for the different radio/cryoprotectants. Firstly, there is a linear increase in the protein extracted as the concentration of Gly increases. For PG, the protein extraction peaks at 30% PG and decreases as the concentration increased to 50% and 70%. The efficiency of protein extracted from γ-irradiated AM tissue was ranked as follows: 30% PG>PBS>70% Gly=10% PG=10% Trehalose.

Figure 2:
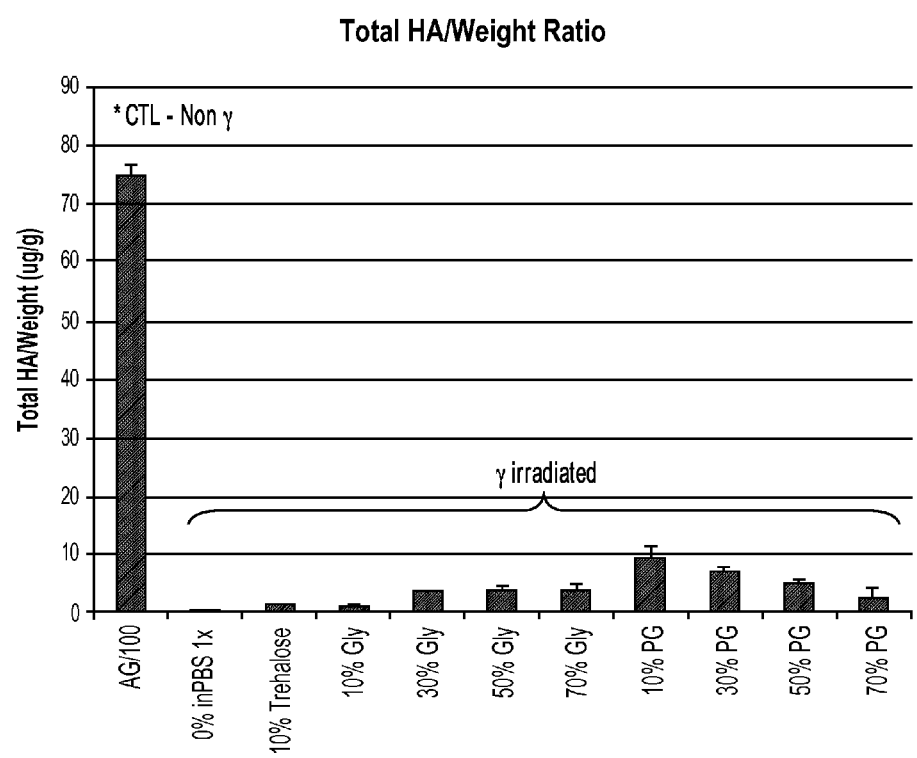
FIG. 2 exemplifies total HA extracted per weight in γ-irradiated AM samples (irradiated at RT) compared to the non γ-irradiated control.

The total HA extracted per weight was also lower in all γ-irradiated samples compared to the non γ-irradiated control (FIG. 2). This suggests that γ-irradiation at ambient temperature affects the HA present in the tissue. One mechanism to explain this result is the highly reactive radiolytic species of water comprising of hydroxyl radicals (OH), hydrogen atoms (H) and electrons (e) that damages the HA present in the tissue. In spite of this, general trends were observed for the different radio/cryoprotectants. Notably there was a linear trend in the HA present as the concentration of Gly increases. For PG, an inverse trend was observed as the HA present in AM tissue decreases as the concentration of PG increases. The amount of HA present in γ-irradiated AM tissue is in the order: 10% PG>30% PG>50% PG>50% Gly.

Figure 3:
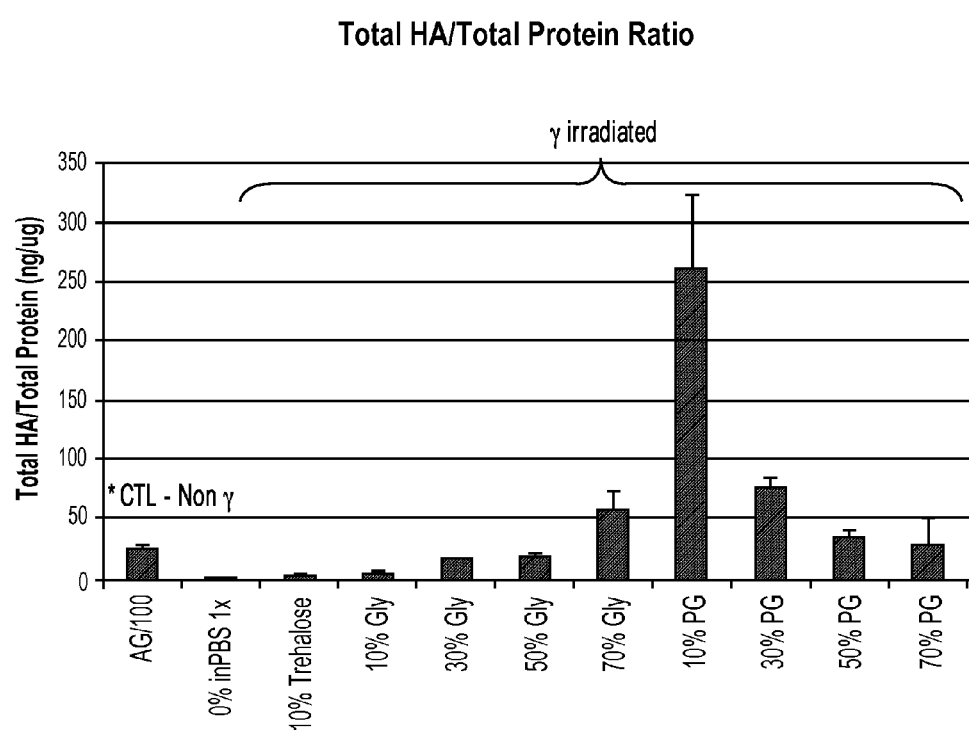
FIG. 3 exemplifies total HA extracted per total protein extracted in γ-irradiated AM samples (irradiated at RT) compared to the non γ-irradiated control.

The same trend in FIG. 2 was observed by analyzing the ratio of HA:Protein (FIG. 3). There was an increasing linear trend in HA:Protein ratio as the concentration of Gly increases. Again, the inverse trend was observed for HA:Protein ratio as the concentration of PG increases. In contrast to the total HA concentration, the HA:Protein ratio of the CTL sample without γ-irradiation was lower than the ratio of HA:Protein 10% PG, 70% Gly, 30% PG and 50% PG.

These results reaffirmed that high concentration of Gly (70%) and low concentration of PG (10%) had the most protective effect for AM tissue against γ-irradiation.

Western Blot samples were electrophoresed on 4-15% (w/v) gradient acrylamide ready gels under denaturing and reducing conditions. Proteins were transferred to the nitrocellulose membrane. The membrane was then blocked with 5% (w/v) fat-free milk in TBST (50 mM Tris-HCl, pH 7.5, 150 mM NaCl, 0.05% (v/v) Tween 20) followed by sequential incubation with specific primary antibodies against IαI, and its secondary antibody. Immunoreactive proteins were detected with Western Lighting™ Chemiluminesence Reagent.

HA sizes in AM extracts were analyzed by an agarose gel. Briefly, tissue extracts with or without treatment by HAase were separated on 0.5% (w/v) agarose gels followed by staining with 0.005% (w/v) Stains-all dye in 50% (v/v) ethanol. The gels were stained overnight at 25° C. with light protection and HA visualized as bluish bands after destaining in water and exposure to the room light for 6 h. The HA sizes were estimated by comparing to the Select-HA HiLadder and HMW HA (Healon).

The biochemical data from Example 2 (frozen γ-irradiation) was compared to the room temperature γ-irradiation to determine the protective effect of freezing during γ-irradiation. For the protein concentration per weight of AM extract, the extraction efficiency of protein was significantly reduced when AM products are γ-irradiated at room temperature. For the total protein per weight of the AM extract, the amount of protein extracted per weight was significantly reduced when AM products were γ-irradiated at room temperature. The only exception is the Non γ-irradiated control which can be explained as a high salt solution (4M GnHCl) which was used to extract the room temperature AM products compared to the use of PBS for frozen AM products. For the concentration of HA extracted per weight, the extraction efficiency of HA was significantly reduced when AM products are γ-irradiated at room temperature. For the amount of HA per weight of AM extract, the amount of HA extracted per weight is significantly reduced when AM products are γ-irradiated at room temperature. The only exception is the Non γ-irradiated control which can be explained as a high salt solution (4M GnHCl) was used to extract the Room Temperature AM products compared to the use of PBS for Frozen AM products.

This data indicated that room temperature γ-irradiation damages more constituents present in AM products compared to frozen γ-irradiation. γ-irradiation presents challenges of degradation that is associated with generation of free radicals, HA chain fragmentation from HMW to LMW particularly when HA is in its hydrated state. Degradation of HMW HA to LMW HA is usually performed in an aqueous solution and lyophilization better preserves the fundamental structure of HA. In short, AM tissue needs to be γ-irradiated frozen to prevent hydrolysis of water that releases of hydroxyl radicals (OH), hydrogen atoms (H) and electrons (e) that damages the active biochemical components of AM tissue.

Functional Analysis—Osteoclast Assay

Murine RAW 264.7 macrophage cells treated with 50 ng/ml of RANKL were dosed with 1 volume fraction of AM samples to determine its potency of inhibiting osteoclast formation. 1 volume fraction is defined as one eighth of the volume of the AM tissue extract that has been normalized to its original tissue weight.

The RAW 264.7 macrophage cells were cultured at a density of $4.0 \times 10^4$ cells/ml at a volume of 0.15 ml for a 96-well plate in α-MEM supplemented media with 10% FBS, 100 μg/ml penicillin & streptomycin. Following addition of the AM sample, the cells were incubated with or without RANKL stimulation. The 50 ng/ml RANKL stimulation was added in a time dependent manner according to the conditions listed below: Each condition was performed in sextuplet (n=6).

TABLE 32

Experimental Samples for Osteoclast Assay

| Experimental Sample | Sample Addition | RANKL Addition |
|---|---|---|
| 1. −ve CTL (PBS 1X) | 24 h | n/a |
| 2. +ve CTL (PBS 1X) | 24 h | 24 h |
| 3. HC-HA/PTX3 (5 ug/ml HA) | 24 h | 24 h |
| 4. AMP (200 ug/ml Protein) | 24 h | 24 h |
| 5. #1 - AG/100 (CTL, non γ-irradiated) | 24 h | 24 h |
| 6. #2 - PBS (γ-irradiated) | 24 h | 24 h |
| 7. #3 10% Trehalose (γ-irradiated) | 24 h | 24 h |
| 8. #5 - 10% Glycerol (γ-irradiated) | 24 h | 24 h |
| 9. #6 - 30% Glycerol (γ-irradiated) | 24 h | 24 h |
| 10. #7 - 50% Glycerol (γ-irradiated) | 24 h | 24 h |
| 11. #8 - 70% Glycerol (γ-irradiated) | 24 h | 24 h |
| 12. #9 - 10% Propylene Glycol (γ-irradiated) | 24 h | 24 h |
| 13. #10 - 30% Propylene Glycol (γ-irradiated) | 24 h | 24 h |
| 14. #11 - 50% Propylene Glycol (γ-irradiated) | 24 h | 24 h |
| 15. #12 - 70% Propylene Glycol (γ-irradiated) | 24 h | 24 h |

Macrophage cells were visualized under a phase-contrast microscope for 5 consecutive days. The culture was terminated on Day 5, and the wells from each well were washed with 150 μl of 1×DPBS before being lysed in preparation for TRAP Colorimetric Staining Tartrate-resistant acid phosphatase (TRAP) is expressed in osteoclast cells. Cells were lysed with 50 μl (per 96 well plate) of 1×PBS and 1% Triton by pipetting and then transferred to a 1.5 ml microfuge tube (kept at −80° C. at this stage). Upon thawing, the sample was centrifuged at 10000 rpm for 10 minutes. For TRAP Colorimetric analysis, 15 μl supernatant was transferred into 96 well (n=2) plate before addition of 100 μl TRAP (Acid Phosphatase Leukocyte Kit, Sigma). A sample consisting of the lysis buffer (1% Triton in PBS) was used as a background control. The TRAP media was added in a steady state manner and each sample was tested in duplicate. The samples were incubated for 30-60 minutes (with visual inspection every 15 minutes) at 37° C. The plate was read at 570 nm to obtain the TRAP absorbance reading.

Figure 4:
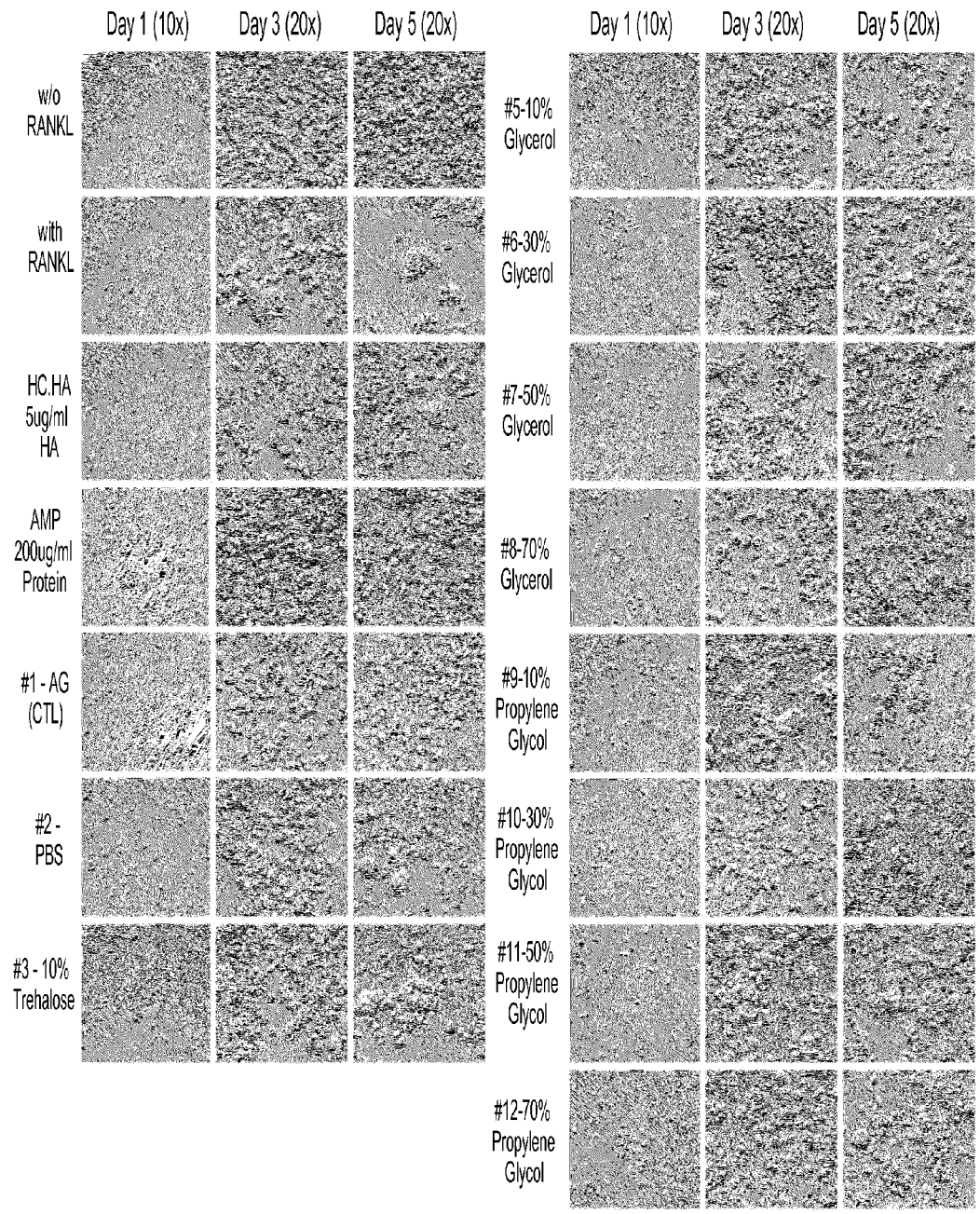
FIG. 4 exemplifies murine RAW 264.7 macrophage cell morphology with or without RANKL stimulation in the presence of AM samples.

Macrophage cells without RANKL induction revealed no osteoclast (large multinucleated cells) formation at Day 5 while cells treated with RANKL showed osteoclast formation starting from Day 3 (FIG. 4). Cells treated with HC-HA/PTX3, AMP and all experimental AM extracts did not reveal significant osteoclast formation.

Figure 5:
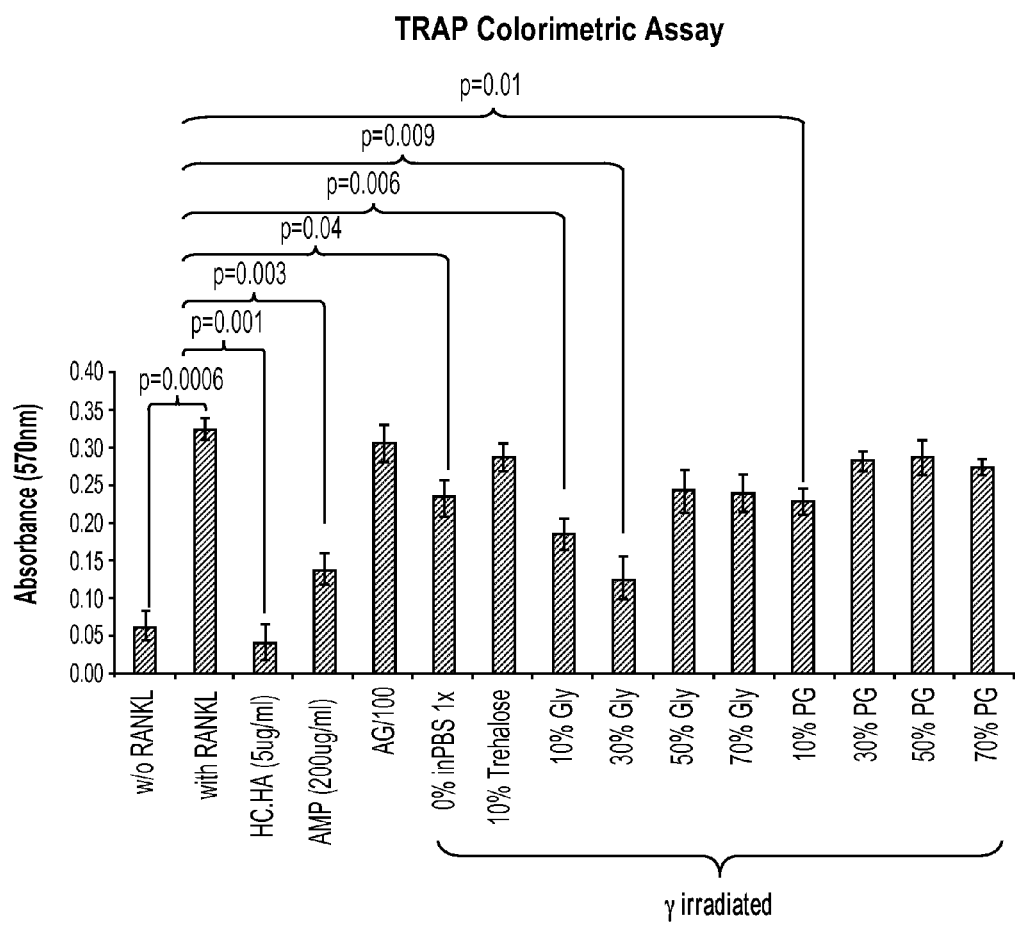
FIG. 5 exemplifies the effects of AM samples on osteoclastogenesis. Osteoclast inhibition by AM was measured by TRAP Colorimetric assay.

The TRAP colorimetric assay revealed that macrophage cells induced with RANKL express the highest concentration of TRAP (FIG. 5). Cells without RANKL treatment had significantly lower TRAP activity (p=0.0006). The experimental controls comprising HC-HA/PTX3 and AM powder (AMP) also showed significant reduction in TRAP activity (p=0.001 & p=0.003). Of the γ-irradiated samples, only AM preserved in PBS, 10% Gly, 30% Gly and 10% PG showed significant inhibition (p<0.05) of osteoclast formation.

AM tissue needs to be γ-irradiated frozen to prevent hydrolysis of water that releases of hydroxyl radicals (OH), hydrogen atoms (H) and electrons (e) that damages the active biochemical components of AM tissue. Based on the protein and HA data, high concentration of glycerol (50% and 70%) and low concentration of propylene glycol (10% and 30%) provides optimal protection against γ-irradiation. Based on the functional analysis, γ-irradiated samples in PBS, 10% Gly, 30% Gly and 10% PG significantly inhibit osteoclast formation.

Example 8

In this example, the effect of room temperature storage on cryopreserved AM after γ-irradiation was assessed by histological assay. The samples were subjected to accelerated aging pursuant to the ASTM F1980 standard (Standard Guide for Accelerated Aging of Sterile Barrier Systems for Medical Devices) where sample products at 55° C. for 46 days are equivalent to 1 year at room temperature. Histological samples were used to determine the shelf life of the fetal support tissue product at room temperature at 1 year and 2 year time points by aging it at 55° C. for 46 days and 92 days respectively. For biochemical and functional analysis (Example 9), AM tissue was kept at 55° C. for 11.5 days (performed using a Hybridization oven) for a room temperature storage readout of 3 months.

The AM used for this study was divided into three groups:

1) Non γ-irradiated AM—Product is aseptically processed. Serves as control.

2) Non γ-irradiated AM Aged for 1.0 Year or 2.0 Year—Product is aseptically processed.

3) γ-irradiated AM Aged for 1.0 Year or 2.0 Year—Product is sterile.

Histological evaluation for establishing the presence of the epithelium, the basement membrane and the stroma structures, whether continuous or discontinuous in the fetal support tissue product was performed as described in Example 6.

γ-irradiated AM test samples aged at 1.0 Yr or 2.0 Yr were compared to the morphology non γ-irradiated AM test samples aged at 1.0 Yr or 2.0 Yr and also compared to the morphology of non γ-irradiated AM (frozen at −80° C. for 1 week) as a control with Analysis of Variance (ANOVA); any statistically significant differences between the control and the test samples were flagged during analysis. If such changes were noted in three different samples, the condition was to be deemed unacceptable unless repeated with enough sample size to arrive at a statistical difference.

This evaluation was considered valid for histological integrity after undergoing γ-irradiation if there was no statistical significance between the control (non γ-irradiated AM), the γ-irradiated AM test samples aged at 1.0 Yr or 2.0 Yr and the non γ-irradiated AM test samples aged at 1.0 Yr or 2.0 Yr.

Analysis of Variance (ANOVA) method is typically used to test a null hypothesis that the means (μ) of more than two populations are equal. In this experiment, there were three populations: 1)+ve Control, 2) γ-irradiated AA 1.0 Yr or 2.0 Yr, and 3) Non γ-irradiated AA 1.0 Yr or 2.0 Yr. ANOVA was used to determine if there were significant structural differences between the non γ-irradiated (Control), the γ-irradiated amniotic membrane (AM) aged at 1.0 Yr or 2.0 Yr, and the non γ-irradiated amniotic membrane (AM) aged at 1.0 Yr or 2.0 Yr with regard to histological quality attributes. Three assumptions were made when analyzing the data: 1) the populations from which the samples are drawn are (approximately) normally distributed; 2) the populations from which the samples are drawn have the same variance (or standard deviation); 3) the samples drawn from different populations are random and independent. The significance level was set at 1% (α=0.01)

Room Temperature Aging for 1.0 Yr

All samples evaluated met the acceptance criteria of "pass" as all sample readout showed continuous or discontinuous histology with overall average ≥50% present. None of the samples evaluated met the "fail" criteria. Through the analysis of variance (ANOVA) method, validation was achieved with regard to histological quality attributes that there is no significant difference between the (+) Control amniotic membrane stored at −80° C. for 1 week and the γ-irradiated amniotic membrane kept at room temperature for 1.0 year. In addition, validation was achieved with regard to histological quality attributes that there is no significant difference between the (+) Control amniotic membrane stored at −80° C. for 1 week and the non γ-irradiated amniotic membrane kept at room temperature for 1.0 year. Validation also was achieved with regard to histological quality attributes that there is no significant difference between the γ-irradiated amniotic membrane kept at room temperature for 1.0 year and the non γ-irradiated amniotic membrane kept at room temperature for 1.0 year.

Room Temperature Aging for 2.0 Yr

All samples evaluated met the acceptance criteria of "pass" as all sample readouts showed continuous or discontinuous histology with overall average ≥50% present. None of the samples evaluated met the "fail" criteria. Thus, validation was achieved with regard to histological quality attributes that there is no significant difference between the (+) Control amniotic membrane stored at −80° C. for 1 week and the γ-irradiated amniotic membrane kept at room temperature for 2.0 year. Validation also was achieved with regard to histological quality attributes that there is no significant difference between the (+) Control amniotic membrane stored at −80° C. for 1 week and the non γ-irradiated amniotic membrane kept at room temperature for 2.0 year. Validation also was achieved with regard to histological quality attributes that there is no significant difference between the γ-irradiated amniotic membrane kept at room temperature for 2.0 year and the non γ-irradiated amniotic membrane kept at room temperature for 2.0 year. Table 33 summarizes the histological analysis data obtained.

TABLE 33

Summary of Histological Analysis

| Study | Storage | Duration | Consistency | Results | Conclusion |
| --- | --- | --- | --- | --- | --- |
| Non γ-irradiated AM vs. γ-irradiated AM | Cryopreserved (−80° C.) | 3 weeks | Samples from 3 different lots (n = 3 per lot) | There was no statistically significant difference between γ-irradiated & non γ-irradiated amniotic membrane with regard to histological quality attributes of epithelium, basement membrane, and stromal layers. | Histological quality data supports that γ-irradiation does not damage cryopreserved amniotic membrane. |
| Control AM vs. Non γ-irradiated AM | Room/Ambient Temperature | 1.0 & 2.0 Year | Samples from 3 different lots (n = 3 per lot) | There was no significant difference between the (+) Control amniotic membrane stored at −80° C. for 1 week and the non γ-irradiated amniotic membrane kept at room temperature for 1.0 and 2.0 year. | Histological quality data supports that Non γ-irradiated AM can be stored at Room Temperature for 1.0 and 2.0 year. |
| Control AM vs. γ-irradiated AM | Room/Ambient Temperature | 1.0 & 2.0 Year | Samples from 3 different lots (n = 3 per lot) | There was no significant difference between the (+) Control amniotic membrane stored at −80° C. for 1 week and the γ-irradiated amniotic membrane kept at room temperature for 1.0 and 2.0 year. | Histological quality data supports that γ-irradiated AM can be stored at Room Temperature for 1.0 and 2.0 year. |
| Non γ-irradiated AM vs. γ-irradiated AM | Room/Ambient Temperature | 1.0 & 2.0 Year | Samples from 3 different lots (n = 3 per lot) | There was no significant difference between the γ-irradiated amniotic membrane kept at room temperature for 1.0 & 2.0 year and the non γ-irradiated amniotic membrane kept at room temperature for 1.0 & 2.0 year. | Histological quality data supports Room Temperature storage for 1.0 and 2.0 Years does not damage γ-irradiated AM and non γ-irradiated amniotic membrane. |

Example 9

In this example the effectiveness of the various Cryo and Radioprotectants for room temperature storage after γ-irradiation was assessed by biochemical and functional analysis.

The concentration for the panel of cryo/radioprotectants was set at 10% for Glycerol, PG, Trehalose and DMSO and was varied for the concentration of both Gly and PG at 0%, 10%, 30%, 50% and 70%. The control was cryopreserved AM in 1:1 DMEM/Glycerol without γ-irradiation. The AM samples were prepared as described in Example 7. AM tissue with and without γ-irradiation was converted into AM extract in accordance sample preparation step outlined in Example 7. Protein concentrations were measured by BCA Protein Assay kit (Pierce, Rockford, Ill.) using the supernatant extracted with 4M Guanidine/HCl and dialyzed against PBS. HA concentration was quantified using the HA Test Kit (Corgenix #029-001, Broomfield, Colo.). Aging of the AM tissue was performed using a Hybridization oven as described in Example 8.

Biochemical Analysis

Figure 6:
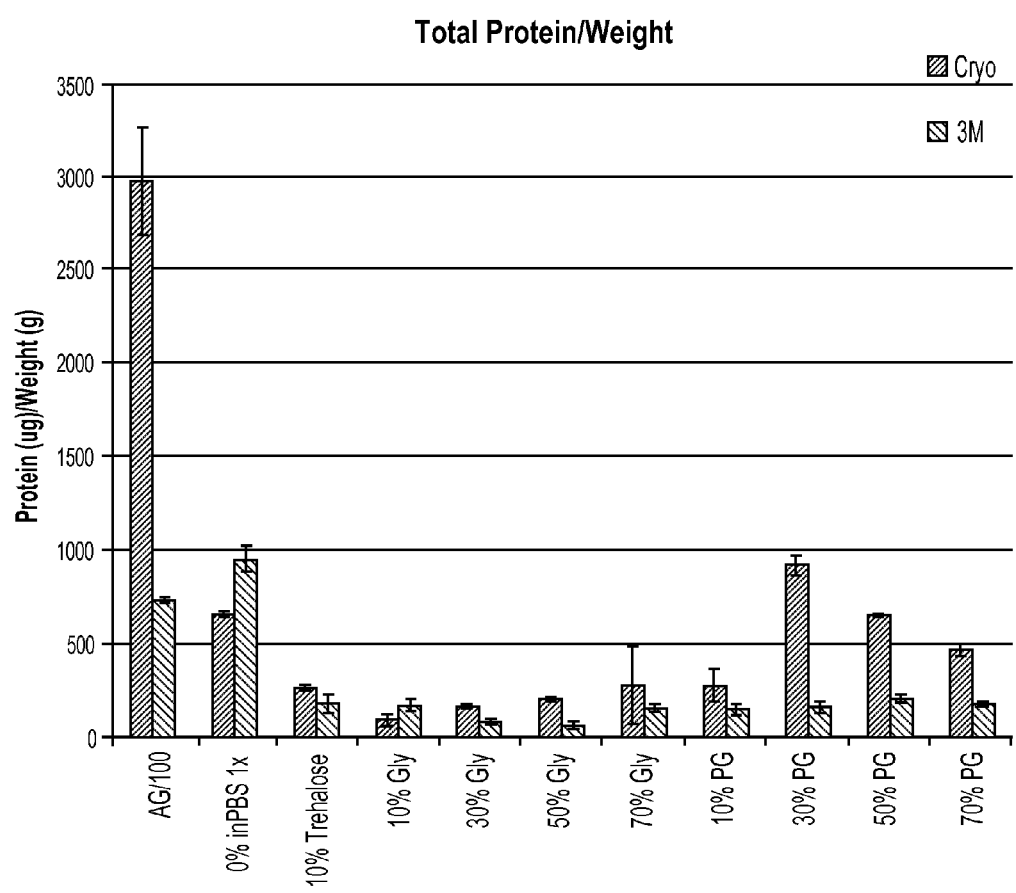
FIG. 6 exemplifies total protein extracted per weight after aging AM samples 3 months at room temperature compared to cryopreserved samples.

The overall protein extracted from AM (with exception of PBS and 10% Glycerol sample) in different cryo-media was reduced after 3 months storage in room temperature compared to the cryopreserved (frozen) samples (FIG. 6). No notable trends were observed for the different concentrations of glycerol and propylene glycol unlike their cryopreserved samples. The amount of protein extracted in γ-irradiated AM tissue after 3 months aging is in the order: PBS>50% PG>70% PG=30% PG=10% Trehalose=10% Glycerol=70% Glycerol.

Figure 7:
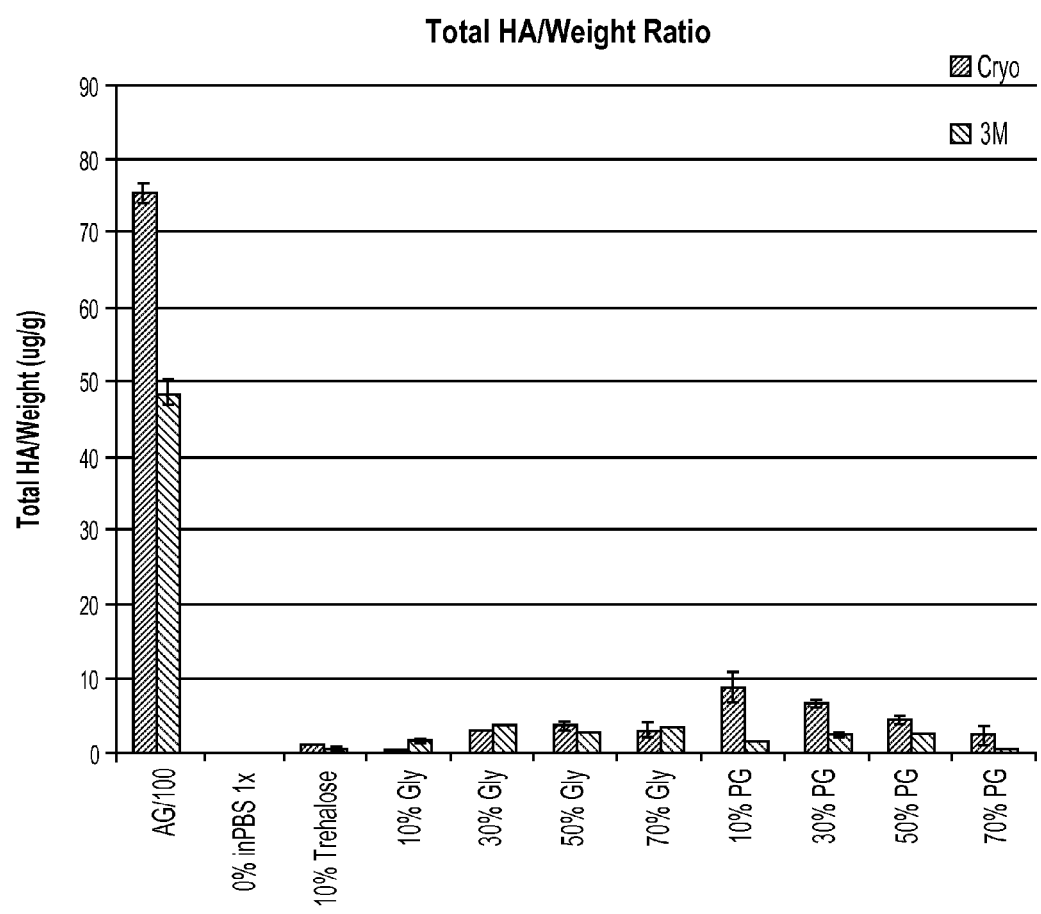
FIG. 7 exemplifies total HA extracted per weight after aging AM samples 3 months at room temperature compared to cryopreserved samples.

The overall trend for γ-irradiated Gly samples also showed the same levels of HA extraction after 3 months RT storage compared to the cryopreserved control (FIG. 7). The only exception to this is the PG samples and CTL (AG/100) samples which showed reduced HA levels after 3 months RT storage compared to the cryopreserved samples. The amount of HA present in γ-irradiated AM tissue after 3M RT storage is in the order: 30% Glycerol>50% Glycerol=70% Glycerol>30% PG=50% PG.

Figure 8:
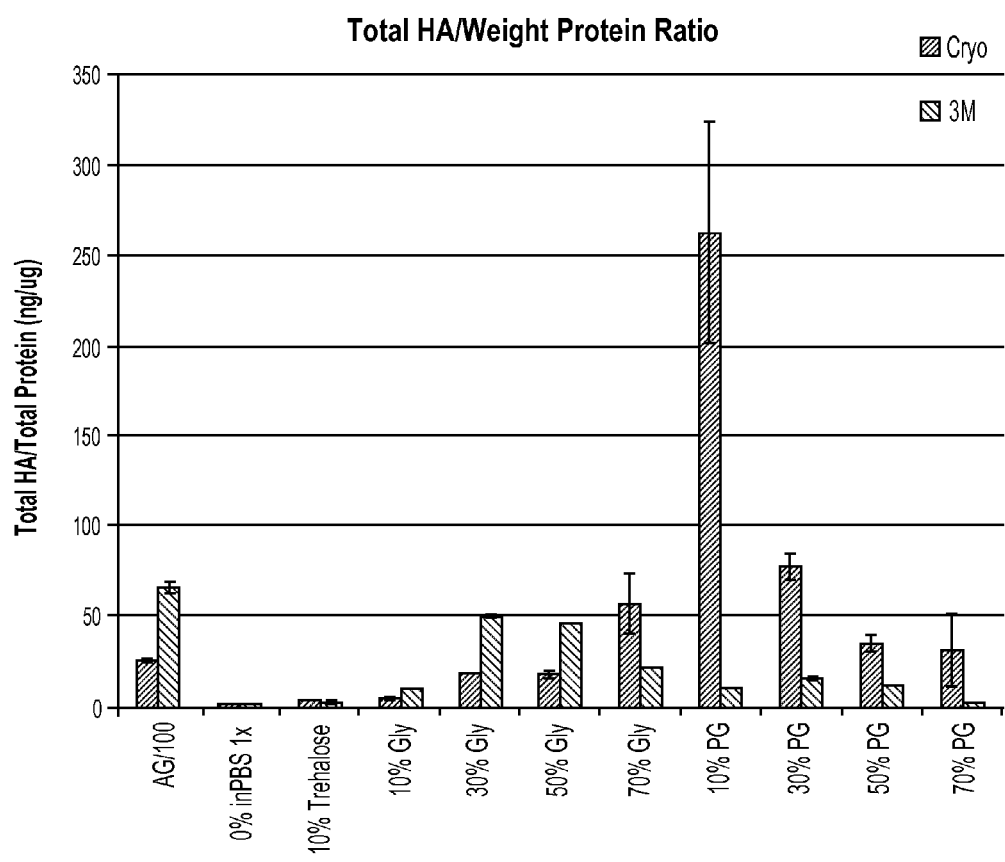
FIG. 8 exemplifies total HA extracted per total protein extracted after aging AM samples 3 months at room temperature compared to cryopreserved samples.

The HA:Protein ratio revealed that 30% Gly extracts had the highest amount of HA after 3 months RT storage followed by 50% Gly and 70% Gly (FIG. 8). The HA:Protein ratio also showed that HA levels are markedly reduced in all PG samples after 3 months RT storage.

Functional Analysis—Osteoclast Assay

Figure 9:
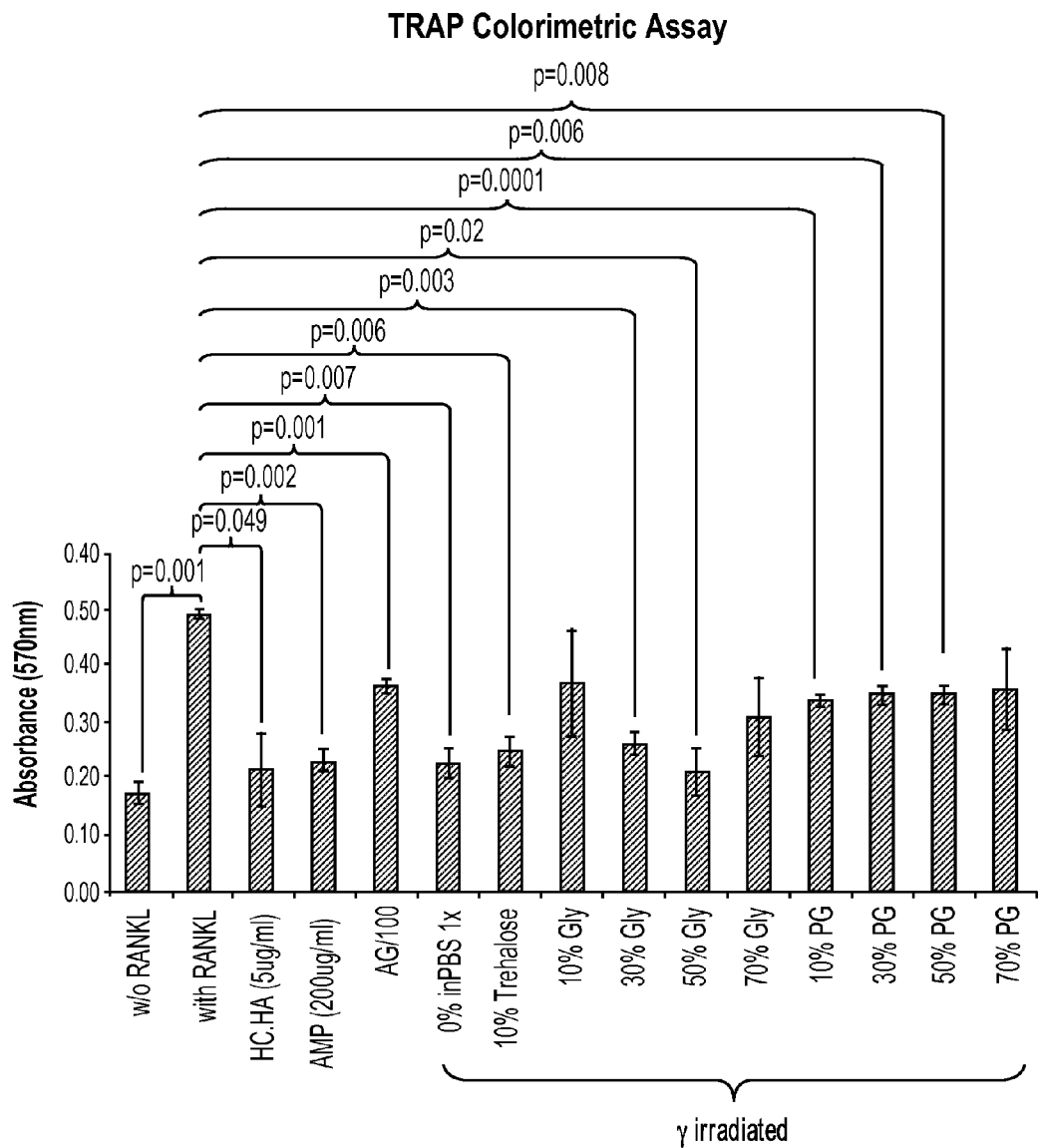
FIG. 9 exemplifies the effects of AM on osteoclastogenesis after aging AM samples 3 months at room temperature compared to cryopreserved samples. Osteoclast inhibition by AM was measured by TRAP Colorimetric assay.

Murine RAW 264.7 macrophage cells treated with 50 ng/ml of RANKL were dosed with 1 volume fraction of AM samples to determine its potency of inhibiting osteoclast formation as described in Example 7. Inhibition of osteoclast formation was assessed by TRAP colorimetric assay. The TRAP colorimetric assay revealed that macrophage cells induced with RANKL expressed the highest concentration of TRAP (FIG. 9). Cells without RANKL treatment had significantly lower TRAP activity (p=0.001). The experimental controls comprising of HC-HA/PTX3 and AM powder (AMP) also showed significant reduction in TRAP activity (p=0.049 & p=0.002 respectively). Of the γ-irradiated samples, AM without γ-irradiation (AG/100) and γ-irradiated AM preserved in PBS, 10% Trehalose, 30% Gly, 50% Gly, 10% PG, 30% PG and 50% PG showed significant inhibition (p<0.05) of osteoclast formation. This indicated that the functional components of AM are still preserved in γ-irradiated AM after 3 months RT storage.

In summary, based on the protein data, γ-irradiated AM samples are best preserved in PBS, 50% PG, 70% PG, 10% Gly, and 70% Gly for storage at RT. Based on the HA data, γ-irradiated AM samples are best preserved in 30% Glycerol, 50% Glycerol, 70% Glycerol, 30% PG and 50% PG for storage at RT. Based on the HA:Protein ratio, γ-irradiated AM samples are best preserved in 30% Glycerol, 50% Glycerol, and 70% Glycerol, for storage at RT. Based on the functional analysis, γ-irradiated samples in 50% Gly, PBS, 10% Trehalose, 30% Gly, 10% PG and 30% PG significantly inhibited osteoclast formation.

Table 34 summarizes the biochemical and functional analysis data obtained. The summarized data indicates that high concentration of glycerol (ranging from 30%-70%) and low concentration of propylene glycol (10%-30%) best protect AM against radiation damage based on the total protein, HA and other active ingredients extracted from the tissue.

While preferred embodiments have been shown and described herein, it will be obvious to those skilled in the art that such embodiments are provided by way of example only. Numerous variations, changes, and substitutions may now occur. It should be understood that various alternatives to the embodiments described herein may be employed in practicing the described methods. It is intended that the following claims define the scope of the embodiments and that methods and structures within the scope of these claims and their equivalents be covered thereby.

What is claimed is:

1. A sterilized fetal support tissue product, comprising: (i) a fetal support tissue that is not dry, and (ii) an isotonic solution; wherein:
   a) the fetal support tissue product is sterilized by exposing the fetal support tissue in combination with the isotonic solution to γ-irradiation at a temperature of less than or equal to 0° C., and at a dosage sufficient to sterilize the fetal support tissue product;
   b) anti-inflammatory activity of HC-HA/PTX3 of the fetal support tissue is substantially maintained in the sterilized fetal support tissue product, and is stable at room temperature for at least 1 month; and
   c) the sterilized fetal support tissue product comprises cells, substantially all of which are dead.

2. The sterilized fetal support tissue product of claim 1, wherein the sterilized fetal support tissue product has a Sterility Assurance Level (SAL) of $10^{-6}$.

3. The sterilized fetal support tissue product of claim 1, wherein structural integrity of the fetal support tissue is maintained.

4. The sterilized fetal support tissue product of claim 1, wherein the sterilized fetal support tissue is stable at room temperature for at least 6 months.

5. The sterilized fetal support tissue product of claim 1, wherein the fetal support tissue is from placental amniotic

TABLE 34

Summary of Biochemical and Functional Analysis after γ-irradiation and RT storage

| | | | Optimal Preservation Media | | |
|---|---|---|---|---|---|
| Study | Storage | Duration | 1 | 2 | 3 |
| Protein/Weight | Cryopreserved (−80° C.) | 1 Month | 30% PG | 50% PG, PBS | 50% Gly, 70% Gly, 70% PG |
| | Room Temperature | 3 Months | PBS | 50% PG | 10% Gly, 70% Gly, 30% PG |
| HA/Weight | Cryopreserved (−80° C.) | 1 Month | 10% PG | 30% PG | 50% PG, 50% Gly, 70% Gly |
| | Room Temperature | 3 Months | 30% Gly | 50% Gly, 70% Gly | 30% PG, 50% PG |
| HA/Protein Ratio | Cryopreserved (−80° C.) | 1 Month | 10% PG | 30% PG | 70% Gly |
| | Room Temperature | 3 Months | 30% Gly | 50% Gly | 70% Gly, 30% PG |
| Osteoclast Assay | Cryopreserved (−80° C.) | 1 Month | 30% Gly | 10% Gly | PBS, 10% PG |
| | Room Temperature | 3 Months | 50% PG | PBS | 30% Gly, 10% Trehalose | membrane, umbilical cord amniotic membrane, chorion, amnion-chorion, placenta, umbilical cord, or a any combination thereof.

6. The sterilized fetal support tissue product of claim 1, wherein the fetal support tissue is a tissue graft.

\* \* \* \* \*